United States Patent

Dahm et al.

[11] 4,051,250
[45] Sept. 27, 1977

[54] ANTIINFLAMMATORY AZOLE DERIVATIVES

[75] Inventors: Johann Dahm, Eschollbrucken; Joachim Borck, Darmstadt; Albrecht Wild, Darmstadt; Jan Willem Hovy, Darmstadt, all of Germany

[73] Assignee: Merck Patent Gesellschaft mit beschrankter Haftung, Darmstadt, Germany

[21] Appl. No.: 624,447

[22] Filed: Oct. 21, 1975

Related U.S. Application Data

[62] Division of Ser. No. 260,307, June 6, 1972, Pat. No. 3,933,840.

[30] Foreign Application Priority Data

June 11, 1971    Germany .................... 2129012

[51] Int. Cl.$^2$ .................. A61K 31/42; A61K 31/425
[52] U.S. Cl. ..................................... 424/272; 424/270
[58] Field of Search ................................ 424/272, 270

[56] References Cited

U.S. PATENT DOCUMENTS

| 2,513,923 | 7/1950 | Duffin et al. ......................... 260/302 |
| 3,578,671 | 5/1971 | Brown ................................... 260/307 |
| 3,933,840 | 1/1976 | Dahm et al. ....................... 260/307 R |

*Primary Examiner* — Leonard Schenkman
*Attorney, Agent, or Firm* — Millen & White

[57] ABSTRACT

Azole derivatives of the formula

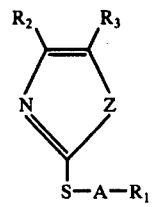

wherein $R_1$ is free or esterified carboxyl or other functionally modified carboxyl group, $R_2$ and $R_3$ each are aryl; A is $C_nH_{2n}$ in which $n$ is an integer from 1 to 10, inclusive; and Z is O or S; and the physiologically acceptable salts thereof, possess, with good compatibility, excellent antiphlogistic activity and, in particular, influence favorably the chronic progressive diseases of the joints, e.g., arthritis. They can be prepared from compounds of the formula

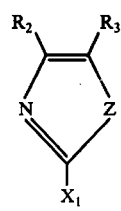

wherein $X_1$ is a group convertible into the group —S—A—$R_1$, and $R_2$ and $R_3$ have the values given above.

19 Claims, No Drawings

ANTIINFLAMMATORY AZOLE DERIVATIVES

This is a division of application Ser. No. 260,307 filed June 6, 1972, now U.S. Pat. No. 3,933,840.

BACKGROUND OF THE INVENTION

This invention relates to novel azole derivatives. Compounds of this type have been described, e.g., in U.S. Pat. No. 3,578,671.

SUMMARY OF THE INVENTION

The novel compounds of this invention are azole derivatives of the general Formula I

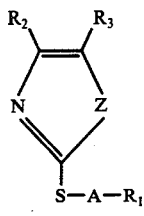

wherein $R_1$ is carboxyl, esterified carboxyl or other functionally modified carboxyl group; $R_2$ and $R_3$ each are aryl of up to 10 carbon atoms; A is $C_nH_{2n}$ in which n is an integer from 1 to 10, inclusive; and Z is O or S, and the physiologically acceptable salts thereof.

Compounds of Formula I, with good compatibility, possess excellent antiphlogistic activity and in particular, have a favorable influence on the chronic progressive diseases of the joints, e.g., arthritis. The also possess analgesic and antipyretic acitivity. The compounds of Formula I can thus be utilized as medicines for obtaining an antiphlogistic effect in living beings and also as intermediates for the preparation of other drugs.

DETAILED DISCUSSION

Preferred compounds of this invention are those of Formulae Ia through Im below, which otherwise correspond to Formula I, i.e., the groups not recited therein have the values set forth for Formula I:

Ia — $R_1$ is a free or esterified carboxyl group of a total of 1-15 carbon atoms, $CONH_2$ or CN;

Ib — $R_1$ is $COOR_5$ wherein $R_5$ is H or alkyl, cycloalkyl, cycloalkylalkyl, aryl or aralkyl of up to 12 carbon atoms, respectively, and optionally containing 1-2 C—C multiple bonds and/or being interrupted one or more times by Q and/or being branched and/or being mono- or polysubstituted by OH, SH and/or $NH_2$, Q being O, S, NH, optionally OH-substituted N-alkyl of 1-6 carbon atoms, N-aryl of 6-10 carbon atoms or N-aralkyl of 7-10 carbon atoms;

Ic — $R_1$ is $COOR_6$ wherein $R_6$ is H, alkyl of 1-6 carbon atoms, or dialkylaminoalkyl, pyrrolidinoalkyl, piperidionalkyl or morpholinoalkyl of respectively up to 10 carbon atoms;

Id — $R_1$ is COOH or COO-alkyl of 1-6 carbons, preferably $COOCH_3$ or $COOC_2H_5$;

Ie — A is —$CH_2$—, —$CH(CH_3)$— or —$CH(C_2H_5)$—, especially those of Ia, Ib, Ic and Id;

If — $R_2$ and $R_3$ each are phenyl groups, optionally mono-, di- or polysubstituted by alkyl, alkoxy, alkylmercapto, monoalkylamino, dialkylamino or acylamino wherein the alkyl, alkoxy and acyl each contain up to 4 carbon atoms, F, Cl, Br, I, $CF_3$, OH, methylenedioxy, $NH_2$ or $NO_2$, especially those of Ia - Ie, inclusive;

Ig — $R_2$ and $R_3$ each are phenyl groups, optionally monosubstituted, preferably in the p-position, by methyl, methoxy, methylmercapto, F, Cl, Br or $CF_3$, especially those of Ia - Ie, inclusive;

Ih — $R_2$ and $R_3$ are phenyl or p-chlorophenyl, especially those of Ia -Ie, inclusive;

Ii — $R_1$ is COOH, $COOCH_3$ or $COOC_2H_5$, A is —$CH_2$—, —$CH(CH_3)$— or —$CH(C_2H_5)$— and $R_2$ and $R_3$ are phenyl or phenyl substituted in the p-position by methyl, methoxy, methylmercapto, F, Cl, Br or $CF_3$;

Ik — $R_1$ is COOH, $COOCH_3$ or $COOC_2H_5$, A is —$CH_2$—, —$CH(CH_3)$— or —$CH(C_2H_5)$— and $R_2$ and $R_3$ are phenyl or p-chlorophenyl;

Il — Oxazoles of Formulae Ia - Ik, inclusive, i.e., Z is O; and

Im — Thiazoles of Formulae Ia - Ik, inclusive, i.e., Z is S.

In its process aspect, this invention relates to a process for the preparation of compounds of general Formula I wherein a. the group $X_1$ of a compound of the general Formula II

wherein $X_1$ is a group convertible to the group —S—A—$R_1$ as defined above and Z, $R_2$ and $R_3$ have the values given above, is converted into the group —S—A—$R_1$; or b. a compound of the general Formula III

wherein $R_4$ is the group $R_2$—CY—$CHR_3$—Z—C(=NH)— or $R_3$—CY—$CHR_2$—NH—CZ—, Y is O or S, and $R_1$, $R_2$, $R_3$, A and Z have the values given above, is treated with an agent capable of splitting off $H_2Y$; and, optionally thereafter, one or more of $R_1$, $R_2$ and/or $R_3$ groups of a thus-obtained product of Formula I, are converted into $R_1$, $R_2$ and/or $R_3$ groups of a different value.

In the above formulae, $R_1$ preferably is a free COOH-group. $R_1$ can also be an esterified COOH-group, e.g., wherein the alcohol portion of the ester group is preferably of 1-14 carbon atoms, and more preferably hydrocarbon, e.g., alkyl. Because the free carboxylic acids of Formula I ($R_1$ = COOH) are physiologically effective and the corresponding esters can be saponified to the free carboxylic acids under physiological conditions, like acid addition salts of the free bases, the exact nature of the ester group is not critical, so long as it is a physiologically acceptable group. It is possible, of course, to modify the physiological effects of the parent azole by an appropriate selection of the ester group. For example, depot effects can be achieved by the use of long-chain or difficult-to-saponify alcohol residues. Improved solubility can be achieved by a polar group (O-atoms, S-atom, N-atom) in the alcohol moiety. Pharmacological effects in addition to the antiphlogistic activity of the parent azole can be obtained by the esterification of the acids I ($R_1$ = COOH with OH-compounds which themselves exhibit pharmacological effectiveness, e.g., pyridoxine, corticoidally effective 21-hydroxy steroids, etc. However, alcohol moieties which are essentially inert are preferred.

For example, $R_1$ can be $COOR_5$ or $COOR_6$ as defined above, but preferably is COOH, $COOCH_3$ or $COOC_2H_5$.

$R_5$ preferably is hydrogen; alkyl, e.g., methyl, ethyl, n-propyl, isopropyl, n-butyl, isobutyl, sec.-butyl, tert.-butyl, n-pentyl, isoamyl, n-hexyl, n-heptyl, n-octyl, 2-ethylhexyl, n-nonyl, n-decyl, n-undecyl, n-dodecyl, n-tridecyl, n-tetradecyl; alkenyl, preferably of 2–4 carbon atoms, e.g., vinyl, allyl, crotyl; alkinyl, preferably of 2–4 carbon atoms, e.g., propargyl; hydroxyalkyl, preferably wherein the hydroxy group is separated by at least 2 carbon atoms from the carboxy group, e.g., 2-hydroxyethyl, 2-hydroxypropyl, 3-hydroxypropyl; alkoxyalkyl, preferably wherein the alkoxy group is separated by at least 2 carbon atoms from the carboxy group, e.g., 2-methoxyethyl, 2-ethoxyethyl, and the corresponding groups having an oxygen atom in the chain separated by at least 2 carbon atoms from other functional groups, e.g., 3-oxa-5-hydroxypentyl, 3-oxa-5-methoxypentyl, 3-oxa-5-butoxypentyl, 3,6-dioxa-8-hydroxyoctyl, 3,6-dioxa-8-methoxyoctyl, 3,6-dioxa-8-ethoxyoctyl, 3-oxa-5-ethoxypentyl; primary, secondary or tertiary aminoalkyl, e.g., wherein the amino group is separated by at least 2 carbon atoms from the carboxy group, including aminoalkyl, e.g., 2-aminoethyl, 3-aminopropyl; dialkylaminoalkyl, e.g., 2-dimethylaminoethyl, 2-diethylaminoethyl, 2-di-n-propylaminoethyl, 3-dimethylaminopropyl, 3-diethylaminopropyl, 2-methyl-3-diethylaminopropyl, 4-dimethylaminobutyl, 4-diethylaminobutyl; cycloalkyl and cycloalkyl-alkyl, e.g., containing 3–8 ring carbon atoms, preferably 5 or 6, e.g., cyclopentyl, cyclohexyl; 2-cyclohexylethyl, 3-cyclohexylpropyl; azacycloalkyl, azacycloalkylalkyl and related cyclic groups, preferably containing a total of 5–6 ring members and 1–2 of N and 0–1 of O or S as ring members in addition to ring carbon atoms, e.g., N-methylpiperidyl-(4); (N-methylpiperidyl-3)-methyl, 2-(N-methylpiperidyl-2)-ethyl, pyrrolidinoalkyl, e.g., 2-pyrrolidinoethyl, piperidinoalkyl, e.g., 2-piperidinoethyl, homopiperidinoalkyl, e.g., 2-homopiperidinoethyl, morpholinoalkyl, e.g., 2-morpholinoethyl, 2-thiomorpholinoalkyl, e.g., morpholinoethyl, N'-alkylpiperazinoalkyl, e.g., 2-(N-methylpiperazino)-ethyl, 2-(N-ethylpiperazino)-ethyl, N'-arylpiperazinoalkyl wherein aryl is as defined below, 2-(N-phenylpiperazino)-ethyl, N'-hydroxyalkylpiperazinoalkyl, e.g., 2-(N-2-hydroxyethylpiperazino)-ethyl, 2-(N-methylhomopiperazino)-ethyl, N'-aralkylpiperazinoalkyl wherein aralkyl is as defined below, e.g., 2-(N-benzylpiperazino)-ethyl, the corresponding cyclic aminopropyl groups, e.g., 2-pyrrolidinopropyl, 3-pyrrolidinopropyl, 2-piperidinopropyl, 3-piperidinopropyl, 2-(N-methylpiperazino)-propyl, 3-(N-methylpiperazino)-propyl, 3-(N-ethylpiperazino)-propyl, 3-(N-phenylpiperazino)-propyl, 2-morpholinopropyl, 3-morpholinopropyl, 3-thiomorpholinopropyl, 2-methyl-3-pyrrolidinopropyl, 2-methyl-3-piperidinopropyl, 2-methyl-3-morpholinopropyl; mercaptoalkyl and alkylmercaptoalkyl, preferably wherein the mercapto group is separated from the carboxy group by at least 2 carbon atoms, e.g., 2-mercaptoethyl, 2-methylmercaptoethyl, 2-ethylmercaptoethyl, 3-methylmercaptopropyl, 3-ethylmercaptopropyl; aryl, preferably of 6–12 ring carbon atoms and 1–2 fused or separate rings, e.g., phenyl, alkaryl, e.g., o-tolyl, m-tolyl, p-tolyl, p-ethylphenyl, 1-naphthyl, 2-naphthyl; aralkyl, e.g., benzyl, p-methylbenzyl, 1-phenylethyl and 2-phenylethyl.

$R_1$ can be other functionally modified carboxyl groups as well as esterified carboxyl. Examples of such groups are: acid halogenides ($R_1$ = COF, COCl, COBr); ortho esters [$R_1$ = $C(OR_7)_3$]; acid anhydrides ($R_1$ = COOAcyl wherein Acyl is the acyl radical of a carboxylic acid of up to 34 carbon atoms, preferably of an acid of Formula I ($R_1$ = COOH), i.e., an azole otherwise corresponds to Formula I wherein $R_1$ is —CO—; nitriles ($R_1$ = CN); acid amides ($R_1$ = $CONH_2$, $CONHR_7$, or $CONR_7R_8$); hydroxamic acids ($R_1$ = CONHOH); acid hydrazides ($R_1$ = $CONHNH_2$ or $CONHNHR_7$); acid azides ($R_1$ = $CON_3$); imino ethers ($R_1$ = $C(OR_7)$=NH); acid amidines ($R_1$ = $C(=NH)NH_2$); acid hydrazidines ($R_1$ = $C(NH_2)$=$NNH_2$ or $C(NHNH_2)$=NH); thio acids ($R_1$ = CSOH or COSH); thio acid esters ($R_1$ = $CSOR_7$ or $COSR_7$); thioamides ($R_1$ = $CSNH_2$, $CSNHR_7$ or $CSNR_7R_8$), $R_7$ and $R_8$, respectively, in each instance being identical or different alkyl of up to 8, preferably up to 4 carbon atoms, especially methyl or ethyl, or collectively, tetramethylene, pentamethylene or ethylenoxyethylene.

Examples of preferred substituted amides are N-monoalkyl amides, i.e., $R_1$ = CONH alkyl, e.g., methyl amides, ethyl amides, n-propyl amides, isopropyl amides, n-butyl amides, isobutyl amides; N,N-dialkyl amides, i.e., $R_1$ = $CON(alkyl)_2$, e.g., dimethyl amides, methylethyl amides, diethyl amides, di-n-propyl amides, diisopropyl amides, di-n-butyl amides, diisobutyl amides; N-monoaryl and N-monoaralkyl amides, i.e., $R_1$ = CONHAryl and —CON alkylaryl, e.g., anilides and N-benzyl amide; N-hydroxyalkyl amides, e.g, N-2-hydroxyethyl amides; N,N-bis(hydroxyalkyl) amides, e.g., N,N-bis(2-hydroxyethyl) amides; heterocyclic amides, e.g, pyrrolidides, piperidides, morpholides, thiomorpholides, piperazides, N'-alkylpiperazides, e.g., N'-methylpiperazides, N'-ethylpiperazides and N'hydroxyalkylpiperazides, e.g, N'-2-hydroxyethylpiperazides.

$R_2$ and $R_3$ can be different but preferably are identical aryl, i.e., carbocyclic aromatic, groups. Each preferably are phenyl groups, which groups optionally can be mono- or polysubstituted, e.g., by 1, 2, 3 or more of alkyl, alkoxy, alkylmercapto, monoalkylamino, dialkylamino and/or acylamino (alkanoylamino) of a total of up to 4 carbon atoms, e.g., methyl, ethyl, n-propyl, isopropyl, n-butyl, isobutyl, sec.-butyl, tert.-butyl, methoxy, ethoxy, n-propoxy, isopropoxy, n-butoxy, isobutoxy, sec.-butoxy, tert.-butoxy, methylmercapto, ethylmercapto, n-propylmercapto, isopropylmercapto, n-butylmercapto, isobutylmercapto, tert.-butylmercapto, methylamino, ethylamino, n-propylamino, isopropylamino, n-butylamino, isobutylamino, sec.-butylamino, tert.-butylamino, dimethylamino, methylethylamino, diethylamino, formamido, acetamido, propionamido, butyramido, isobutyramido; or by F, Cl, Br, I, OH or methylenedioxy; by $NH_2$ and/or $NO_2$; by SH, alkylsulfinyl, e.g., methylsulfinyl, alkylsulfonyl, e.g., methylsulfonyl, $SO_3H$, $SO_2NH_2$, COOH, CHO and/or COOAlkyl, wherein the alkyl in each instance is of 1–3 carbon atoms. Of the substituted $R_2$ and/or $R_3$ groups, the monosubstituted are preferred, especially those substituted in the p-position. A can be, for example, $-(CH_2)_n-$ and $-CH(CH_2)_{n-1}H-$, wherein $n$ is an integer of from 1-10, inclusive, preferably 1-6 especially 1-3. A preferably is $-CH_2-$, $-CH(CH_3)-$ or $-CH(C_2H_5)-$. In the compounds of general Formula II, $X_1$ preferably is a mercapto (HS—) group, which can also be present in the form of a mercaptide, particularly a metal mercaptide, e.g., an alkali metal, alkaline earth metal or heavy metal mercaptide, preferably in the form of the sodium, potassium, silver, lead, zinc or mercury mercaptide. $X_1$ can, in particular, also be $X_2$ wherein $X_2$ is Cl, Br, I or a residue analogous to halogen. The term "residues analogous to halogen" is understood to mean those $X_2$ residues which can be split off, under the reaction conditions, as $HX_2$ analogously to Cl, Br or I, such as, for example, $NH_2$, alkylsulfonyloxy of preferably 1-6 carbon atoms, e.g., methanesulfonyloxy, arylsulfonyloxy of preferably 6-10 carbon atoms, e.g., benzenesulfonyloxy, p-toluenesulfonyloxy, 1- or 2-naphthalenesulfonyloxy, acyloxy of preferably 1-7 carbon atoms, e.g., acetoxy or other alkanoyloxy, benzoyloxy or other aroyloxy, or an etherified OH-group of preferably 1-7 carbon atoms, e.g., methoxy or other alkoxy, benzyloxy.

$X_1$ can, for example, also be the group $-S-A-R_9$ wherein $R_9$ is a group convertible to $R_1$, preferably by oxidation, e.g., $-CHO$ or $-CH_2OH$. $X_1$ can also be the group $-S-CO-O-A-R_1$ or the group $-S-A_1-COOH$ wherein $A_1$ is $-C_mH_{2m}-CR_1 C_pH_{2p+1})-$ and $m$ and $p$ are integers from 0-9, inclusive, the sum of which is $(n-1)$, which can be converted, by decarboxylation, into the group $-S-A-R_1$. $X_1$ can also be the group $-S-A_1-COR_{10}$ wherein $A_1$ has the values given above and $R_{10}$ is preferably H, alkyl of up to 4 carbon atoms or phenyl, which group can be converted into the group $-S-A-R_1$ by acid cleavage.

Compounds of the general Formula I are suitably produced by (a) reacting a compound of Formula II ($X_1 = $ SH) or a corresponding metal mercaptide, with a compound of the formula $X_2-A-R_1$; or (b) reacting a compound of Formula II ($X_1 = X_2$) with a compound of the formula $HS-A-R_1$ or with a corresponding metal mercaptide; or (c) converting, in a compound of Formula II ($X_1 = -S-A-R_9$), the group $R_9$ into the group $R_1$, preferably by treatment with an oxidizing agent; or (d) treating a compound of Formula II wherein $X_1$ is $-S-CO-O-A-R_1$ or $-S-A_1-COOH$ with a decarboxylating agent; or (e) treating a compound of Formula II wherein $X_1$ is $-S-A_1-COR_{10}$ with a strong base.

Preferably, the compounds of Formula I are obtained by reacting a mercaptoazole of Formula II ($X_1 = $ SH) with a halo-fatty acid derivative of the formula $X_2-A-R_1$, preferably $Cl-A-R_1$ or $Br-A-R_1$, e.g., chloro- or bromoacetic acid, the ethyl ester of chloro- or bromoacetic acid, 2-chloro- or 2-bromopropionic acid, chloroacetonitrile or bromoacetamide. In place of the compound $X_2-A-R_1$, there can be employed the corresponding unsaturated compounds differing from $X_2-A-R_1$ by the absence therefrom of $HX_2$, e.g., acrylic acid, crotonic acid and the derivatives thereof, e.g., methyl acrylate and acrylonitrile. It is also possible to employ diazo-fatty acid derivatives, e.g., diazoacetic acid methyl ester or ethyl ester, in place of $X_2-A-R_1$. Normally, the process is conducted in the presence of a base, e.g., a metallic oxide, for example, an oxide of silver, lead, zinc, mercury or calcium; of a metal hydroxide, especially an alkali metal hydroxide or alkaline earth metal hydroxide, e.g., NaOH, KOH, LiOH and $Ca(OH)_2$; an alkali or alkaline earth metal carbonate, e.g., $Na_2CO_3$ or $K_2CO_3$ an alkali or alkaline earth metal hydride, e.g., NaH or KH; an alkali or alkaline earth metal alcoholate, e.g., sodium or potassium methylate, sodium or potassium ethylate and potassium tert.-butylate; or in the presence of an organic base, e.g., triethylamine or benzyltrimethylammonium hydroxide or other tertiary or quaternary amine. The last-mentioned organic bases are suitable, in particular, for the reaction of the mercaptoazoles with acrylic acid derivatives, e.g., for cyanoethylation. Basically, all salt-forming (mercaptide-forming) bases are suitable. The reaction with diazo-fatty acid derivatives is also accomplished without the addition of a base, e.g., by heating in an inert solvent until the evolution of nitrogen has ceased. The corresponding mercaptide is formed as the intermediate product in the reaction of the mercapto compound II ($X_1 = $ SH) with the base. If a halo-fatty acid is utilized as the reactant, this compound is preferably employed in the form of a salt thereof, e.g., Na, K, Li or Ba salt. The reaction can be conducted in the absence or preferably in the presence of an inert solvent or suspending agent, for example, hydrocarbons, e.g., benzene, toluene, or xylene; alcohols, e.g., methanol, ethanol, isopropanol, n-propanol, n-butanol, or tert.-butanol; ethers, e.g., diethyl ether, diisopropyl ether, tetrahydrofuran (THF), dioxane, or diethylene glycol dimethyl ether; amides, e.g., acetamide, dimethylformamide (DMF); nitriles, e.g., acetonitrile; sulfoxides, e.g., dimethyl sulfoxide; water; and mixtures thereof. The reaction is conducted at temperatures of from about 0° to about 200° C., preferably 20° to 150° C. The duration of the reaction ranges from about 10 minutes to several days, depending on the conditions employed. When operating without solvent, e.g., when melting a sodium mercaptide II ($X_1 = $ SNa) together with a bromo-fatty acid salt (e.g., $Br-A-COONa$), higher temperatures of up to about 300° C. can also be utilized. It can be advantageous to conduct the reaction under an inert gas, e.g., nitrogen or argon. Normally, somewhat longer reaction times are required for the synthesis of the thiazole derivatives (Z=S) than for the synthesis of the oxazole derivatives (Z=O).

Compounds of the general Formula II wherein $X_1 = X_2$ can be reacted with mercapto-fatty acid derivatives of the formula $HS-A-R_1$ and/or the corresponding mercaptides under analogous conditions. Advantageously, a 2-haloazole (II, $X_1 = $ Cl or Br) is allowed to react with a sodium mercaptide $NaS-A-R_1$ in one of the above-mentioned solvents for about 10 minutes to 48 hours, preferably for 1-12 hours, at temperatures of between about 0° and about 200° C., preferably between 40° and 130° C.

The starting compounds of Formula II are normally produced from the corresponding benzoins $R_2-CHOH-CO-R_3$, some of which are known. They can be obtained according to methods known from the literature, e.g., by a benzoin condensation or by condensing phenylacetyl chlorides $R_2-CH_2-CO-Cl$ with aromatic compounds $H-R_3$ in the presence of $AlCl_3$ to the deoxybenzoins $R_2-CH_2-CO-R_3$, bromination of the latter to the desyl bromides $R_2-CHBr-CO-R_3$, followed by reaction with sodium acetate to the acetates $R_2-CH(OCOCH_3)-CO-R_3$ and hydrolysis to the free benzoin. By reacting the benzoins with HSCN, the 2-mercaptooxazoles II ($X_1 = $ SH, Z = O)

are obtained. The 2-mercaptothiazoles II ($X_1$ = SH, Z = S) can be produced, for example, by reacting the desyl bromides with ammonium dithiocarbamate instead of sodium acetate. 2-Haloazoles of Formula II (Z = O, $X_1$ = Cl or Br) can be prepared from the corresponding 4,5-diaryloxazolones and/or -thiazolones with $POCl_3$ and/or $POBr_3$.

The aldehydes or alcohols of Formula II wherein $X_1$ = —S—A—CHO or —S—A—CH$_2$OH, obtainable, for example, by the reaction of compounds of Formula II wherein $X_1$ = SH, or the corresponding metal mercaptides, with aldehydes and/or alcohols of the formulae $X_2$—A—CHO and $X_2$—A—CH$_2$OH, respectively, can be oxidized to the carboxylic acids of Formula I ($R_1$ = COOH) as described in the literature, especially with air or oxygen, preferably in the presence of a catalyst; with $Ag_2O$, preferably as a mixture with CuO; with AgOH, preferably in an aqueous-alcoholic medium under an inert gas, e.g., nitrogen; with $KMnO_4$ in an acidic, neutral or alkaline medium, optionally in the presence of $MgSO_4$; with chromic acid or $CrO_3$, preferably in acetic acid, optionally with the addition of benzene or sulfuric acid; or with hypohalites. In these oxidations, inert solvents are advantageously utilized, e.g., water acetic acid, dioxane, benzene, acetone, THF, DMF, methanol, ethanol or a mixture thereof. The reaction is carried out at temperatures of from about −30° to 200° C., preferably 0° to 40° C.

Compounds of Formula II wherein $X_1$ is —S—CO—O—A—$R_1$ are obtainable, for example, by reacting the mercaptides II ($X_1$ = SNa) with chlorocarbonyloxy-fatty acid derivatives of the formula Cl—CO—O—A—$R_1$. When heated in a strongly acidic medium, e.g., with HCl in an inert solvent, e.g., THF, $CO_2$ is split off and the group —A—$R_1$ migrates to the sulfur atom.

Compounds of Formula II wherein $X_1$ is —S—$A_1$—COOH can be produced, for example, by thermal decomposition of correspondingly substituted oxalacetic acid dialkyl esters of Formula II ($X_1$ = —S—$A_1$—CO—COOR$_7$) or by the reaction of mercaptans of the Formula II ($X_1$ = SH) or the corresponding mercaptides with bromomalonic acid derivatives of the formula BrCR$_1$ ($C_pH_{2p+1}$)COOR$_7$ and respectively following partial or complete alkaline saponification. They can be decarboxylated to the compounds of Formula I as described in the literature, e.g., by dry heating or by warming in a solvent, e.g., water, hydrochloric acid, ethanol, dioxane, acetic acid or xylene, to a temperature of from about 50° to about 250° C. Suitably, the reaction mixture is heated until the evolution of carbon dioxide is terminated.

Azole derivatives of Formula I can also be obtained by acid cleavage of 3-keto-acid derivatives of Formula II ($X_1$ = —S—$A_1$—COR$_9$) in accordance with methods described in the literature. Keto esters of Formula II ($X_1$ = —S—$A_1$—COR$_{10}$, $R_1$ = esterified COOH-group) can be produced, for example, from the mercaptans II ($X_1$ = SH) with α-bromo-α-acetyl-fatty acid esters, e.g., bromoacetoacetic acid ethyl ester. The acid cleavage of the compounds II wherein $X_1$ is —S—$A_1$—COR$_{10}$ is effected by treatment with a strong base, e.g., NaOH, KOH or CA(OH)$_2$, in a solvent, e.g., water, methanol, ethanol, ether, THF, dioxane, benzene or a mixture thereof, at a temperature of about −10° to about 200° C. If the free carboxylic acids of Formula I ($R_1$ = COOH) are to be obtained, then the reaction mixture is preferably heated for several hours in an aqueous or aqueous-alcoholic solution, advantageously under an inert gas, such as nitrogen.

The compounds of Formula I can also be obtained by the cyclization of compounds of Formula III. These are N-(1,2-diaryl-2-oxoetyl)-carbamoylmercapto-fatty acids of the formula $R_3$—CO—CHR$_2$—NH—CO—S—A—COOH or N-(1,2-diaryl-2-oxoethyl)-amino-thiocarbonylmercapto-fatty acids of the formulae $R_3$—CO—CHR$_2$—NH—CS—S—A—COOH or (1,2-diaryl-2-oxoethoxy)-carbonimidoylmercapto-fatty acids of the formula $R_2$—CO—CHR$_3$—O—C—(=NH)—S—A—COOH or S-(1,2-diaryl-2-oxoethyl)-mercapto-carbonimidoylmercapto-fatty acids of the formula $R_2$—CO—CHR$_3$—S—C(=NH)—S—A—COOH or the corresponding (1,2-diaryl-1-thioxoethyl) compounds or functional derivatives of these substances. During the cyclization, one mol of water or hydrogen sulfide is split off.

The compounds of Formula III are normally not isolated. Instead, they preferably are produced as an intermediate in the reaction of 1,2-diaryl-2-haloethanones (preferably the corresponding chlorine or bromine compounds, e.g., desyl chloride or desyl bromide and the derivatives thereof substituted on the phenyl group) with carbomoylmercapto-fatty acid derivatives and/or aminothiocarbonylmercapto-fatty acid derivatives. Some of the latter starting compounds are known in the literature and are obtainable, for example, by the reaction of chlorocarbonylmercapto-fatty acid derivatives, e.g., chlorocarbonylmercaptoacetic acid ethyl ester, with ammonia and/or of ammonium dithiocarbamate with halo-fatty acid derivatives, e.g., the ethyl ester of bromoacetic acid. The compounds III are produced in situ in the presence or absence of one of the above-mentioned inert solvents, e.g., in the presence of a hydrocarbon, e.g, benzene or toluene, of an ether, e.g, THF or dioxane, or of an amide, e.g., DMF, or a mixture thereof. The reaction temperatures range normally from about 0° to about 200° C., preferably 20° to 150° C. In several cases, the cyclization of the intermediarily formed compounds III occurs under these conditions. In other cases, it is necessary or desirable to employ a second cyclizing stage and to add a cyclizing agent, e.g., a dehydration agent such as, for example, $POCl_3$, polyphosphoric acid, sulfuric acid or an agent which splits off hydrogen sulfide, e.g., HgO. A dicarbonyl compound III ($R_4$ = $R_3$—CO—CHR$_2$—NH—CO—) can be converted by reaction with $P_2S_5$, under the splitting off of one mol of water, into a thiazole derivative I (Z = S). It is possible to remove the solvent prior to this second cyclization stage and replace it, if desired, by another solvent. Suitable solvents for the cyclization stage include the aforementioned ones e.g., the hydrocarbons, for example, benzene or toluene. However, it is also possible and often advisable to conduct the subsequent cyclization in the absence of a solvent employing an excess of the cyclization agent. The cyclization is effected at a temperature of about 0° to about 200° C. and is terminated after about ½ to 48 hours.

Optionally, one or more of the $R_1$, $R_2$ and/or $R_3$ groups of a thus-obtained product of Formula I can, thereafter, if desired, be converted into another $R_1$, $R_2$ and/or $R_3$ group.

In particular, it is possible to convert an $R_1$ group into another $R_1$ group, for example, by treatment with a solvolyzing, thermolyzing, esterifying, ester-interchanging, amidating or dehydrating agent.

Functional derivaties of the carboxylic acids of Formula I, i.e., $R_1$ is other than COOH, can be solvolyzed, especially hydrolyzed, and/or thermolyzed to the free carboxylic acids in accordance with known methods described in the literature. Hydrolysis can be conducted in an acidic or alkaline medium at temperatures of about $-20°$ to about 200° C., preferably between room and boiling temperature of the selected solvent. Suitable acidic catalysts are for example, hydrochloric, sulfuric, phosphoric and hydrobromic acid. Suitable basic catalysts are, e.g., sodium, potassium or calcium hydroxide and sodium or potassium carbonate. Preferred solvents are water; lower alcohols; ethers, e.g., THF and dioxane; amides, e.g., DMF; sulfones, e.g., tetramethylenesulfone; and mixtures thereof, especially the water-containing mixtures. For saponification purposes, lower alkyl esters are preferably treated for about one hour to 48 hours with $K_2CO_3$ in methanol, ethanol or isopropanol at a temperature of about 20° to 80° C. In case an acidic saponificaton is conducted, aqueous acetic acid is likewise suitable as the solvent. Functional acid derivatives of Formula I can also be converted into the free carboxylic acids of Formula I ($R_1$ = COOH), for example, in ether or benzene, employing a strong base, e.g., potassium carbonate or in the absence of solvent, e.g., by melting with alkalis, for example, KOH and/or NaOH or alkaline earths.

In another embodiment of the invention, amides of Formula I ($R_1$ = $CONH_2$, $CONHR_7$, or $CONR_7R_8$) or thioamides of Formula I ($R_1$ = $CSNR_7R_8$) are saponified to a free acid of Formula I. The thioamides and/or amides are preferably hydrolyzed by heating with an aqueous mineral acid, e.g., hydrochloric acid.

By the heating, in the dry state, or particularly tertiary alkyl esters of the Formula I ($R_1$ = COO-tert.-alkyl) to temperatures of about 50° to 350° C., one also obtains acids of the Formula I ($R_1$ = COOH). The thermolysis can also be conducted in inert solvents, e.g., benzene, water, DMF, ethylene glycol, glycerin, dimethyl sulfoxide and cyclohexanol, preferably in the presence of a catalytic amount of an acid, e.g., p-toluenesulfonic acid.

In another embodiment of the invention, nitriles of Formula I ($R_1$ = CN) are hydrolyzed to a free acid of Formula I ($R_1$ = COOH), for example in an acidic medium, e.g., HCl in water, aqueous dioxane or acetic acid or in an alkaline medium, e.g, KOH in an aqueous lower alcohol or in cyclohexanol.

From other compounds of Formula I, esters of Formula I ($R_1$ = esterified carboxyl group) can be produced according to methods described in the literature. Thus, for example, an acid of Formula I ($R_1$ = COOH) can be esterified by reaction with the selected alcohol in the presence of an inorganic or organic acid as catalyst, HCl, HBr, HI, $H_2SO_4$, $H_3PO_4$, trifluoroacetic acid, benzenesulfonic acid or p-toluenesulfonic acid, or in the presence of an acidic ion exchanger, optionally in the presence of an inert solvent, e.g., benzene, toluene or xylene, at temperatures of about 0° C. to preferably the boiling temperature of the solvent. The alcohol is utilized preferably in molar excess. Preferred alcohols are those of the formulae $R_5OH$ and $R_6OH$ (wherein $R_5$ and $R_6$ have the values given above, except H). The reaction can be carried out in the presence of a water-binding agent, e.g., anhydrous heavy metal sulfates or molecular sieves. The water of reaction can also be removed azeotropically. In this procedure, a hydrocarbon, e.g., benzene or toluene, or a chlorinated hydrocarbon, e.g., chloroform or 1,2-dichloroethane, are advantageously added. The esterification takes place under gentle conditions if the water or reaction is bound chemically by the addition of a carbodiimide, e.g., N,N'-dicyclohexylcarbodiimide, employing an inert solvent, e.g., ether, dioxane, benzene and 1,2-dimethoxyethane and a base, e.g., pyridine. The methyl esters, e.g., methy ethyl and benzyl esters, can also be produced by reacting the free acids with diazomethane, diazoethane or phenyldiazomethane, in an inert solvent, e.g., ether, benzene or methanol. Esters of Formula I ($R_1$ = esterified COOH group) can also be obtained by chemically adding a carboxylic acid of formula I ($R_1$ = COOH) to an olefin, e.g., isobutylene or cyclohexene, or to an acetylene, preferably in the presence of a catalyst, e.g., $ZnCl_2$, $BF_3$, $H_2SO_4$, arylsulfonic acids, pyrophosphoric acid, boric acid and oxalic acid, at a temperature of about 0° to about 200° C., pressures of from 1 to 300 atmospheres, and in inert solvents, e.g., ether, THF, dioxane, benzene, toluene or xylene.

Esters of Formula I ($R_1$ = esterified COOH group) can also be prepared by the reaction of metallic salts of the carboxylic acids of Formula I ($R_1$ = COOH), preferably alkali metal, lead or silver salts, with alkyl halides, e.g., of the formula $R_5Cl$ or $R_6Cl$, optionally in an inert solvent, e.g., ether, benzene, DMF or petroleum ether, or with alkyl chlorosulfites, e.g., those of the formula $R_7OSOCl$, and subsequent thermolysis of the thus-obtained adducts.

It is likewise possible to convert acid halogenides, anhydrides, or nitriles of Formula I ($R_1$ = COCl, COBr, COOAcyl or CN) into esters of Formula I ($R_1$ = esterified COOH) by reaction with an alcohol, e.g., an alcohol of the formula $R_5OH$ or $R_6OH$, optionally in the presence of an acidic catalyst or a base, e.g., NaOH, KOH, $Na_2CO_3$, $K_2CO_3$ or pyridine. Preferably, an excess of the selected alcohol and temperatures of 0° to the boiling temperature are employed. Tert.-alkyl esters can be obtained, for example, from the acid chlorides and potassium tert.-alcoholate in the presence of an inert solvent.

Esters of Formula I ($R_1$ = esterified COOH group) can also be produced by the transesterification of other esters of Formula I ($R_1$ = $COOR_{11}$; $R_{11}$ = any desired organic residue, preferably $R_7$) with an excess of the selected alcohol, or by reacting the free carboxylic acids I ($R_1$ = COOH) with other esters of the selected alcohol, which are preferably employed in an excess. The transesterification methods described in the literature can be used, especially operating in the presence of basic or acidic catalysts, e.g., sodium ethylate or sulfuric acid, at temperatures of about 0° C. to preferably the boiling temperature.

Examples of the esters of Formula I ($R_1$ = esterified COOH) which can easily be split under physiological conditions are the vinyl, tert.-butyl, tetrahydro-2-furyl and tetrahydro-2-pyranyl esters obtainable, for instance, by reacting the free carboxylic acids with acetylene, isobutylene, 2,3-dihydrofuran, and 2,3-dihydropyran, in particular in the presence of a catalyst, e.g., $ZnCl_2$, $BF_3$, $H_2SO_4$, arylsulfonic acids, pyrophosphoric acid, boric acid or oxalic acid, at about 0°-120° C. in an inert solvent, e.g., ether, THF, dioxane, benzene or xylene.

Esters of Formula I ($R_1$ = esterified COOH) can also be obtained by solvolyzing compounds of Formula I wherein $R_1$ is a thioester, iminoether, oximinoether, hydrazone ether, thioamide, amidine, amidoxime or amide hydrazone group, with water or dilute aqueous bases or acids, e.g., ammonia, NaOH, KOH, $Na_2CO_3$, $K_2CO_3$, HCl or $H_2SO_4$, in the presence of the selected alcohol, with splitting off of hydrogen sulfide, ammonia, amines, hydrazine derivatives or hydroxylamine. Whereas most of the iminoether hydrochlorides in an aqueous solution are decomposed immediately at room temperature into esters and ammonium chlorides, the solvolysis of other derivatives, e.g., of some amidoximes or thioamides, requires temperatures of up to 100° C.

Acids of the Formula I ($R_1$ = COOH) can be converted, in the presence or absence of an inert solvent, into the corresponding acid halogenides I ($R_1$ = e.g., COCl or COBr) by treatment with inorganic acid halogenides, e.g., $SOCl_2$ or $SOBr_2$. Hydrochlorides of the iminoethers of Formula I ($R_1$ = C(=NH)$OR_7$) can be obtained from the nitriles of Formula I ($R_1$ = CN) with alcohols ($R_7OH$) in ether in the presence of HCl.

Acids of Formula I ($R_1$ = COOH) and/or the functional derivatives thereof, preferably their halogenides and esters (I, $R_1$ = COCl, COBr and/or esterified COOH group) can be converted into the corresponding amides by treatment with amidating agents, e.g., ammonia or amines of the formula $R_7NH_2$ or $R_7R_8NH$. Examples of suitable amines are monoalkylamines, e.g., methylamine, ethylamine, n-propylamine, isopropylamine, n-butylamine and isobutylamine; dialkylamines, e.g., dimethylamine, methylethylamine, diethylamine, di-n-propylamine, diisopropylamine, di-n-butylamine and diisobutylamine; aryl- and aralkylamines, e.g., aniline, benzylamine; hydroxyalkylamines, e.g., ethanolamine and diethanolamine; cyclic amines, e.g., pyrrolidine, piperidine, morpholine, thiomorpholine, piperazine and N-alkylpiperazines, e.g., N-methyl- or N-ethylpiperazine; N-hydroxyalkylpiperazines, e.g., N-2-hydroxyethylpiperazine. In the production of the amides, the use of an inert solvent, e.g., an alcohol, for example, methanol or ethanol, and the use of pressure, e.g., up to about 200 atmospheres, is possible but not required. The reaction temperatures range from about −20° to +100° C. preferably from 0° to 30° C.

Amides of Formula I ($R_1$ = $CONH_2$) can be dehydrated to the nitriles (I, $R_1$ = CN), for example, with a dehydrating agent such as $P_2O_5$, $POCl_3$ and p-toluenesulfochloride/pyridine, at temperatures of about 0° to 200 ° C., preferably 20 ° to 100 ° C.

One or both of the $R_2$ and $R_3$ groups of a thus-obtained product of Formula I can be converted into another $R_2$ $R_3$ group having a different value by substitution reactions and/or further conversions of the introduced or already present substituents.

For example, halogen atoms, nitro groups, sulfonic acid groups, etc., can be introduced into the aromatic rings by halogenation, nitration, sulfonation, etc. Amino groups can be diazotized and the thus-obtained diazonium groups can be further converted into other functional groups.

Thus, in accordance with methods described in the literature, one or more of the following substituents can be introduced into one or both of the aromatic nuclei, the number of substituents to be introduced being controlled by a suitable selection of the reaction conditions (amount of substitution agent, duration of reaction, reaction temperature, solvents, catalyst):

a. Chlorine

By the direct reaction with elemental chlorine in an inert solvent, e.g., water, ether, tetrachloromethane, acetic acid, without or with the addition or a catalyst, e.g., $FeCl_3$, $AlCl_3$, $SbCl_3$, or $SnCl_4$, preferably at −10° to 100° C.; or by reaction in a strongly hydrochloric acid solution with $H_2O_2$ or with $NaClO_3$, chlorination being effected by the chlorine produced in the nascent state; or by reaction with $SO_2Cl_2$ in an inert solvent, e.g., chlorobenzene, in the presence of a radical-forming catalyst, e.g., a peroxide, at a temperature of preferably 80°-180° C.; or other known methods.

b. Bromine

By direct reaction with elemental bromine in an inert solvent, e.g., carbon disulfide, acetic acid, chloroform, tetrachloromethane or dioxane, preferably in the presence of a catalyst acting as a bromine transfer agent, e.g., iron filings, $AlCl_3$, $AlBr_3$, $FeCl_3$, iodine or pyridine, preferably at −30° to 90° C.; or by reaction with hypobromous acid, an acyl hypobromite or N-bromoimide, e.g., N-bromosuccinimide, N-bromophthalimide or other bromine-yielding agent, e.g., 1,3-dibromo-5,5-dimethyl-hydantoin, in an inert solvent, e.g., nitrobenzene or carbon disulfide, preferably at −10° to 150° C.; or other known method.

c. Iodine

By the direct reaction with elemental iodine, preferably in the presence of HgO in an inert solvent, e.g., alcohol, acetic acid or benzene, preferably at a temperature of 0° to 120° C.; or by reaction with an iodine/alkali metal iodide solution in the presence of a carbonate, acetate or alkali metal hydroxide solution, ammonia or an amine; or by the reaction of a mixture of alkali metal iodide and an oxidizing agent, e.g., alkali metal iodates, alkali metal nitrates and $H_2O_2$, in an inert solvent, e.g., water, acetic acid and ethanol, the thus-liberated iodine reacting in the nascent state; or by reaction with ClI in dilute acetic acid, preferably at 50° to 100° C.; or mercuration, e.g., in an aqueous or acetic medium, with mercury (II) acetate to the Hg—O—$COCH_3$ compound followed by exchange of the organometal group with iodine, for example by reaction with iodine or an iodine/alkali metal hydroxide solution; or other known method.

d. Nitro

Nitration with one of the following: a mixture of anhydrous nitric acid and $BF_3$; a metal nitrate, e.g., Cu-, Fe-, Mn-, Co-, Ni-nitrate, in a mixture with acetic acid or acetic anhydride; a metal nitrate, e.g., Ag-, Ba-, Na-, K-, $NH_4$- or Pb-nitrate, in a mixture with a Friedel-Crafts catalyst, e.g., $AlCl_3$, $FeCl_3$, $BF_3$ or $SiCl_4$; an alkyl nitrate, e.g., ethyl nitrate, in a mixture with concentrated sulfuric acid, $HBF_4$ or a Lewis acid, e.g., $BCl_3$, $SNCl_4$, $PCl_3$, $AlCl_3$, $SiCl_4$, $SbCl_5$ or $FeCl_3$; nitryl fluoride, chloride, bromide, perchlorate or tetrafluoroborate, preferably in the presence of a Friedel-Crafts catalyst, e.g., $AlCl_3$, $FeCl_3$, $ZrCl_4$, or $AlBr_3$ in a solvent, e.g., carbon disulfide, n-pentane or $CHCl_3$; a nitrogen oxide, e.g., $N_2O_5$, $N_2O_4$, or $N_2O_3$, in the presence of concentrated $H_2SO_4$, HF or a Friedel-Crafts catalyst, e.g., $BF_3$, $AlCl_3$ or $FeCl_3$, optionally in a solvent, e.g., tetramethylenesulfone or acetic acid; concentrated nitric acid; a mixture of concentrated sulfuric acid with concentrated or anhydrous nitric acid; an alkali metal nitrate, e.g., sodium or potassium nitrate, in a mixture with concentrated sulfuric acid; a mixture of concentrated nitric acid with pyrosulfuric acid, fuming sulfuric acid, acetic acid and/or acetic anhydride; a mixture of nitric acid, sulfuric acid and acetic acid; acetyl nitrate or benzoyl nitrate; nitrosulfonic acid, which can be produced by the introduction of $SO_2$ into fuming $HNO_3$; nitrosylsulfuric acid; nitroguanidine; highly concentrated nitric acid in the presence of a dehydrating agent, e.g., $P_2O_5$ or anhydrous hydrofluoric acid, optionally in a solvent, e.g., nitrobenzene or polychloroethanes; or by dissolving the compound to be nitrated in a solvent, e.g., $CHCl_3$, $CH_2Cl_2$ or $CCl_4$, providing a bottom layer of concentrated sulfuric acid, and then adding thereto anhydrous nitric acid in $CHCl_3$, $CH_2Cl_2$ and/or $CCl_4$, this reaction generally being conducted at moderate temperatures, normally $-20°$ to $+50°$ C., preferably $-10°$ to $+20°$ C., in order to avoid secondary reactions; or other known method.

e. Alkyl, Alkylmercapto, Alkylsulfinyl, Alkylsulfonyl, Amino, Alkylamino or Dialkylamino By reaction with the corresponding chloro, bromo, iodo, hydroxy or acyloxy compound, e.g., ethyl iodide, n-propyl bromide, n-butanol, ethyl acetate, isopropyl sulfur chloride, isobutyl sulfinyl bromide, sec.-butyl sulfochloride, hydroxylamine, chloramine or diethyl chloramine, in accordance with the conditions of a Friedel-Crafts reaction, as described in greater detail in the literature. Suitable catalysts are Lewis acids, e.g., $AlCl_3$, $AlBr_3$, $SnCl_4$, $ZnCl_2$, $FeCl_3$, $SbCl_5$ and HF. Suitable solvents include n-hexane, carbon disulfide, nitrobenzene, tetramethylenesulfone and nitroethane. The reaction is preferably conducted at 70° to 180° C. In place of alkyl derivatives, it is also possible to employ the corresponding olefinic compounds in accordance with Friedel-Crafts.

f. Sulfo

By sulfonation with concentrated or fuming sulfuric acid or $SO_3$, e.g., in the form of the pyridine-$SO_3$ or dioxane-$SO_3$ complex, in the presence or absence of an additional inert solvent, e.g., dioxane, trichloroethylene or $CCl_4$, at about 0° to about 250° C.

In compounds of Formula I which contain a nitro group, the latter can be reduced to an amino group according to methods described in the literature, either catalytically or chemically.

Benzyl ether groups present in the compounds of Formula I can be split by hydrogenolysis.

For catalytic hydrogenations and/or hydrogenolyses, suitable catalysts include the nobel metal, nickel and cobalt catalysts. The noble metal catalysts can be present on supports, e.g., palladium on carbon, calcium carbonate or strontium carbonate, as oxide catalysts, e.g., platinum oxide, or as finely divided metallic catalysts. Nickel and cobalt catalysts are suitably utilized as Raney metals but nickel is also used on kieselguhr or pumice as the support. The hydrogention can be conducted at room temperature and under normal pressure or at an elevated temperature and/or elevated pressure. Preferably, the reaction is effected under pressure of from 1 to 100 atmos. and at temperatures of from $-80°$ to 200° C., especially from room temperature to $+100°$ C. The reaction is suitably conducted in the presence of a solvent, e.g., water, methanol, ethanol, isopropanol, n-butanol, ethyl acetate, dioxane, acetic acid, THF or a mixture thereof. During the hydrogenation and during the hydrogenolysis, normal pressure is preferably utilized and the reaction is terminated after the stoichiometric amount of hydrogen has been absorbed. Basically, it is possible to operate in the acidic, neutral or basic pH range.

The reaction with nascent hydrogen can be generally employed as a reducing method. The hydrogen can be produced, for example, by treatment of metals with acids or bases. Thus, it is possible, for example, to employ a mixture of zinc with acid or alkali solution, iron with hydrochoric acid or acetic acid or tin with hydrochloric acid. Also, an aluminum-nickel alloy can be utilized in an alkaline-aqueous solution, optionally in the presence of ethanol. Also suitable for the production of nascent hydrogen is sodium amalgam or aluminum amalgam in an aqueous-alcoholic or aqueous solution. The reaction can also be conducted in the heterogenous phase, wherein suitably an aqueous phase and a benzene or toluene phase are utilized. The reaction temperatures employed range from about room temperature to the boiling point of the solvent.

Also, suitable as reducing agents are complex metal hydrides, for example, sodium borohydride, e.g., in the presence of aluminum choride or lithium bromide, and also diborane. The reaction conditions must be selected so that the group $R_1$ remains intact. The procedure is advantageously conducted in the presence of an inert solvent, e.g., ether, tetrahydrofuran or ethylene glycol dimethyl ether. The reaction is advantageously terminated by boiling the reaction mixture. The thus-formed metal complexes can be decomposed in the usual manner, e.g., with an aqueous ammonium chloride solution.

Other suitable reducing agents are sodium dithionite in an alkaline or ammoniacal solution; iron(II) hydroxide; tin(II) chloride, particularly in an aqueous-hydrochloric medium at temperatures of about 0° to 60° C.; hydrogen sulfide, disulfides, sulfides and polysulfides; hydriodic acid; sodium sulfite; and hydrazine.

Chlorine, bromine or iodine atoms present in the $R_2$ and/or $R_3$ groups can be replaced by hydrogen, e.g., by converting the corresponding halogen compounds into the associated organometal, e.g., Grignard, compounds and hydrolyzing same with water or dilute acids.

Compounds of Formula I whose $R_2$ and/or $R_3$ groups contain free hydroxy, mercapto, amino or monoalkylamino groups can be alkylated to the corresponding alkoxy, alkylmercapto, monoalkylamino and dialkylamino compounds, or acylated to the corresponding acyloxy, acylmercapto and acylamido compounds. The alkylation can be carried out in accordance with methods set forth in the literature by treatment with an alkylating agent. For the O- and S- alkylation; the starting substances are suitably first converted into the corresponding salts by adding a base, e.g., NaOH. Usable alkylating agents are, for example, alkyl halogenides, e.g., methyl chloride, bromide or iodide, ethyl chloride, bromide or iodide, n-propyl chloride, bromide or iodide, isopropyl chloride, bromide or iodide, n-butyl chloride, bromide or iodide, or the corresponding dialkylsulfuric acid or alkylsulfonic acid esters, e.g., dimethyl sulfate, diethyl sulfate and methyl-p-toluenesulfonic acid ester. Diazo compounds, e.g., diazomethane, can also be utilized for the O- or S-alkylation. Amino compounds can also be alkylated with the corresponding alcohols, e.g., methanol ethanol, in the presence of Raney nickel, or reductively with formaldehyde or acetaldehyde in the presence of hydrogen or formic acid. If the reaction is conducted in the presence of hydrogen, the concomitant use of one of the above-mentioned catalysts is advantageous. Suitable solvents include water or an aqueous sodium hydroxide solution; alcohols, e.g., methanol, ethanol, n-butanol; hydrocarbons, e.g., benzene or xylene; ethers, e.g., THF; and mixtures thereof. The alkylation reactions take place advantageously at temperatures of about -10° to about +150° C., especially from room temperature to the boiling temperature of the reaction mixture. If a starting compound having a free carboxyl group ($R_1$ = COOH) is utilized, its carboxyl group can be simultaneously esterified unless the reaction mixture is maintained under strongly alkaline conditions.

An acylation takes place suitably with carboxylic acids or carboxylic acid derivatives. Examples of carboxylic acid derivatives are carboxylic acid esters, anhydrides, e.g., acetic anhydride, and halogenides, e.g., chlorides, bromides and iodides, e.g., acetyl chloride, bromide and iodide. An excess of the carboxylic acid derivative can be employed as the solvent or the reaction can be conducted in the presence of an inert solvent, e.g., benzene, toluene, THF, dioxane or chloroform. During the acylation, a base is preferably added, e.g., NaOH, KOH, sodium or potassium carbonate, pyridine or triethylamine.

In compounds of Formula I containing one or more diazonium groups, these groups can be exchanged, by literature methods, by fluoro, chloro, bromo, iodo, CN, $NO_2$, OH, SH, alkoxy or an alkylmercapto group. The diazonium compounds are obtainable in accordance with procedures described in the literature by the diazotization of the corresponding amino compounds, e.g., in a hydrochloric or hydrobromic aqueous solution by adding the stoichiometric quantity of an inorganic nitrite, preferably $NaNO_2$ or $KNO_2$, at a temperature of from about $-20°$ to $+10°$ C., or in an inert organic solvent, e.g., diethyl ether, diisopropyl ether, THF, dioxane, ethylene glycol dimethyl ether, ethylene glycol diethyl ether, diethylene glycol dimethyl ether or diethylene glycol diethyl ether, by adding an organic nitrite, e.g., n-butyl nitrite, n-amyl nitrite or isoamyl nitrite, at a temperature of from $-20°$ to $+5°$ C.

To introduce a fluorine atom, the diazotization is conducted, for example, in anhydrous hydrofluoric acid, and the reaction mixture is then heated, or the diazonium salt is converted with $HBF_4$ into a low-solubility diazonium tetrafluoroborate, which can be isolated and thermally converted into the desired fluorine compound, e.g., by heating in an inert solvent.

The diazonium group can be replaced by a chlorine atom, preferably in an aqueous solution in the presence of $Cu_2Cl_2$ according to the Sandmeyer method. The relacement by bromine can be carried out, for example, in an aqueous solution in the presence of $Cu_2Br_2$ according to Sandmeyer, or by reaction with bromine to obtain the diazonium perbromide and subsequent boiling in a solvent, e.g., water or a lower alkanol. It is also possible to convert the diazonium bromides into the diazonium mercury bromides with $HgBr_2$ and decompose these bromides thermally to the desired bromine compounds.

The replacement of a diazonium iodide substituent with an iodine atom can be accomplished by gentle heating. A catalyst, e.g., CuI, CuBr or CuCl, can also be added to the reaction medium in order to accelerate the reaction, as disclosed in the literature.

Furthermore, it is possible to convert a diazonium salt group into the corresponding alkoxy group for example by heating in an aqueous-alcoholic solution. The replacement with an alkyl-mercapto group by reaction with alkylmercaptans, is conducted, for example, in an alkaline solution, by heating or already in the cold state in the presence of a catalyst, e.g., powdered copper. The diazosulfides, formed as intermediates, need not be isolated.

By heating and if necessary by boiling, the aqueous solutions of the diazonium salts can also be hydrolyzed to the corresponding phenols. The reaction of the diazonium compounds with alkali metal salts of xanthic acid esters leads to the corresponding alkylxanthic derivatives, which can be hydrolyzed under alkaline conditions to the corresponding mercapto compounds.

A basic compound of Formula I, e.g., a compound substituted by at least one amino group, can be converted into the associated acid addition salt with the use of an acid. For this reaction, suitable acids are those yielding physiologically acceptable salts. Suitable acids are organic and inorganic acids, for example, aliphatic, alicyclic, araliphatic, aromatic and heterocyclic, mono- or polybasic carboxylic or sulfonic acids, e.g., formic acid, acetic acid, propionic acid, pivalic acid, diethylacetic acid, oxalic acid, malonic acid, succinic acid, pimelic acid, fumaric acid, maleic acid, lactic acid, tartaric acid, malic acid, aminocarboxylic acids, sulfamic acid, benzoic acid, salicylic acid, phenylpropionic acid, citric acid, gluconic acid, ascorbic acid, nicotinic acid, isonicotinic acid, methanesulfonic acid, ethanedisulfonic acid, $\beta$-hydroxyethanesulfonic acid, p-toluenesulfonic acid, naphthalene-mono- and -disulfonic acids, sulfuric acid, nitric acid, hydrohalic acids, e.g., hydrochloric acid and hydrobromic acid, and phosphoric acids, e.g., orthophosphoric acid.

Free carboxylic acids of Formula I ($R_1 =$ COOH) can be converted, by reaction with a base, into a physiologically acceptable metallic or ammonium salt thereof. Suitable salts are, in particular, the sodium, potassium, magnesium, calcium and ammonium salts. Others are substituted ammonium salts, e.g., the dimethyl- and diethylammonium, monoethanol-, diethanol-, and triethanolammonium, cyclohexylammonium, dicyclohexylammonium and dibenzylethylenediammonium salts.

Conversely, basic compounds of Formula I can be produced from the acid addition salts thereof by treatment with a strong base, e.g., sodium or potassium hydroxide or sodium or potassium carbonate, and acidic compounds of Formula I can be produced from the metal and ammonium salts thereof by treatment with an acid, especially mineral acids, e.g., hydrochloric or sulfuric acid. Compounds of Formula I containing both a basic and an acid group can be produced from their salts by appropriate ion exchange chromatography.

Compounds of Formula I which contain a center of asymmetry ordinarily are obtained in the racemic form. The racemates can be separated into their optical antipodes in accordance with a plurality of known methods as described in the literature. Chemical separation is preferred. According to this procedure, diastereomers are formed from the racemic mixture by reaction with an optically active auxiliary agent. Thus, an optically active base can be reacted with the carboxyl group, or an optically active acid with the amino group, of a compound of Formula I. For example, diastereomeric salts of the compounds of Formula I ($R_1 =$ COOH) can be formed with optically active amines, e.g., quinine, cinchonidine, brucine, cinchonine, hydroxyhydrindamine, morphine, 1-phenylethylamine, 1-naphthylethylamine, phenyloxy-naphthylmethylamine, quinidine and strychnine, basic amino acids, e.g., lysine, arginine and amino acid esters; or disatereomeric salts of basic compounds of Formula I can be formed with optically active acids, e.g., (+)- and (−)-tartaric acid, dibenzoyl-(+)- and -(−)-tartaric acid, diacetyl-(+)- and -(−)-tartaric acid, camphoric acid, $\beta$-camphorsulfonic acid, (+)- and (−)-mandelic acid, (+)- and (−)-malic acid, (+)- and (−)-2-phenylbutyric acid, (+) - and (−)-dinitrodiphenic acid, or (+)- and (−)-lactic acid. In a similar manner, ester diastereomers can be produced by the esterification of compounds of Formula I ($R_1$ = COOH) with optically active alcohols, e.g., borneol, menthol or 2-octanol. The thus-obtained mixtures of diastereomeric salts and/or esters can be separated by selective crystallization. The desired optically active compounds of Formula I can be produced by hydrolytic separation of the isolated diastereomeric compound.

Products of Formula I can be obtained as optically active compounds in accordance with the above-described methods by employing starting substances which are optically active.

The compounds of Formula I and/or optionally the physiologically acceptable salts thereof can be employed in a mixture with solid, liquid and/or semiliquid excipients as drugs in human or veterinary medicine. Suitable carrier compounds are those organic inorganic substances suitable for parenteral, enteral, or topical application, and which do not react with the novel compounds, such as, for example, water, vegetable oils, benzyl alcohols, polyethylene glycols, gelatin, lactose, amylose, magnesium stearate, talc, vaseline, cholesterol. For parenteral application, suitable are especially solutions, preferably oily or aqueous solutions, as well as suspensions, emulsions, or implants. For enteral application, tablets, dragees, capsules, syrups, elixirs and suppositories can be employed. For topical application, salves, creams and powders can be used. The aforementioned preparations can optionally be sterilized and/or can contain auxiliary agents, e.g., lubricants, preservatives, stabilizers and wetting agents, emulsifiers, salts for influencing the osmotic pressure, buffer substances, coloring, flavoring and/or aromatous agents.

The substances are preferably administered in dosages of from 10 to 2,000 mg. per dosage unit, preferably 100 to 500 mg. per dosage unit.

The temperatures herein are set forth in degrees Celsius. "Worked up as usual" means that, if necessary, water is added; the reaction mixture is extracted with ethyl acetate, ether or chloroform; separated; the organic extract washed with water, and dried over sodium sulfate; filtered; the solvent distilled off; and the residue distilled and/or crystallized from the solvent indicated in parentheses. DMF = dimethylformamide; THF = tetrahydrofuran.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the following Examples A and B, the preparation of some typical starting materials is described.

EXAMPLE A

A mixture of 20 g. of 4,5-diphenyl-2-oxazolone and 40 g. of $P_2S_5$ in 350 ml of xylene is refluxed for 12 hours with stirring. While still hot, the xylene solution is decanted from the residue and is cooled; 2-mercapto-4,5-diphenyl-oxazole precipitates; m.p. 252°–254°(from methanol).

EXAMPLE B

With stirring, 23 g. of desyl chloride (1-chloro-1,2-diphenyl-ethanone) are added in portions to a suspension of 16.5 g of ammonium dithiocarbamate in 100 ml of ethanol within 15 minutes. The mixture is stirred for 30 minutes and then warmed with stirring to 60°–65° for 2 additional hours. After cooling, water is added which causes 2-mercapto-4,5diphenyl-thiazole to precipitate; m.p. 219° (from acetone).

EXAMPLE 1 a. 12 g. of 2-mercapto-4,5-diphenyl-oxazole (m.p. 252°–254°, from methanol; obtainable from 4,5-diphenyl-2-oxazolone and phosphorus pentasulfide in boiling xylene, or by the reaction of benzoin with HSCN) is dissolved in 100 ml. of DMF, and 1.2 g. of NaH is added thereto. The reaction mixture is agitated for 1.5 hours at room temperature. Then, 5.6 ml. of the ethyl ester of bromoacetic acid in 20 ml. of DMF is added dropwise thereto, and the reaction mixture is stirred for 2 hours at 80°. The mixture is then mixed with water and worked up as usual, thus obtaining the ethyl ester of 4,5-diphenyl-2-oxazolyl-mercaptoacetic acid, b.p. 207°–210°/0.1mm.; m.p. 54°–56° (hexane).

Analogously, the following compounds are obtained from 2-mercapto-4,5-diphenyl-oxazole by reaction with the ethyl ester of respectively 2-bromopropionic acid; 2-bromobutyric acid; 2-bromoisobutyric acid; 3-bromopropionic acid; 4-bromobutyric acid; or 7-bromoheptanoic acid:

ethyl ester of 2-(4,5-diphenyl-2-oxazolyl-mercapto)-propionic acid,
ethyl ester of 2-(4,5-diphenyl-2-oxazolyl-mercapto)-butyric acid,
ethyl ester of 2-(4,5-diphenyl-2-oxazolyl-mercapto)-2-methylpropionic acid, b.p. 210°–215°/0.1 mm.,
ethyl ester of 3-(4,5-diphenyl-2-oxazolyl-mercapto)-propionic acid, m.p. 62°–64°,
ethyl ester of 4-(4,5-diphenyl-2-oxazolyl-mercapto)-butyric acid,
ethyl ester of 7-(4,5-diphenyl-2-oxazolyl-mercapto)-heptanoic acid.

Analogously, with the use of the following starting compounds:
2-mercapto-4-phenyl-5-p-tolyl-oxazole
2-mercapto-4-p-tolyl-5-phenyl-oxazole
2-mercapto-4,5-bis-p-tolyl-oxazole (m.p. 253°–255°)
2-mercapto-4,5-bis-p-isopropylphenyl-oxazole (m.p. 181°–183°)
2-mercapto-4-phenyl-5-o-fluorophenyl-oxazole
2-mercapto-4-phenyl-5-m-fluorophenyl-oxazole
2-mercapto-4-phenyl-5-p-fluorophenyl-oxazole
2-mercapto-4-o-fluorophenyl-5-phenyl-oxazole
2-mercapto-4-m-fluorophenyl-5-phenyl-oxazole
2-mercapto-4-p-fluorophenyl-5-phenyl-oxazole
2-mercapto-4,5-bis-o-fluorophenyl-oxazole
2-mercapto-4,5-bis-m-fluorophenyl-oxazole
2-mercapto-4,5-bis-p-fluorophenyl-oxazole
2-mercapto-4-p-tolyl-5-p-fluorophenyl-oxazole
2-mercapto-4-p-fluorophenyl-5-p-tolyl-oxazole
2-mercapto-4-phenyl-5-o-chlorophenyl-oxazole
2-mercapto-4-phenyl-5-m-chlorophenyl-oxazole
2-mercapto-4-phenyl-5-p-chlorophenyl-oxazole
2-mercapto-4-o-chlorophenyl-5-phenyl-oxazole
2-mercapto-4-m-chlorophenyl-5-phenyl-oxazole
2-mercapto-4-p-chlorophenyl-5-phenyl-oxazole
2-mercapto-4,5-bis-o-chlorophenyl-oxazole (m.p. 208°–210°)
2-mercapto-4,5-bis-m-chlorophenyl-oxazole
2-mercapto-4,5-bis-p-chlorophenyl-oxazole (m.p. 229°–232°; obtainable from 4,5-bis-p-chlorophenyl-oxazolone and $P_2S_5$, or from 4,4'-dichlorobenzoin and HSCN)

2-mercapto-4-p-tolyl-5-p-chlorophenyl-oxazole
2-mercapto-4-p-chlorophenyl-5-p-tolyl-oxazole
2-mercapto-4-p-fluorophenyl-5-p-chlorophenyl-oxazole
2-mercapto-4-p-chlorophenyl-5-p-fluorophenyl-oxazole
2-mercapto-4-phenyl-5-o-bromophenyl-oxazole
2-mercapto-4-phenyl-5-m-bromophenyl-oxazole
2-mercapto-4-phenyl-5-p-bromophenyl-oxazole
2-mercapto-4-o-bromophenyl-5-phenyl-oxazole
2-mercapto-4-m-bromophenyl-5-phenyl-oxazole
2-mercapto-4-p-bromophenyl-5-phenyl-oxazole
2-mercapto-4,5-bis-o-bromophenyl-oxazole
2-mercapto-4,5-bis-m-bromophenyl-oxazole
2-mercapto-4,5-bis-p-bromophenyl-oxazole
2-mercapto-4-p-tolyl-5-p-bromophenyl-oxazole
2-mercapto-4-p-bromophenyl-5-p-tolyl-oxazole
2-mercapto-4-p-chlorophenyl-5-p-bromophenyl-oxazole
2-mercapto-4-p-bromophenyl-5-p-chlorophenyl-oxazole
2-mercapto-4-phenyl-5-p-iodophenyl-oxazole
2-mercapto-4-p-iodophenyl-5-phenyl-oxazole
2-mercapto-4,5-bis-p-iodophenyl-oxazole
2-mercapto-4-phenyl-5-p-trifluoromethylphenyl-oxazole
2-mercapto-4-p-trifluoromethylphenyl-5-phenyl-oxazole
2-mercapto-4,5-bis-p-trifluoromethylphenyl-oxazole
2-mercapto-4-p-trifluoromethylphenyl-5-p-chlorophenyl-oxazole
2-mercapto-4-p-chlorophenyl-5-p-trifluoromethylphenyl-oxazole
2-mercapto-4-phenyl-5-p-hydroxyphenyl-oxazole
2-mercapto-4-p-hydroxyphenyl-5-phenyl-oxazole
2-mercapto-4,5-bis-p-hydroxyphenyl-oxazole
2-mercapto-4-p-chlorophenyl-5-p-hydroxyphenyl-oxazole
2-mercapto-4-p-hydroxyphenyl-5-p-chlorophenyl-oxazole
2-mercapto-4-phenyl-5-o-methoxyphenyl-oxazole
2-mercapto-4-phenyl-5-m-methoxyphenyl-oxazole
2-mercapto-4-phenyl-5-p-methoxyphenyl-oxazole
2-mercapto-4-o-methoxyphenyl-5-phenyl-oxazole
2-mercapto-4-m-methoxyphenyl-5-phenyl-oxazole
2-mercapto-4-p-methoxyphenyl-5-phenyl-oxazole (m.p. 170°–171°)
2-mercapto-4,5-bis-o-methoxyphenyl-oxazole
2-mercapto-4,5-bis-m-methoxyphenyl-oxazole (m.p. 182°–184°)
2-mercapto-4,5-bis-p-methoxyphenyl-oxazole (m.p. 202°–203°)
2-mercapto-4-p-chlorophenyl-5-p-methoxyphenyl-oxazole
2-mercapto-4-p-methoxyphenyl-5-o-chlorophenyl-oxazole (m.p. 220°–222°)
2-mercapto-4-p-methoxyphenyl-5-m-chlorophenyl-oxazole
2-mercapto-4-p-methoxyphenyl-5-p-chlorophenyl-oxazole
2-mercapto-4-phenyl-5-(3,4-dimethoxyphenyl)-oxazole
2-mercapto-4-(3,4-dimethoxyphenyl)-5-phenyl-oxazole
2-mercapto-4,5-bis-(3,4-dimethoxyphenyl)-oxazole (m.p. 175°–177°)
2-mercapto-4-p-chlorophenyl-5-(3,4-dimethoxyphenyl)-oxazole
2-mercapto-4-(3,4-dimethoxyphenyl)-5-p-chlorophenyl-oxazole
2-mercapto-4-phenyl-5-(3,4-methylenedioxyphenyl)-oxazole
2-mercapto-4-(3,4-methylenedioxyphenyl)-5-phenyl-oxazole
2-mercapto-4,5-bis-(3,4-methylenedioxyphenyl)-oxazole (m.p. 261°–263°)
2-mercapto-4-p-chlorophenyl-5-(3,4-methylenedioxyphenyl)-oxazole
2-mercapto-4-(3,4-methylenedioxyphenyl)-5-o-chlorophenyl-oxazole
2-mercapto-4-(3,4-methylenedioxyphenyl)-5-m-chlorophenyl-oxazole
2-mercapto-4-(3,4-methylenedioxyphenyl)-5-p-chlorophenyl-oxazole (m.p. 258°–260°)
2-mercapto-4-phenyl-5-p-methylmercaptophenyl-oxazole
2-mercapto-4-p-methylmercaptophenyl-5-phenyl-oxazole
2-mercapto-4,5-bis-p-methylmercaptophenyl-oxazole
2-mercapto-4-p-chlorophenyl-5-p-methylmercaptophenyl-oxazole
2-mercapto-4-p-methylmercaptophenyl-5-p-chlorophenyl-oxazole
2-mercapto-4-phenyl-5-p-dimethylaminophenyl-oxazole
2-mercapto-4-p-dimethylaminophenyl-5-phenyl-oxazole (m.p. 205°–209°)
2-mercapto-4,5-bis-p-dimethylaminophenyl-oxazole
2-mercapto-4-p-chlorophenyl-5-p-dimethylaminophenyl-oxazole
2-mercapto-4-p-dimethylaminophenyl-5-o-chlorophenyl-oxazole (m.p. 229°–231°)
2-mercapto-4-p-dimethylaminophenyl-5-m-chlorophenyl-oxazole
2-mercapto-4-p-dimethylaminophenyl-5-p-chlorophenyl-oxazole (m.p. 254°–256°)
2-mercapto-4-phenyl-5-p-nitrophenyl-oxazole
2-mercapto-4-p-nitrophenyl-5-phenyl-oxazole
2-mercapto-4,5-bis-p-nitrophenyl-oxazole
2-mercapto-4-p-chlorophenyl-5-p-nitrophenyl-oxazole
2-mercapto-4-p-nitrophenyl-5-p-chlorophenyl-oxazole
2-mercapto-4-phenyl-5-p-aminophenyl-oxazole
2-mercapto-4-p-aminophenyl-5-phenyl-oxazole
2-mercapto-4,5-bis-p-aminophenyl-oxazole
2-mercapto-4-p-chlorophenyl-5-p-aminophenyl-oxazole
2-mercapto-4-p-aminophenyl-5-p-chlorophenyl-oxazole
the corresponding 4,5-diaryl-2-oxazolyl-mercapto-fatty acid derivatives are obtained by reaction with the corresponding halo-fatty acid derivatives, for example:
the ethyl esters of each of the following acids:
4-phenyl-5-p-tolyl-2-oxazolyl-mercaptoacetic acid
4-p-tolyl-5-phenyl-2-oxazolyl-mercaptoacetic acid
4,5-bis-p-tolyl-2-oxazolyl-mercaptoacetic acid, m.p. of this ethyl ester: 106°–108°
2-(4,5-bis-p-tolyl-2-oxazolyl-mercapto)-butyric acid
4,5-bis-p-isopropylphenyl-2-oxazolyl-mercaptoacetic acid
4-phenyl-5-o-fluorophenyl-2-oxazolyl-mercaptoacetic acid
4-phenyl-5-m-fluorophenyl-2-oxazolyl-mercaptoacetic acid
4-phenyl-5-p-fluorophenyl-2-oxazolyl-mercaptoacetic acid
4-o-fluorophenyl-5-phenyl-2-oxazolyl-mercaptoacetic acid
4-m-fluorophenyl-5-phenyl-2-oxazolyl-mercaptoacetic acid
4-p-fluorophenyl-5-phenyl-2-oxazolyl-mercaptoacetic acid
4,5-bis-o-fluorophenyl-2-oxazolyl-mercaptoacetic acid 4,5-bis-m-fluorophenyl-2-oxazolyl-mercaptoacetic acid
4,5-bis-p-fluorophenyl-2-oxazolyl-mercaptoacetic acid
4-p-tolyl-5-p-fluorophenyl-2-oxazolyl-mercaptoacetic acid
4-p-fluorophenyl-5-p-tolyl-2-oxazolyl-mercaptoacetic acid
4-phenyl-5-o-chlorophenyl-2-oxazolyl-mercaptoacetic acid
4-phenyl-5-m-chlorophenyl-2-oxazolyl-mercaptoacetic acid
4-phenyl-5-p-chlorophenyl-2-oxazolyl-mercaptoacetic acid
4-o-chlorophenyl-5-phenyl-2-oxazolyl-mercaptoacetic acid
4-m-chlorophenyl-5-phenyl-2-oxazolyl-mercaptoacetic acid
4-p-chlorophenyl-5-phenyl-2-oxazolyl-mercaptoacetic acid
4,5-bis-o-chalorophenyl-2-oxazolyl-mercaptoacetic acid
4,5-bis-m-chlorophenyl-2-oxazolyl-mercaptoacetic acid
4,5-bis-p-chlorophenyl-2-oxazolyl-mercaptoacetic acid, m.p. of this ethyl ester: 122°–124°
2-(4,5-bis-p-chlorophenyl-2-oxazolyl-mercapto)-propionic acid
3-(4,5-bis-p-chlorophenyl-2-oxazolyl-mercapto)-propionic acid, m.p. of this ethyl ester: 85°–87°
2-(4,5-bis-p-chlorophenyl-2-oxazolyl-mercapto)-butyric acid, m.p. of this ethyl ester: 98°–99°
4-p-tolyl-5-p-chlorophenyl-2-oxazolyl-mercaptoacetic acid
4-p-chlorophenyl-5-p-tolyl-2-oxazolyl-mercaptoacetic acid
4-p-fluorophenyl-5-p-chlorophenyl-2-oxazolyl-mercaptoacetic acid
4-p-chlorophenyl-5-p-fluorophenyl-2-oxazolyl-mercaptoacetic acid
4-phenyl-5-o-bromophenyl-2-oxazolyl-mercaptoacetic acid
4-phenyl-5-m-bromophenyl-2-oxazolyl-mercaptoacetic acid
4-phenyl-5-p-bromophenyl-2-oxazolyl-mercaptoacetic acid
4-o-bromophenyl-5-phenyl-2-oxazolyl-mercaptoacetic acid
4-m-bromophenyl-5-phenyl-2-oxazolyl-mercaptoacetic acid
4-p-bromophenyl-5-phenyl-2-oxazolyl-mercaptoacetic acid
4,5-bis-o-bromophenyl-2-oxazolyl-mercaptoacetic acid
4,5-bis-m-bromophenyl-2-oxazolyl-mercaptoacetic acid
4,5-bis-p-bromophenyl-2-oxazolyl-mercaptoacetic acid
4-p-tolyl-5-p-bromophenyl-2-oxazolyl-mercaptoacetic acid
4-p-bromophenyl-5-p-tolyl-2-oxazolyl-mercaptoacetic acid
4-p-chlorophenyl-5-p-bromophenyl-2-oxazolyl-mercaptoacetic acid
4-p-bromophenyl-5-p-chlorophenyl-2-oxazolyl-mercaptoacetic acid
4-phenyl-5-p-iodophenyl-2-oxazolyl-mercaptoacetic acid
4-p-iodophenyl-5-phenyl-2-oxazolyl-mercaptoacetic acid
4,5-bis-p-iodophenyl-2-oxazolyl-mercaptoacetic acid
4-phenyl-5-p-trifluoromethylphenyl-2-oxazolyl-mercaptoacetic acid
4-p-trifluoromethylphenyl-5-phenyl-2-oxazolyl-mercaptoacetic acid
4,5-bis-p-trifluoromethylphenyl-2-oxazolyl-mercaptoacetic acid
4-p-trifluoromethylphenyl-5-p-chlorophenyl-2-oxazolyl-mercaptoacetic acid
4-p-chlorophenyl-5-p-trifluoromethylphenyl-2-oxazolyl-mercaptoacetic acid
4-phenyl-5-p-hydroxyphenyl-2-oxazolyl-mercaptoacetic acid
4-p-hydroxyphenyl-5-phenyl-2-oxazolyl-mercaptoacetic acid
4,5-bis-p-hydroxyphenyl-2-oxazolyl-mercaptoacetic acid
4-p-chlorophenyl-5-p-hydroxyphenyl-2-oxazolyl-mercaptoacetic acid
4-p-hydroxyphenyl-5-p-chlorophenyl-2-oxazolyl-mercaptoacetic acid
4-phenyl-5-o-methoxyphenyl-2-oxazolyl-mercaptoacetic acid
4-phenyl-5-m-methoxyphenyl-2-oxazolyl-mercaptoacetic acid
4-phenyl-5-p-methoxyphenyl-2-oxazolyl-mercaptoacetic acid
4-o-methoxyphenyl-5-phenyl-2-oxazolyl-mercaptoacetic acid
4-m-methoxyphenyl-5-phenyl-2-oxazolyl-mercaptoacetic acid
4-p-methoxyphenyl-5-phenyl-2-oxazolyl-mercaptoacetic acid
4,5-bis-o-methoxyphenyl-2-oxazolyl-mercaptoacetic acid
4,5-bis-m-methoxyphenyl-2-oxazolyl-mercaptoacetic acid
4,5-bis-p-methoxyphenyl-2-oxazolyl-mercaptoacetic acid, m.p. of this ethyl ester: 76°
2-(4,5-bis-p-methoxyphenyl-2-oxazolyl-mercapto)-butyric acid
4-p-chlorophenyl-5-p-methoxyphenyl-2-oxazolyl-mercaptoacetic acid
4-p-methoxyphenyl-5-o-chlorophenyl-2-oxazolyl-mercaptoacetic acid
4-p-methoxyphenyl-5-m-chlorophenyl-2-oxazolyl-mercaptoacetic acid
4-p-methoxyphenyl-5-p-chlorophenyl-2-oxazolyl-mercaptoacetic acid
4-phenyl-5-(3,4-dimethoxyphenyl)-2-oxazolyl-mercaptoacetic acid
4-(3,4-dimethoxyphenyl)-5-phenyl-2-oxazolyl-mercaptoacetic acid
4,5-bis-(3,4-dimethoxyphenyl)-2-oxazolyl-mercaptoacetic acid, m.p. of this ethyl ester: 103–105°
4-p-chlorophenyl-5-(3,4-dimethoxyphenyl)-2-oxazolyl-mercaptoacetic acid
4-(3,4-dimethoxyphenyl)-5-p-chlorophenyl-2-oxazolyl-mercaptoacetic acid
4-phenyl-5-(3,4-methylenedioxyphenyl)-2-oxazolyl-mercaptoacetic acid
4-(3,4-methylenedioxyphenyl)-5-phenyl-2-oxazolyl-mercaptoacetic acid
4,5-bis-(3,4-methylenedioxyphenyl)-2-oxazolyl-mercaptoacetic acid, m.p. of this ethyl ester: 93–95°
4-p-chlorophenyl-5-(3,4-methylenedioxyphenyl)-2-oxazolyl-mercaptoacetic acid
4-(3,4-methylenedioxyphenyl)-5-o-chlorophenyl-2-oxazolyl-mercaptoacetic acid
4-(3,4-methylenedioxyphenyl)-5-m-chlorophenyl-2-oxazolyl-mercaptoacetic acid 4-(3,4-methylenedioxyphenyl)-5-p-chlorophenyl-2-oxazolyl-mercaptoacetic acid, m.p. of this ethyl ester: 118-120°
4-phenyl-5-p-methylmercaptophenyl-2-oxazolyl-mercaptoacetic acid
4-p-methylmercaptophenyl-5-phenyl-2-oxazoly-mercaptoacetic acid
4,5-bis-p-methylmercaptophenyl-2-oxazolyl-mercaptoacetic acid
4-p-chlorophenyl-5-p-methylmercaptophenyl-2-oxazolyl-mercaptoacetic acid
4-p-methylmercaptophenyl-5-p-chlorophenyl-2-oxazolyl-mercaptoacetic acid
4-phenyl-5-p-dimethylaminophenyl-2-oxazolyl-mercaptoacetic acid
4-p-dimethylaminophenyl-5-phenyl-2-oxazolyl-mercaptoacetic acid
4,5-bis-p-dimethylaminophenyl-2-oxazolyl-mercaptoacetic acid
4-p-chlorophenyl-5-p-dimethylaminophenyl-2-oxazolyl-mercaptoacetic acid
4-p-dimethylaminophenyl-5-o-chlorophenyl-2-oxazolyl-mercaptoacetic acid, m.p. of this ethyl ester: 95-97°
4-p-dimethylaminophenyl-5-m-chlorophenyl-2-oxazolyl-mercaptoacetic acid
4-p-dimethylaminophenyl-5-p-chlorophenyl-2-oxazolyl-mercaptoacetic acid, m.p. of this ehtyl ester: 106-107°
4-phenyl-5-p-nitrophenyl-2-oxazolyl-mercaptoacetic acid
4-p-nitrophenyl-5-phenyl-2-oxazolyl-mercaptoacetic acid
4,5-bis-p-nitrophenyl-2-oxazolyl-mercaptoacetic acid
4-p-chlorophenyl-5-p-nitrophenyl-2-oxazolyl-mercaptoacetic acid
4-p-nitrophenyl-5-p-chlorophenyl-2-oxazolyl-mercaptoacetic acid
4-phenyl-5-p-aminophenyl-2-oxazolyl-mercaptoacetic acid
4-p-aminophenyl-5-phenyl-2-oxazolyl-mercaptoacetic acid
4,5-bis-p-aminophenyl-2-oxazolyl-mercaptoacetic acid
4-p-chlorophenyl-5-p-aminophenyl-2-oxazolyl-mercaptoacetic acid
4-p-aminophenyl-5-p-chlorophenyl-2-oxazolyl-mercaptoacetic acid.

b. 19.5 g. of the ethyl ester of 4,5-diphenyl-2-oxazolyl-mercaptoacetic acid is refluxed in 200 ml. of ethanol with 25 g. of pulverized potassium carbonate for 2 hours under agitation. The reaction mixture is concentrated by evaporation, the residue is mixed with water, and the aqueous phase is extracted with ether. Then, the mixture is adjusted to a pH of 6 with hydrochloric acid, worked up as usual, and the compound thus obtained is 4,5-diphenyl-2-oxazolyl-mercaptoacetic acid, m.p. 137°-138° (hexane/ethyl acetate); sodium salt, m.p. 270°-272°.

Analogously, by saponifying the corresponding esters, the following compounds are produced
2-(4,5-diphenyl-2-oxazolyl-mercapto)-propionic acid (m.p. 89°-91°)
2-(4,5-diphenyl-2-oxazolyl-mercapto)-butyric acid (m.p. 123°-124°)
2-(4,5-diphenyl-2-oxazolyl-mercapto)-2-methylpropionic acid (m.p. 118°-120°)
3-(4,5-diphenyl-2-oxazolyl-mercapto)-propionic acid (m.p. 135°-137°)
4-(4,5-diphenyl-2-oxazolyl-mercapto)-butyric acid (m.p. 94°-96°)
7-(4,5-diphenyl-2-oxazolyl-mercapto)-heptanoic acid (m.p. 68°)
4-phenyl-5-p-tolyl-2-oxazolyl-mercaptoacetic acid
4-p-tolyl-5-phenyl-2-oxazolyl-mercaptoacetic acid
4,5-bis-p-tolyl-2-oxazolyl-mercaptoacetic acid (m.p. 142°-144°)
2-(4,5-bis-p-tolyl-2-oxazolyl-mercapto)-butyric acid
4,5-bis-p-isopropylphenyl-2-oxazolyl-mercaptoacetic acid (m.p. 76°-78°)
4-phenyl-5-o-fluorophenyl-2-oxazolyl-mercaptoacetic acid
4-phenyl-5-m-fluorophenyl-2-oxazolyl-mercaptoacetic acid
4-phenyl-5-p-fluorophenyl-2-oxazolyl-mercaptoacetic acid
4-o-fluorophenyl-5-phenyl-2-oxazolyl-mercaptoacetic acid
4-m-fluorophenyl-5-phenyl-2-oxazolyl-mercaptoacetic acid
4-p-fluorophenyl-5-phenyl-2-oxazolyl-mercaptoacetic acid
4,5-bis-o-fluorophenyl-2-oxazolyl-mercaptoacetic acid
4,5-bis-m-fluorophenyl-2-oxazolyl-mercaptoacetic acid
4,5-bis-p-fluorophenyl-2-oxazolyl-mercaptoacetic acid
4-p-tolyl-5-p-fluorophenyl-2-oxazolyl-mercaptoacetic acid
4-p-fluorophenyl-5-p-tolyl-2-oxazolyl-mercaptoacetic acid
4-phenyl-5-o-chlorophenyl-2-oxazolyl-mercaptoacetic acid
4-phenyl-5-m-chlorophenyl-2-oxazolyl-mercaptoacetic acid
4-phenyl-5-p-chlorophenyl-2-oxazolyl-mercaptoacetic acid
4-o-chlorophenyl-5-phenyl-2-oxazolyl-mercaptoacetic acid
4-m-chlorophenyl-5-phenyl-2-oxazolyl-mercaptoacetic acid
4-p-chlorophenyl-5-phenyl-2-oxazolyl-mercaptoacetic acid
4,5-bis-o-chlorophenyl-2-oxazolyl-mercaptoacetic acid (m.p. 97°-99°)
4,5-bis-m-chlorophenyl-2-oxazolyl-mercaptoacetic acid (m.p. 114°-115°)
4,5-bis-p-chlorophenyl-2-oxazolyl-mercaptoacetic acid (m.p. 151°-153°)
2-(4,5-bis-p-chlorophenyl-2-oxazolyl-mercaptopropionic acid (m.p. 138°-140°)
3-(4,5-bis-p-chlorophenyl-2-oxazolyl-mercapto)-propionic acid
2-(4,5-bis-p-chlorophenyl-2-oxazolyl-mercapto)-butyric acid (m.p. 130°-132°)
4-p-tolyl-5-p-chlorophenyl-2-oxazolyl-mercaptoacetic acid
4-p-chlorophenyl-5-p-tolyl-2-oxazolyl-mercaptoacetic acid
4-p-fluorophenyl-5-p-chlorophenyl-2-oxazolyl-mercaptoacetic acid
4-p-chlorophenyl-5-p-fluorophenyl-2-oxazolyl-mercaptoacetic acid
4-phenyl-5o-bromophenyl-2-oxazolyl-mercaptoacetic acid
4-phenyl-5-m-bromophenyl-2-oxazolyl-mercaptoacetic acid
4-phenyl-5-p-bromophenyl-2-oxazolyl-mercaptoacetic acid 4-o-bromophenyl-5-phenyl-2-oxazolyl-mercaptoacetic acid
4-m-bromophenyl-5-phenyl-2-oxazolyl-mercaptoacetic acid
4-p-bromophenyl-5-phenyl-2-oxazolyl-mercaptoacetic acid
4,5-bis-o-bromophenyl-2-oxazolyl-mercaptoacetic acid
4,5-bis-m-bromophenyl-2-oxazolyl-mercaptoacetic acid
4,5-bis-p-bromophenyl-2-oxazolyl-mercaptoacetic acid (m.p. 168°–170°)
4-p-tolyl-5-p-bromophenyl-2-oxazolyl-mercaptoacetic acid
4-p-bromophenyl-5-p-tolyl-2-oxazolyl-mercaptoacetic acid
4-p-chlorophenyl-5-p-bromophenyl-2-oxazolyl-mercaptoacetic acid
4-p-bromophenyl-5-p-chlorophenyl-2-oxazolyl-mercaptoacetic acid
4-phenyl-5-p-iodophenyl-2-oxazolyl-mercaptoacetic acid
4-p-iodophenyl-5-phenyl-2-oxazolyl-mercaptoacetic acid
4,5-bis-p-iodophenyl-2-oxazolyl-mercaptoacetic acid
4-phenyl-5-p-trifluoromethylphenyl-2-oxazolyl-mercaptoacetic acid
4-p-trifluoromethylphenyl-5-phenyl-2-oxazolyl-mercaptoacetic acid
4,5-bis-p-trifluoromethylphenyl-2-oxazolyl-mercaptoacetic acid
4-p-trifluoromethylphenyl-5-p-chlorophenyl-2-oxazolyl-mercaptoacetic acid
4-p-chlorophenyl-5-p-trifluoromethylphenyl-2-oxazolyl-mercaptoacetic acid
4-phenyl-5-p-hydroxyphenyl-2-oxazolyl-mercaptoacetic acid
4-p-hydroxyphenyl-5-phenyl-2-oxazolyl-mercaptoacetic acid
4,5-bis-p-hydroxyphenyl-2-oxazolyl-mercaptoacetic acid
4-p-chlorophenyl-5-p-hydroxyphenyl-2-oxazolyl-mercaptoacetic acid
4-p-hydroxyphenyl-5-p-chlorophenyl-2-oxazolyl-mercaptoacetic acid
4-phenyl-5-o-methoxyphenyl-2-oxazolyl-mercaptoacetic acid
4-phenyl-5-m-methoxyphenyl-2-oxazolyl-mercaptoacetic acid
4-phenyl-5-p-methoxyphenyl-2-oxazolyl-mercaptoacetic acid
4-o-methoxyphenyl-5-phenyl-2-oxazolyl-mercaptoacetic acid
4-m-methoxyphenyl-5-phenyl-2-oxazolyl-mercaptoacetic acid
4-p-methoxyphenyl-5-phenyl-2-oxazolyl-mercaptoacetic acid (m.p. 152°–154°)
4,5-bis-o-methoxyphenyl-2-oxazolyl-mercaptoacetic acid (m.p. 110°–112°)
4,5-bis-m-methoxyphenyl-2-oxazolyl-mercaptoacetic acid, cyclohexylamine salt, m.p. 95°–98°
4,5-bis-p-methoxyphenyl-2-oxazolyl-mercaptoacetic acid (m.p. 140°–141°)
2-(4,5-bis-p-methoxyphenyl-2-oxazolyl-mercapto)-butyric acid
4-p-chlorophenyl-5-p-methoxyphenyl-2-oxazolyl-mercaptoacetic acid
4-p-methoxyphenyl-5-o-chlorophenyl-2-oxazolyl-mercaptoacetic acid (m.p. 135°–137°)
4-p-methoxyphenyl-5-m-chlorophenyl-2-oxazolyl-mercaptoacetic acid
4-p-methoxyphenyl-5-p-chlorophenyl-2-oxazolyl-mercaptoacetic acid
4-phenyl-5-(3,4-dimethoxyphenyl)-2-oxazolyl-mercaptoacetic acid
4-(3,4-dimethoxyphenyl)-5-phenyl-2-oxazolyl-mercaptoacetic acid
4,5-bis-3,4-dimethoxyphenyl)-2-oxazolyl-mercaptoacetic acid (m.p. 118°–120°)
4-p-chlorophenyl-5-(3,4-dimethoxyphenyl)-2-oxazolyl-mercaptoacetic acid
4-(3,4-dimethoxyphenyl)-5-p-chlorophenyl-2-oxazolyl-mercaptoacetic acid
4-phenyl-5-(3,4-methylenedioxyphenyl)-2-oxazolyl-mercaptoacetic acid
4-(3,4-methylenedioxyphenyl)-5-phenyl-2-oxazolyl-mercaptoacetic acid
4,5-bis-(3,4-methylenedioxyphenyl)-2-oxazolyl-mercaptoacetic acid (m.p. 143°–145°)
4-p-chlorophenyl-5-(3,4-methylenedioxyphenyl)-2-oxazolyl-mercaptoacetic acid
4-(3,4-methylenedioxyphenyl)-5-o-chlorophenyl-2-oxazolyl-mercaptoacetic acid
4-(3,4-methylenedioxyphenyl)-5-m-chlorophenyl-2-oxazolyl-mercaptoacetic acid
4-(3,4-methylenedioxyphenyl)-5-p-chlorophenyl-2-oxazolyl-mercaptoacetic acid
4-phenyl-5-p-methylmercaptophenyl-2-oxazolyl-mercaptoacetic acid
4-p-methylmercaptophenyl-5-phenyl-2-oxazolyl-mercaptoacetic acid
4,5-bis-p-methylmercaptophenyl-2-oxazolyl-mercaptoacetic acid
4-p-chlorophenyl-5-p-methylmercaptophenyl-2-oxazolyl-mercaptoacetic acid
4-p-methylmercaptophenyl-5-p-chlorophenyl-2-oxazolyl-mercaptoacetic acid
4-phenyl-5-p-dimethylaminophenyl-2-oxazolyl-mercaptoacetic acid
4-p-dimethylaminophenyl-5-phenyl-2-oxazolyl-mercaptoacetic acid (m.p. 128°–130°)
4,5-bis-p-dimethylaminophenyl-2-oxazolyl-mercaptoacetic acid
4-p-dimethylaminophenyl-5-o-chlorophenyl-2-oxazolyl-mercaptoacetic acid, cyclohexylamine salt, m.p. 154°–156°
4-p-dimethylaminophenyl-5-m-chlorophenyl-2-oxazolyl-mercaptoacetic acid
4-p-dimethylaminophenyl-5-p-chlorophenyl-2-oxazolyl-mercaptoacetic acid, m.p. 130°–132°
4-phenyl-5-p-nitrophenyl-2-oxazolyl-mercaptoacetic acid
4-p-nitrophenyl-5-phenyl-2-oxazolyl-mercaptoacetic acid
4,5-bis-p-nitrophenyl-2-oxazolyl-mercaptoacetic acid
4-p-chlorophenyl-5-p-nitrophenyl-2-oxazolyl-mercaptoacetic acid
4-p-nitrophenyl-5-p-chlorophenyl-2-oxazolyl-mercaptoacetic acid
4-phenyl-5-aminophenyl-2-oxazolyl-mercaptoacetic acid
4-aminophenyl-5-phenyl-2oxazolyl-mercaptoacetic acid
4,5-bis-p-aminophenyl-2-oxazolyl-mercaptoacetic acid
4-p-chlorophenyl-5-p-aminophenyl-2-oxazolyl-mercaptoacetic acid 4-p-aminophenyl-5-p-chlorophenyl-2-oxazolyl-mercaptoacetic acid.

c. One gram of 4,5-diphenyl-2-oxazolyl-mercaptoacetic acid ethyl ester is warmed to 50° in 10 ml. of 15% strength hydrochloric acid under agitation for 90 minutes. Then, the reaction mixture is cooled, worked up as usual, and the compound thus obtained is 4,5-diphenyl-2-oxazolyl-mercaptoacetic acid, m.p. 137°–138°.

Analogously, the remaining esters of Formula I ($R_1 =$ esterified carboxyl group) can be saponified to the corresponding acids ($R_1 = COOH$).

EXAMPLE 2 a. 2.65 g. of NaH is suspended in 200 ml. of DMF. Under agitation, 26.9 g. of 2-mercapto-4,5-diphenyl-thiazole (m.p. 219°; obtainable from 1,2-diphenyl-2-chloroethanone and ammonium dithiocarbamate in ethanol) is introduced batchwise under agitation into the suspension; then, the mixture is stirred for 1.5 hours at room temperature, 18.4 g. of the ethyl ester of bromoacetic acid in 50 ml. of DMF is added dropwise to the reaction solution, the latter is agitated for 8 hours at 80°, poured onto ice water, worked up as usual, and the ethyl ester of 4,5-diphenyl-2-thiazolyl-mercaptoacetic acid is thus produced in the form of an oil.

Analogously, the following compounds are produced by reaction with the corresponding halo-fatty acid derivatives:

the ethyl ester of 2-(4,5-diphenyl-2-thiazolyl-mercapto)-2-methylpropionic acid,
the ethyl ester of 4-(4,5-diphenyl-2-thiazolyl-mercapto)-butyric acid,
the ethyl ester of 7-(4,5-diphenyl-2-thiazolyl-mercapto)-heptanoic acid.

Analogously, by utilizing the following starting compounds:
2-mercapto-4-phenyl-5-p-tolyl-thiazole
2-mercapto-4-p-tolyl-5-phenyl-thiazole (m.p. 203°–205°)
2-mercapto-4,5-bis-p-tolyl-thiazole
2-mercapto-4,5-bis-p-isopropylphenyl-thiazole
2-mercapto-4-phenyl-5-p-fluorophenyl-thiazole
2-mercapto-4-p-fluorophenyl-5-phenyl-thiazole
2-mercapto-4,5-bis-p-fluorophenyl-thiazole
2-mercapto-4-p-tolyl-5-p-fluorophenyl-thiazole
2-mercapto-4-p-fluorophenyl-5-p-tolyl-thiazole
2-mercapto-4-phenyl-5-p-chlorophenyl-thiazole
2-mercapto-4-p-chlorophenyl-5-phenyl-thiazole
2-mercapto-4,5-bis-p-chlorophenyl-thiazole (m.p. 245°–250°)
2-mercapto-4-p-tolyl-5-p-chlorophenyl-thiazole
2-mercapto-4-p-chlorophenyl-5-p-tolyl-thiazole
2-mercapto-4-p-fluorophenyl-5-p-chlorophenyl-thiazole
2-mercapto-4-p-chlorophenyl-5-p-fluorophenyl-thiazole
2-mercapto-4-phenyl-5-p-bromophenyl-thiazole
2-mercapto-4-p-bromophenyl-5-phenyl-thiazole
2-mercapto-4,5-bis-p-bromophenyl-thiazole
2-mercapto-4-p-tolyl-5-p-bromophenyl-thiazole
2-mercapto-4-p-bromophenyl-5-p-tolyl-thiazole
2-mercapto-4-p-chlorophenyl-5-p-bromophenyl-thiazole
2-mercapto-4-p-bromophenyl-5-p-chlorophenyl-thiazole
2-mercapto-4-phenyl-5-p-trifluoromethylphenyl-thiazole
2-mercapto-4-p-trifluoromethylphenyl-5-phenyl-thiazole
2-mercapto-4,5-bis-p-trifluoromethylphenyl-thiazole
2-mercapto-4-p-trifluoromethylphenyl-5-p-chlorophenyl-thiazole
2-mercapto-4-p-chlorophenyl-5-p-trifluoromethylphenyl-thiazole
2-mercapto-4-phenyl-5-p-hydroxyphenyl-thiazole
2-mercapto-4-p-hydroxyphenyl-5-phenyl-thiazole
2-mercapto-4,5-bis-p-hydroxyphenyl-thiazole
2-mercapto-4-p-chlorophenyl-5-p-hydroxyphenyl-thiazole
2-mercapto-4-p-hydroxyphenyl-5-p-chlorophenyl-thiazole
2-mercapto-4-phenyl-5-p-methoxyphenyl-thiazole
2-mercapto-4-p-methoxyphenyl-5-phenyl-thiazole
2-mercapto-4,5-bis-p-methoxyphenyl-thiazole
2-mercapto-4-p-chlorophenyl-5-p-methoxyphenyl-thiazole
2-mercapto-4-p-methoxyphenyl-5-p-chlorophenyl-thiazole
2-mercapto-4-phenyl-5-(3,4-dimethoxyphenyl)-thiazole
2-mercapto-4-(3,4-dimethoxyphenyl)-5-phenyl-thiazole
2-mercapto-4,5-bis-(3,4-dimethoxyphenyl)-thiazole
2-mercapto-4-p-chlorophenyl-5-(3,4-dimethoxyphenyl)-thiazole
2-mercapto-4-(3,4-dimethoxyphenyl)-5-p-chlorophenyl-thiazole
2-mercapto-4-phenyl-5-(3,4-methylenedioxyphenyl)-thiazole
2-mercapto-4-(3,4-methylenedioxyphenyl)-5-phenyl-thiazole
2mercapto-4,5-bis-(3,4-methylenedioxyphenyl)-thiazole
2-mercapto-4-p-chlorophenyl-5-(3,4-methylenedioxyphenyl)-thiazole
2-mercapto-4-(3,4-methylenedioxyphenyl)-5-p-chlorophenyl-thiazole
2-mercapto-4-phenyl-5-p-methylmercaptophenyl-thiazole
2-mercapto-4-p-methylmercaptophenyl-5-phenyl-thiazole
2-mercapto-4,5-bis-p-methylmercaptophenyl-thiazole
2-mercapto-4-p-chlorophenyl-5-p-methylmercaptophenyl-thiazole
2-mercapto-4-p-methylmercaptophenyl-5-p-chlorophenyl-thiazole
2-mercapto-4-phenyl-5-p-dimethylaminophenyl-thiazole
2-mercapto-4-p-dimethylaminophenyl-5-phenyl-thiazole
2-mercapto-4,5-bis-p-dimethylaminophenyl-thiazole
2-mercapto-4-p-chlorophenyl-5-p-dimethylaminophenyl-thiazole
2-mercapto-4-p-dimethylaminophenyl-5-p-chlorophenyl-thiazole
2-mercapto-4-phenyl-5-p-nitrophenyl-thiazole
2-mercapto-4-p-nitrophenyl-5-phenyl-thiazole
2-mercapto-4,5-bis-p-nitrophenyl-thiazole
2-mercapto-4-p-chlorophenyl-5-p-nitrophenyl-thiazole
2-mercapto-4-p-nitrophenyl-5-p-chlorophenyl-thiazole
2-mercapto-4-phenyl-5-p-aminophenyl-thiazole
2-mercapto-4-p-aminophenyl-5-phenyl-thiazole
2-mercapto-4,5-bis-p-aminophenyl-thiazole
2-mercapto-4-p-chlorophenyl-5-p-aminophenyl-thiazole
2-mercapto-4-p-aminophenyl-5-p-chlorophenyl-thiazole, the following compounds can be produced by reaction with the corresponding halo-fatty acid derivatives:

the ethyl esters of each of the acids set forth below:
4-phenyl-5-p-tolyl-2-thiazolyl-mercaptoacetic acid
4-p-tolyl-5-phenyl-2-thiazolyl-mercaptoacetic acid (m.p. of this ethyl ester: 67°–69°)
4,5-bis-p-tolyl-2-thiazolyl-mercaptoacetic acid
4,5-bis-p-isopropylphenyl-2-thiazolyl-mercaptoacetic acid
4-phenyl-5-p-fluorophenyl-2-thiazolyl-mercaptoacetic acid
4-p-fluorophenyl-5-phenyl-2-thiazolyl-mercaptoacetic acid
4,5-bis-p-fluorophenyl-2-thiazolyl-mercaptoacetic acid
4-p-tolyl-5-p-fluorophenyl-2-thiazolyl-mercaptoacetic acid
4-p-fluorophenyl-5-p-tolyl-2-thiazolyl-mercaptoacetic acid
4-phenyl-5-p-chlorophenyl-2-thiazolyl-mercaptoacetic acid
4-p-chlorophenyl-5-phenyl-2-thiazolyl-mercaptoacetic acid
4,5-bis-p-chlorophenyl-2-thiazolyl-mercaptoacetic acid (m.p. of this ethyl ester: 90°–91°)
2-(4,5-bis-p-chlorophenyl-2-thiazolyl-mercapto)-propionic acid
2-(4,5-bis-p-chlorophenyl-2-thiazolyl-mercapto)-butyric acid
4-p-tolyl-5-p-chlorophenyl-2-thiazolyl-mercaptoacetic acid
4-p-chlorophenyl-5-p-tolyl-2-thiazolyl-mercaptoacetic acid
4-p-fluorophenyl-5-p-chlorophenyl-2-thiazolyl-mercaptoacetic acid
4-p-chlorophenyl-5-p-fluorophenyl-2-thiazolyl-mercaptoacetic acid
4-phenyl-5-p-bromophenyl-2-thiazolyl-mercaptoacetic acid
4-p-bromophenyl-5-phenyl-2-thiazolyl-mercaptoacetic acid
4,5-bis-p-bromophenyl-2-thiazolyl-mercaptoacetic acid
4-p-tolyl-5-p-bromophenyl-2-thiazolyl-mercaptoacetic acid
4-p-bromophenyl-5-p-tolyl-2-thiazolyl-mercaptoacetic acid
4-p-chlorophenyl-5-p-bromophenyl-2-thiazolyl-mercaptoacetic acid
4-p-bromophenyl-5-p-chlorophenyl-2-thiazolyl-mercaptoacetic acid
4-phenyl-5-p-trifluoromethylphenyl-2-thiazolyl-mercaptoacetic acid
4-p-trifluoromethylphenyl-5-phenyl-2-thiazolyl-mercaptoacetic acid
4,5-bis-p-trifluoromethylphenyl-2-thiazolyl-mercaptoacetic acid
4-p-trifluoromethylphenyl-5-p-chlorophenyl-2-thiazolyl-mercaptoacetic acid
4-p-chlorophenyl-5-p-trifluoromethylphenyl-2-thiazolyl-mercaptoacetic acid
4-phenyl-5-p-hydroxyphenyl-2-thiazolyl-mercaptoacetic acid
4-p-hydroxyphenyl-5-phenyl-2-thiazolyl-mercaptoacetic acid
4,5-bis-p-hydroxyphenyl-2-thiazolyl-mercaptoacetic acid
4-p-chlorophenyl-5-p-hydroxyphenyl-2-thiazolyl-mercaptoacetic acid
4-p-hydroxyphenyl-5-p-chlorophenyl-2-thiazolyl-mercaptoacetic acid
4-phenyl-5-p-methoxyphenyl-2-thiazolyl-mercaptoacetic acid
4-p-methoxyphenyl-5-phenyl-2-thiazolyl-mercaptoacetic acid
4,5-bis-p-methoxyphenyl-2-thiazolyl-mercaptoacetic acid
4-p-chlorophenyl-5-p-methoxyphenyl-2-thiazolyl-mercaptoacetic acid
4-p-methoxyphenyl-5-p-chlorophenyl-2-thiazolyl-mercaptoacetic acid
4-phenyl-5-(3,4-dimethoxyphenyl)-2-thiazolyl-mercaptoacetic acid
4-(3,4-dimethoxyphenyl)-5-phenyl-2-thiazolyl-mercaptoacetic acid
4,5-bis-(3,4-dimethoxyphenyl)-2-thiazolyl-mercaptoacetic acid
4-p-chlorophenyl-5-(3,4-dimethoxyphenyl)-2-thiazolyl-mercaptoacetic acid
4-(3,4-dimethoxyphenyl)-5-p-chlorophenyl-2-thiazolyl-mercaptoacetic acid
4-phenyl-5-(3,4-methylenedioxyphenyl)-2-thiazolyl-mercaptoacetic acid
4-(3,4-methylenedioxyphenyl)-5-phenyl-2-thiazolyl-mercaptoacetic acid
4,5-bis-(3,4-methylenedioxyphenyl)-2-thiazolyl-mercaptoacetic acid
4-p-chlorophenyl-5-(3,4-methylenedioxyphenyl)-2-thiazolyl-mercaptoacetic acid
4-(3,4-methylenedioxyphenyl)-5-p-chlorophenyl-2-thiazolyl-mercaptoacetic acid
4-phenyl-5-p-methylmercaptophenyl-2-thiazolyl-mercaptoacetic acid
4-p-methylmercaptophenyl-5-phenyl-2-thiazolyl-mercaptoacetic acid
4,5-bis-p-methylmercaptophenyl-2-thiazolyl-mercaptoacetic acid
4-p-chlorophenyl-5-p-methylmercaptophenyl-2-thiazolyl-mercaptoacetic acid
4-p-methylmercaptophenyl-5-p-chlorophenyl-2-thiazolyl-mercaptoacetic acid
4-phenyl-5-p-dimethylaminophenyl-2-thiazolyl-mercaptoacetic acid
4-p-dimethylaminophenyl-5-phenyl-2-thiazolyl-mercaptoacetic acid
4,5-bis-p-dimethylaminophenyl-2-thiazolyl-mercaptoacetic acid
4-p-chlorophenyl-5-p-dimethylaminophenyl-2-thiazolyl-mercaptoacetic acid
4-p-dimethylaminophenyl-5-p-chlorophenyl-2-thiazolyl-mercaptoacetic acid
4-phenyl-5-p-nitrophenyl-2-thiazolyl-mercaptoacetic acid
4-p-nitrophenyl-5-phenyl-2-thiazolyl-mercaptoacetic acid
4,5-bis-p-nitrophenyl-2-thiazolyl-mercaptoacetic acid
4-p-chlorophenyl-5-p-nitrophenyl-2-thiazolyl-mercaptoacetic acid
4-p-nitrophenyl-5-p-chlorophenyl-2-thiazolyl-mercaptoacetic acid
4-phenyl-5-p-aminophenyl-2-thiazolyl-mercaptoacetic acid
4-p-aminophenyl-5-phenyl-2-thiazolyl-mercaptoacetic acid
4,5-bis-p-aminophenyl-2-thiazolyl-mercaptoacetic acid
4-p-chlorophenyl-5-p-aminophenyl-2-thiazolyl-mercaptoacetic acid 4-p-aminophenyl-5-p-chlorophenyl-2-thiazolyl-mercaptoacetic acid b. 25 g. of the ethyl ester of 4,5-diphenyl-2-thiazolyl-mercaptoacetic acid is dissolved in 250 ml. of ethanol, 12 g. $K_2CO_3$ is added thereto, the reaction mixture refluxed for 15 hours, evaporated, the residue dissolved in water, the aqueous phase washed with ether, and adjusted to a pH of 5. After the usual working up operation, 4,5-diphenyl-2-thiazolyl-mercaptoacetic acid is obtained, m.p. 133°-134° (ethyl acetate).

Analogously, the following acids are obtained by saponification of the corresponding esters:
2-(4,5-diphenyl-2-thiazolyl-mercapto)-2-methylpropionic acid (m.p. 148°-149°)
4-(4,5-diphenyl-2-thiazolyl-mercapto)-butyric acid (m.p. 115°-116°)
7-(4,5-diphenyl-2-thiazolyl-mercapto)-heptanoic acid (m.p. 79°-80°)
4-phenyl-5-p-tolyl-2-thiazolyl-mercaptoacetic acid
4-p-tolyl-5-phenyl-2-thiazolyl-mercaptoacetic acid (m.p. 208°-210°)
4,5-bis-p-tolyl-2-thiazolyl-mercaptoacetic acid
4,5-bis-p-isopropylphenyl-2-thiazolyl-mercaptoacetic acid
4-phenyl-5-p-fluorophenyl-2-thiazolyl-mercaptoacetic acid
4-p-fluorophenyl-5-phenyl-2-thiazolyl-mercaptoacetic acid (m.p. 142°-144°)
4,5-bis-p-fluorophenyl-2-thiazolyl-mercaptoacetic acid
4-p-tolyl-5-p-fluorophenyl-2-thiazolyl-mercaptoacetic acid
4-p-fluorophenyl-5-p-tolyl-2-thiazolyl-mercaptoacetic acid
4-phenyl-5-p-chlorophenyl-2-thiazolyl-mercaptoacetic acid
4-p-chlorophenyl-5-phenyl-2-thiazolyl-mercaptoacetic acid
4,5-bis-p-chlorophenyl-2-thiazolyl-mercaptoacetic acid (m.p. 144°-146°)
2-(4,5-bis-p-chlorophenyl-2-thiazolyl-mercapto)-propionic acid (m.p. 158°-160°)
2-(4,5-bis-p-chlorophenyl-2-thiazolyl-mercapto)-butyric acid
4-p-tolyl-5-p-chlorophenyl-2-thiazolyl-mercaptoacetic acid
4-p-chlorophenyl-5-p-tolyl-2-thiazolyl-mercaptoacetic acid  4-p-fluorophenyl-5-p-chlorophenyl-2-thiazolyl-mercaptoacetic acid
4-p-chlorophenyl-5-p-fluorophenyl-2-thiazolyl-mercaptoacetic acid
4-phenyl-5-p-bromophenyl-2-thiazolyl-mercaptoacetic acid
4-p-bromophenyl-5-phenyl-2-thiazolyl-mercaptoacetic acid
4,5-bis-p-bromophenyl-2-thiazolyl-mercaptoacetic acid
4-p-tolyl-5-p-bromophenyl-2-thiazolyl-mercaptoacetic acid
4-p-bromophenyl-5-p-tolyl-2-thiazolyl-mercaptoacetic acid
4-p-chlorophenyl-5-p-bromophenyl-2-thiazolyl-mercaptoacetic acid
4-p-bromophenyl-5-p-chlorophenyl-2-thiazolyl-mercaptoacetic acid
4-phenyl-5-p-trifluoromethylphenyl-2-thiazolyl-mercaptoacetic acid
4-p-trifluoromethylphenyl-5-phenyl-2-thiazolyl-mercaptoacetic acid
4,5-bis-p-trifluoromethylphenyl-2-thiazolyl-mercaptoacetic acid
4-p-trifluoromethylphenyl-5-p-chlorophenyl-2-thiazolyl-mercaptoacetic acid
4-p-chlorophenyl-5-p-trifluoromethylphenyl-2-thiazolyl-mercaptoacetic acid
4-phenyl-5-p-hydroxyphenyl-2-thiazolyl-mercaptoacetic acid
4-p-hydroxyphenyl-5-phenyl-2-thiazolyl-mercaptoacetic acid
4,5-bis-p-hydroxyphenyl-2-thiazolyl-mercaptoacetic acid
4-p-chlorophenyl-5-p-hydroxyphenyl-2-thiazolyl-mercaptoacetic acid
4-p-hydroxyphenyl-5-p-chlorophenyl-2-thiazolyl-mercaptoacetic acid
4-phenyl-5-p-methoxyphenyl-2-thiazolyl-mercaptoacetic acid
4-p-methoxyphenyl-5-phenyl-2-thiazolyl-mercaptoacetic acid
4,5-bis-p-methoxyphenyl-2-thiazolyl-mercaptoacetic acid
4-p-chlorophenyl-5-p-methoxyphenyl-2-thiazolyl-mercaptoacetic acid
4-p-methoxyphenyl-5-p-chlorophenyl-2-thiazolyl-mercaptoacetic acid
4-phenyl-5-(3,4-dimethoxyphenyl)-2-thiazolyl-mercaptoacetic acid
4-(3,4-dimethoxyphenyl)-5-phenyl-2-thiazolyl-mercaptoacetic acid
4,5-bis-(3,4-dimethoxyphenyl)-2-thiazolyl-mercaptoacetic acid
4-p-chlorophenyl-5-(3,4-dimethoxyphenyl)-2-thiazolyl-mercaptoacetic acid
4-(3,4-dimethoxyphenyl)-5-p-chlorophenyl-2-thiazolyl-mercaptoacetic acid
4-phenyl-5-(3,4-methylenedioxyphenyl)-2-thiazolyl-mercaptoacetic acid
4-(3,4-methylenedioxyphenyl)-5-phenyl-2-thiazolyl-mercaptoacetic acid
4,5-bis-(3,4-methylenedioxyphenyl)-2-thiazolyl-mercaptoacetic acid
4-p-chlorophenyl-5-(3,4-methylenedioxyphenyl)-2-thiazolylmercaptoacetic acid
4-(3,4-methylenedioxyphenyl)-5-p-chlorophenyl-2-thiazolylmercaptoacetic acid
4-phenyl-5-p-methylmercaptophenyl-2-thiazolyl-mercaptoacetic acid
4-p-methylmercaptophenyl-5-phenyl-2-thiazolyl-mercaptoacetic acid
4,5-bis-p-methylmercaptophenyl-2-thiazolyl-mercaptoacetic acid
4-p-chlorophenyl-5-p-methylmercaptophenyl-2-thiazolyl-mercaptoacetic acid
4-p-methylmercaptophenyl-5-p-chlorophenyl-2-thiazolyl-mercaptoacetic acid
4-phenyl-5-p-dimethylaminophenyl-2-thiazolyl-mercaptoacetic acid
4-p-dimethylaminophenyl-5-phenyl-2-thiazolyl-mercaptoacetic acid
4,5-bis-p-dimethylaminophenyl-2-thiazolyl-mercaptoacetic acid
4-p-chlorophenyl-5-p-dimethylaminophenyl-2-thiazolyl-mercaptoacetic acid
4-p-dimethylaminophenyl-5-p-chlorophenyl-2-thiazolyl-mercaptoacetic acid
4-phenyl-5-p-nitrophenyl-2-thiazolyl-mercaptoacetic acid 4-p-nitrophenyl-5-phenyl-2-thiazolyl-mercaptoacetic acid
4,5-bis-p-nitrophenyl-2-thiazolyl-mercaptoacetic acid
4-p-chlorophenyl-5-p-nitrophenyl-2-thiazolyl-mercaptoacetic acid
4-p-nitrophenyl-5-p-chlorophenyl-2-thiazolyl-mercaptoacetic acid
4-phenyl-5-p-aminophenyl-2-thiazolyl-mercaptoacetic acid
4-p-aminophenyl-5-phenyl-2-thiazolyl-mercaptoacetic acid
4,5-bis-p-aminophenyl-2-thiazolyl-mercaptoacetic acid
4-p-chlorophenyl-5-p-aminophenyl-2-thiazolyl-mercaptoacetic acid
4-p-aminophenyl-5-p-chlorophenyl-2-thiazolyl-mercaptoacetic acid

EXAMPLE 3 a. 16.1 g. of sodium is dissolved in 2.1 l. of ethanol, and then 112.7 g. of 2-mercapto-4,5-bis-p-chlorophenyl-oxazole and 33.2 g. of chloroacetic acid (or 48.5 g. of bromoacetic acid) are successively introduced into the reaction solution. The reaction mixture is refluxed under agitation for 6 hours. Then, the mixture is cooled, the thus-precipitated sodium salt is filtered, dissolved in water, the aqueous phase washed with ether, slightly acidified with dilute HCl, and worked up as usual, thus obtaining 4,5-bis-p-chlorophenyl-2-oxazolyl-mercaptoacetic acid, m.p. 151°-153° (ethyl acetate).

Analogously, the corresponding oxazolyl- and thiazolylmercaptoalkanoic acids are respectively obtained, as set forth in the following exemplary list, by reacting the corresponding 2-mercapto-oxazoles and/or 2-mercapto-thiazoles with chloroacetic acid, 2-chloropropionic acid, 3-chloropropionic acid, 2-chlorobutyric acid, 3-chlorobutyric acid, 4-chlorobutyric acid, 2-chloro-2-methylpropionic acid, 2-chlorovaleric acid, 5-chlorovaleric acid, 2-chloroisovaleric acid, 2-chlorocaproic acid, 6-chlorocaproic acid, 2-chloroheptanoic acid, 7-chloroheptanoic acid, 2-chlorooctanoic acid, 8-chlorooctanoic acid, 2-chlorononanoic acid, 9-chlorononanoic acid, 2-chlorodecanoic acid, 10-chlorodecanoic acid, 2-chloroundecanoic acid, 11-chloroundecanoic acid, and/or with the corresponding bromine or iodine compounds:
2-(4,5-bis-p-chlorophenyl-2-oxazolyl-mercapto)-propionic acid
3-(4,5-bis-p-chlorophenyl-2-oxazolyl-mercapto)-propionic acid
2-(4,5-bis-p-chlorophenyl-2-oxazolyl-mercapto)-butyric acid
3-(4,5-bis-p-chlorophenyl-2-oxazolyl-mercapto)-butyric acid
4-(4,5-bis-p-chlorophenyl-2-oxazolyl-mercapto)-butyric acid
2-(4,5-bis-p-chlorophenyl-2-oxazolyl-mercapto)-2-methylpropionic acid
2-(4,5-bis-p-chlorophenyl-2-oxazolyl-mercapto)-valeric acid
5-(4,5-bis-p-chlorophenyl-2-oxazolyl-mercapto)-valeric acid
2-(4,5-bis-p-chlorophenyl-2-oxazolyl-mercapto)-isovaleric acid
2-(4,5-bis-p-chlorophenyl-2-oxazolyl-mercapto)-caproic acid
6-(4,5-bis-p-chlorophenyl-2-oxazolyl-mercapto)-caproic acid
2-(4,5-bis-p-chlorophenyl-2-oxazolyl-mercapto)-heptanoic acid
7-(4,5-bis-p-chlorophenyl-2-oxazolyl-mercapto)-heptanoic acid
2-(4,5-bis-p-chlorophenyl-2-oxazolyl-mercapto)-octanoic acid
8-(4,5-bis-p-chlorophenyl-2-oxazolyl-mercapto)-octanoic acid
2-(4,5-bis-p-chlorophenyl-2-oxazolyl-mercapto)-nonanoic acid
9-(4,5-bis-p-chlorophenyl-2-oxazolyl-mercapto)-nonanoic acid
2-(4,5-bis-p-chlorophenyl-2-oxazolyl-mercapto)-decanoic acid
10-(4,5-bis-p-chlorophenyl-2-oxazolyl-mercapto)-decanoic acid
2-(4,5-bis-p-chlorophenyl-2-oxazolyl-mercapto)-undecanoic acid
11-(4,5-bis-p-chlorophenyl-2-oxazolyl-mercapto)-undecanoic acid.

b. One gram of 4,5-bis-p-chlorophenyl-2-oxazolyl-mercaptoacetic acid is dissolved in 10 ml. of THF; under agitation, ethereal diazomethane solution is added dropwise until the evolution of nitrogen has ceased. After 20 minutes, the mixture is evaporated, thus obtaining the methyl ester of 4,5-bis-p-chlorophenyl-2-oxazolyl-mercaptoacetic acid, m.p. 79°-82° (hexane).

Analogously, the following compounds are produced from the corresponding acids with diazomethane: the methyl esters of each of the following acids:
4,5-diphenyl-2-oxazolyl-mercaptoacetic acid
2-(4,5-diphenyl-2-oxazolyl-mercapto)-butyric acid
2-(4,5-diphenyl-2-oxazolyl-mercapto)-2-methylpropionic acid
3-(4,5-diphenyl-2-oxazolyl-mercapto)-propionic acid
4-(4,5-diphenyl-2-oxazolyl-mercapto)-butyric acid
7-(4,5-diphenyl-2-oxazolyl-mercapto)-heptanoic acid
4,5-bis-p-tolyl-2-oxazolyl-mercaptoacetic acid
2-(4,5-bis-p-chlorophenyl-2-oxazolyl-mercapto)-propionic acid
3-(4,5-bis-p-chlorophenyl-2-oxazolyl-mercapto)-propionic acid
2-(4,5-bis-p-chlorophenyl-2-oxazolyl-mercapto)-butyric acid
4-p-methoxyphenyl-5-phenyl-2-oxazolyl-mercaptoacetic acid
4,5-bis-p-methoxyphenyl-2-oxazolyl-mercaptoacetic acid
4,5-bis-(3,4-dimethoxyphenyl)-2-oxazolyl-mercaptoacetic acid
4-p-dimethylaminophenyl-5-o-chlorophenyl-2-oxazolyl-mercaptoacetic acid
4-p-dimethylaminophenyl-5-p-chlorophenyl-2-oxazolyl-mercaptoacetic acid
4,5-bis-(3,4-methylenedioxyphenyl)-2-oxazolyl-mercaptoacetic acid
4,5-diphenyl-2-thiazolyl-mercaptoacetic acid
2-(4,5-diphenyl-2-thiazolyl-mercapto)-2-methylpropionic acid
4-(4,5-diphenyl-2-thiazolyl-mercapto)-butyric acid
7-(4,5-diphenyl-2-thiazolyl-mercapto)-heptanoic acid
4,5-bis-p-chlorophenyl-2-thiazolyl-mercaptoacetic acid.

With diazoethane and phenyldiazomethane, respectively, the corresponding ethyl or benzyl esters are analogously obtained, for example, the benzyl ester of 4,5-bis-p-chlorophenyl-2-oxazolyl-mercaptoacetic acid.

c. One gram of 4,5-bis-p-chlorophenyl-2-oxazolyl-mercaptoacetic acid is allowed to stand in 15 ml. of ethanolic hydrochloric acid for 24 hours at room temperature. Then, the mixture is evaporated, worked up as usual, and the product thus obtained is the ethyl ester of 4,5-bis-p-chlorophenyl-2-oxazolyl-mercaptoacetic acid, m.p. 122°–124°.

Analogously (reaction times up to 3 days), from the corresponding acids by reaction with HCl in methanol, ethanol, n-propanol, isopropanol, n-butanol, isobutanol, sec.-butanol, n-pentanol, isopentanol, n-hexanol, n-heptanol, n-octanol, 2-ethylhexanol, n-nonanol, n-decanol, and n-dodecanol, respectively, the corresponding methyl, ethyl, n-propyl, isopropyl, n-butyl, isobutyl, sec.-butyl, n-pentyl, isopentyl, n-hexyl, n-heptyl, n-octyl, 2-ethylhexyl, n-nonyl, n-decyl, and n-dodecyl esters, respectively, are obtained, for example the

| | |
|---|---|
| meyhyl ester, m.p. 79–82° | n-hexyl ester |
| n-propyl ester | n-heptyl ester |
| isopropyl ester | n-octyl ester |
| n-butyl ester | 2-ethylhexyl ester |
| isobutyl ester | n-nonyl ester |
| sec.-butyl ester | n-decyl ester or |
| n-pentyl ester | n-dodecyl ester, b.p. |
| isopentyl ester | 265–270°/ 0.05 mm., | of 4,5-bis-p-chlorophenyl-2-oxazolyl-mercaptoacetic acid, as well as the

| | |
|---|---|
| methyl ester | isopentyl ester |
| n-propyl ester | n-hexyl ester |
| isopropyl ester | n-heptyl ester |
| n-butyl ester | n-octyl ester |
| isobutyl ester | 2-ethylhexyl ester |
| sec.-butyl ester | n-nonyl ester |
| n-pentyl ester | n-decyl ester or |
| | n-dodecyl ester | of 2-(4,5-bis-p-chlorophenyl-2-oxazolyl-mercapto)-propionic acid.

d. 3.8 g. of 4,5-bis-p-chlorophenyl-2-oxazolyl-mercaptoacetic acid and 0.9 g. of cyclopentanol are dissolved in 40 ml. of absolute tetrahydrofuran and mixed with 2.06 g. of dicyclohexylcarbodiimide. The reaction mixture is allowed to stand for 24 hours at room temperature, the thus-precipitated dicyclohexylurea is filtered off, the mixture evaporated, and in this way the cyclopentyl ester of 4,5-bis-p-chlorophenyl-2-oxazolyl-mercaptoacetic acid is produced.

e. 7 g. of 4,5-bis-p-chlorophenyl-2-oxazolyl-mercaptoacetic acid and 4 g. of 2-diethylaminoethyl chloride hydrochloride are refluxed in a solution prepared from 1.07 g. of Na and 70 ml. of isopropanol for 8 hours. The mixture is then evaporated, worked up as usual, and the 2-diethylaminoethyl ester of 4,5-bis-p-chlorophenyl-2-oxazolyl-mercaptoacetic acid is obtained.

Analogously, with 2-dimethylaminoethyl chloride, 2-pyrrolidinoethyl chloride, 2-piperidinoethyl chloride, 2-morpholinoethyl chloride, 3-dimethylaminopropyl chloride, 3-diethylaminopropyl chloride, 3-pyrrolidinopropyl chloride, 3-piperidinopropyl chloride, or 3-morpholinopropyl chloride, the following esters are produced:

| | |
|---|---|
| 2-dimethylaminoethyl ester | 2-pyrrolidinoethyl ester |
| 2-piperidinoethyl ester | 2-morpholinoethyl ester |
| 3-dimethylaminopropyl ester | 3-diethylaminopropyl ester |
| 3-pyrrolidinopropyl ester | 3-piperidinopropyl ester |
| 3-morpholinopropyl ester | | of 4,5-bis-p-chlorophenyl-2-oxazolyl-mercaptoacetic acid, and with the other above-mentioned acids of Formula I ($R_1$ = COOH), the corresponding esters are obtained.

f. 3 g. of sodium methylate is suspended in 100 ml. of DMF, 9.5 g. of 2-diethylaminoethyl chloride hydrochloride is added thereto, and the reaction mixture is stirred for 20 minutes at room temperature. Then, 16.7 g. of 4,5-diphenyl-2-oxazolyl-mercaptoacetic acid sodium salt is added. Under agitation, the reaction mixture is heated to 80° for 40 hours, then diluted with water, dilute hydrochloric acid is added to a pH of 2–3, and the reaction solution is washed with ethyl acetate. Then, the pH of the aqueous solution is adjusted to 9. The mixture is worked up as usual, thus obtaining the 2-diethylaminoethyl ester of 4,5-diphenyl-2-oxazolyl-mercaptoacetic acid; hydrochloride, m.p. 160°–162°.

EXAMPLE 4

Analogously to Example 3, with the following starting compounds:
2-mercapto-4,5-bis-p-tert.-butylphenyl-oxazole
2-mercapto-4,5-bis-p-n-propoxyphenyl-oxazole
2-mercapto-4,5-bis-p-n-butoxyphenyl-oxazole
2-mercapto-4,5-bis-p-diethylaminophenyl-oxazole
2-mercapto-4,5-bis-p-ethylmercaptophenyl-oxazole
2-mercapto-4,5-bis-p-n-propylmercaptophenyl-oxazole
2-mercapto-4,5-bis-p-n-butylmercaptophenyl-oxazole
2-mercapto-4,5-bis-(1-naphthyl)-oxazole
2-mercapto-4,5-bis-(2-naphthyl)-oxazole,
the compounds set forth below are obtained by reaction with chloroacetic acid:
4,5-bis-p-tert.-butylphenyl-2-oxazolyl-mercaptoacetic acid
4,5-bis-p-n-propoxyphenyl-2-oxazolyl-mercaptoacetic acid
4,5-bis-p-n-butoxyphenyl-2-oxazolyl-mercaptoacetic acid
4,5-bis-p-diethylaminophenyl-2-oxazolyl-mercaptoacetic acid
4,5-bis-p-ethylmercaptophenyl-2-oxazolyl-mercaptoacetic acid
4,5-bis-p-n-propylmercaptophenyl-2-oxazolyl-mercaptoacetic acid
4,5-bis-p-n-butylmercaptophenyl-2-oxazolyl-mercaptoacetic acid
4,5-bis-(1-naphthyl)-2-oxazolyl-mercaptoacetic acid
4,5-bis-(2-naphthyl)-2-oxazolyl-mercaptoacetic acid.

EXAMPLE 5

A solution of 34.4 g. of the sodium salt of 2-mercapto-4,5-bis-p-chlorophenyl-oxazole in 600 ml. of isopropanol is mixed with 17.5 g. of the sodium salt of α-bromopropionic acid and refluxed under agitation for 5 hours. The mixture is then concentrated by evaporation, dissolved in water, washed with ethyl acetate, the aqueous phase acidified, and the mixture worked up as usual, thus obtaining 2-(4,5-bis-p-chlorophenyl-2-oxazolyl-mercapto)-propionic acid, m.p. 138°–140° (ethyl acetate); Na-salt, m.p. 267°–268°.

In an analogous manner, by reacting the sodium salts of the corresponding 2-mercapto-4,5-diaryl-oxazoles or -thiazoles, respectively, with the sodium salts of the corresponding halo-fatty acids, the following compounds are produced:
2-(4-phenyl-5-p-tolyl-2-oxazolyl-mercapto)-propionic acid 2-(4-p-tolyl-5-phenyl-2-oxazolyl-mercapto)-propionic acid
2-(4,5-bis-p-tolyl-2-oxazolyl-mercapto)-propionic acid (m.p. 148°–150°)
2-(4,5-bis-p-isopropylphenyl-2-oxazolyl-mercapto)propionic acid (m.p. 96°–98°)
2-(4-phenyl-5-o-fluorophenyl-2-oxazolyl-mercapto)-propionic acid
2-(4-phenyl-5-m-fluorophenyl-2-oxazolyl-mercapto)-propionic acid
2-(4-phenyl-5-p-fluorophenyl-2-oxazolyl-mercapto)-propionic acid
2-(4-o-fluorophenyl-5-phenyl-2-oxazolyl-mercapto)-propionic acid
2-(4-m-fluorophenyl-5-phenyl-2-oxazolyl-mercapto)-propionic acid
2-(4-p-fluorophenyl-5-phenyl-2-oxazolyl-mercapto)-propionic acid
2-(4,5-bis-o-fluorophenyl-2-oxazolyl-mercapto)-propionic acid
2-(4,5-bis-m-fluorophenyl-2-oxazolyl-mercapto)-propionic acid
2-(4,5-bis-p-fluorophenyl-2-oxazolyl-mercapto)-propionic acid
2-(4-p-tolyl-5-p-fluorophenyl-2-oxazolyl-mercapto)-propionic acid
2-(4-p-fluorophenyl-5-p-tolyl-2-oxazolyl-mercapto)-propionic acid
2-(4-phenyl-5-o-chlorophenyl-2-oxazolyl-mercapto)-propionic acid
2-(4-phenyl-5-m-chlorophenyl-2-oxazolyl-mercapto)-propionic acid
2-(4-phenyl-5-p-chlorophenyl-2-oxazolyl-mercapto)-propionic acid
2-(4-o-chlorophenyl-5-phenyl-2-oxazolyl-mercapto)-propionic acid
2-(4-m-chlorophenyl-5-phenyl-2-oxazolyl-mercapto)-propionic acid
2-(4-p-chlorophenyl-5-phenyl-2-oxazolyl-mercapto)-propionic acid
2-(4,5-bis-o-chlorophenyl-2-oxazolyl-mercapto)-propionic acid
2-(4,5-bis-m-chlorophenyl-2-oxazolyl-mercapto)-propionic acid (m.p. 135–136°)
2-(4-p-tolyl-5-p-chlorophenyl-2-oxazolyl-mercapto)-propionic acid
2-(4p-chlorophenyl-5-p-tolyl-2-oxazolyl-mercapto)-propionic acid
2-(4-p-fluorophenyl-5-p-chlorophenyl-2-oxazolyl-mercapto)-propionic acid
2-(4-p-chlorophenyl-5-p-fluorophenyl-2-oxazolyl-mercapto)-propionic acid
2-(4-phenyl-5-o-bromophenyl-2-oxazolyl-mercapto)-propionic acid
2-(4-phenyl-5-m-bromophenyl-2-oxazolyl-mercapto)-propionic acid
2-(4-phenyl-5-p-bromophenyl-2-oxazolyl-mercapto)-propionic acid
2-(4-o-bromophenyl-5-phenyl-2-oxazolyl-mercapto)-propionic acid
2-(4-m-bromophenyl-5-phenyl-2-oxazolyl-mercapto)-propionic acid
2-(4-p-bromophenyl-5-phenyl-2-oxazolyl-mercapto)-propionic acid
2-(4,5-bis-o-bromophenyl-2-oxazolyl-mercapto)-propionic acid
2-(4,5-bis-m-bromophenyl-2-oxazolyl-mercapto)-propionic acid
2-(4,5-bis-p-bromophenyl-2-oxazolyl-mercapto)-propionic acid
2-(4-p-tolyl-5-p-bromophenyl-2-oxazolyl-mercapto)-propionic acid
2-(4-p-bromophenyl-5-p-tolyl-2-oxazolyl-mercapto)-propionic acid
2-(4-p-chlorophenyl-5-p-bromophenyl-2-oxazolyl-mercapto)-propionic acid
2-(4-p-bromophenyl-5-p-chlorophenyl-2-oxazolyl-mercapto)-propionic acid
2-(4-phenyl-5-p-iodophenyl-2-oxazolyl-mercapto)-propionic acid
2-(4-p-iodophenyl-5-phenyl-2-oxazolyl-mercapto)-propionic acid
2-(4,5-bis-p-iodophenyl-2-oxazolyl-mercapto)-propionic acid
2-(4-phenyl-5-p-trifluoromethylphenyl-2-oxazolyl-mercapto)-propionic acid
2-(4-p-trifluoromethylphenyl-5-phenyl-2-oxazolyl-mercapto)-propionic acid
2-(4,5-bis-p-trifluoromethylphenyl-2-oxazolyl-mercapto)-propionic acid
2-(4-p-trifluoromethylphenyl-5-p-chlorophenyl-2-oxazolyl-mercapto)-propionic acid
2-(4-p-chlorophenyl-5-p-trifluoromethylphenyl-2-oxazolyl-mercapto)-propionic acid
2-(4-phenyl-5-p-hydroxyphenyl-2-oxazolyl-mercapto)-propionic acid
2-(4-p-hydroxyphenyl-5-phenyl-2-oxazolyl-mercapto)-propionic acid
2-(4,5-bis-p-hydroxyphenyl-2-oxazolyl-mercapto)-propionic acid
2-(4-p-chlorophenyl-5-p-hydroxyphenyl-2-oxazolyl-mercapto)-propionic acid
2-(4-p-hydroxyphenyl-5-p-chlorophenyl-2-oxazolyl-mercapto)-propionic acid
2-(4-phenyl-5-o-methoxyphenyl-2-oxazolyl-mercapto)-propionic acid
2-(4-phenyl-5-m-methoxyphenyl-2-oxazolyl-mercapto)-propionic acid
2-(4-phenyl-5-p-methoxyphenyl-2-oxazolyl-mercapto)-propionic acid
2-(4-o-methoxyphenyl-5-phenyl-2-oxazolyl-mercapto)-propionic acid
2-(4-m-methoxyphenyl-5-phenyl-2-oxazolyl-mercapto)-propionic acid
2-(4-p-methoxyphenyl-5-phenyl-2-oxazolyl-mercapto)-propionic acid
2-(4,5-bis-o-methoxyphenyl-2-oxazolyl-mercapto)-propionic acid
2-(4,5-bis-m-methoxyphenyl-2-oxazolyl-mercapto)-propionic acid
2-(4,5-bis-p-methoxyphenyl-2-oxazolyl-mercapto)-propionic acid (m.p. 96–98°)
2-(4-p-chlorophenyl-5-p-methoxyphenyl-2-oxazolyl-mercapto)-propionic acid
2-(4-p-methoxyphenyl-5-o-chlorophenyl-2-oxazolyl-mercapto)-propionic acid
2-(4-p-methoxyphenyl-5-m-chlorophenyl-2-oxazolyl-mercapto)-propionic acid
2-(4-p-methoxyphenyl-5-p-chlorophenyl-2-oxazolyl-mercapto)-propionic acid
2-[4-phenyl-5-(3,4-dimethoxyphenyl)-2-oxazolyl-mercapto]-propionic acid
2-[4-(3,4-dimethoxyphenyl)-5-phenyl-2-oxazolyl-mercapto]-propionic acid
2-[4,5-bis-(3,4-dimethoxyphenyl)-2-oxazolyl-mercapto]-propionic acid 2-[4-p-chlorophenyl-5-(3,4-dimethoxyphenyl)-2-oxazolyl-mercapto]-propionic acid
2-[4-(3,4-dimethoxyphenyl)-5-p-chlorophenyl-2-oxazolyl-mercapto]-propionic acid
2-[4-phenyl-5-(3,4-methylenedioxyphenyl)-2-oxazolyl-mercapto]-propionic acid
2-[4-(3,4-methylenedioxyphenyl)-5-phenyl-2-oxazolyl-mercapto]-propionic acid
2-[4,5-bis-(3,4-methylenedioxyphenyl)-2-oxazolyl-mercapto]-propionic acid (m.p. 112–114°)
2-[4-p-chlorophenyl-5-(3,4-methylenedioxyphenyl)-2-oxazolylmercapto]-propionic acid
2-[4-(3,4-methylenedioxyphenyl)-5-o-chlorophenyl-2-oxazolylmercapto]-propionic acid
2-[4-(3,4-methylenedioxyphenyl)-5-m-chlorophenyl-2-oxazolylmercapto]-propionic acid
2-[4-(3,4-methylenedioxyphenyl)-5-p-chlorophenyl-2-oxazolylmercapto]-propionic acid
2-(4-phenyl-5-p-methylmercaptophenyl-2-oxazolyl-mercapto)-propionic acid
2-(4-p-methylmercaptophenyl-5-phenyl-2-oxazolyl-mercapto)-propionic acid
2-(4,5-bis-p-methylmercaptophenyl-2-oxazolyl-mercapto)-propionic acid
2-(4-p-chlorophenyl-5-p-methylmercaptophenyl-2-oxazolyl-mercapto)-propionic acid
2-(4-p-methylmercaptophenyl-5-p-chlorophenyl-2-oxazolyl-mercapto)-propionic acid
2-(4-phenyl-5-p-dimethylaminophenyl-2-oxazolyl-mercapto)-propionic acid
2-(4-p-dimethylaminophenyl-5-phenyl-2-oxazolyl-mercapto)-propionic acid
2-(4,5-bis-p-dimethylaminophenyl-2-oxazolyl-mercapto)-propionic acid
2-(4-p-chlorophenyl-5-p-dimethylaminophenyl-2-oxazolyl-mercapto)-propionic acid
2-(4-p-dimethylaminophenyl-5-o-chlorophenyl-2-oxazolyl-mercapto)-propionic acid
2-(4-p-dimethylaminophenyl-5-m-chlorophenyl-2-oxazolyl-mercapto)-propionic acid
2-(4-p-dimethylaminophenyl-5-p-chlorophenyl-2-oxazolyl-mercapto)-propionic acid
2-(4-phenyl-5-p-nitrophenyl-2-oxazolyl-mercapto)-propionic acid
2-(4-p-nitrophenyl-5-phenyl-2-oxazolyl-mercapto)-propionic acid
2-(4,5-bis-p-nitrophenyl-2-oxazolyl-mercapto)-propionic acid
2-(4-p-chlorophenyl-5-p-nitrophenyl-2-oxazolyl-mercapto)-propionic acid
2-(4-p-nitrophenyl-5-p-chlorophenyl-2-oxazolyl-mercapto)-propionic acid
2-(4-phenyl-5-p-aminophenyl-2-oxazolyl-mercapto)-propionic acid
2-(4-p-aminophenyl-5-phenyl-2-oxazolyl-mercapto)-propionic acid
2-(4,5-bis-p-aminophenyl-2-oxazolyl-mercapto)-propionic acid
2-(4-p-chlorophenyl-5-p-aminophenyl-2-ozazolyl-mercapto)-propionic acid
2-(4-p-aminophenyl-5-p-chlorophenyl-2-oxazolyl-mercapto)-propionic acid.

EXAMPLE 6

3.44 g. of the sodium salt of 2-mercapto-4,5-bis-p-chlorophenyl-oxazole is mixed with 1.89 g. of the sodium salt of α-bromobutyric acid, heated for one hour to 250°, and worked up as usual, thus obtaining 2-(4,5-bis-p-chlorophenyl-2-oxazolylmercapto)-butyric acid, m.p. 130°–132°.

Analogously, by heating the sodium salts of the corresponding 2-mercapto-4,5-diaryl-oxazoles or -thiazoles, respectively, with the sodium salts of the corresponding halo-fatty acids, the corresponding 2-oxazolyl- and 2-thiazolyl-fatty acids, respectively, are obtained, for example:
2-(4,5-diphenyl-2-oxazolyl-mercapto)-butyric acid
2-(4-phenyl-5-p-tolyl-2-oxazolyl-mercapto)-butyric acid
2-(4-p-tolyl-5-phenyl-2-oxazolyl-mercapto)-butyric acid
2-(4,5-bis-p-tolyl-2-oxazolyl-mercapto)-butyric acid (m.p. 98°–100°)
2-(4,5-bis-p-isopropylphenyl-2-oxazolyl-mercapto)-butyric acid (m.p. 72°–74°)
2-(4-phenyl-5-p-fluorophenyl-2-oxazolyl-mercapto)-butyric acid
2-(4-p-fluorophenyl-5-phenyl-2-oxazolyl-mercapto)-butyric acid
2-(4,5-bis-p-fluorophenyl-2-oxazolyl-mercapto)-butyric acid
2-(4-phenyl-5-p-chlorophenyl-2-oxazolyl-mercapto)-butyric acid
2-(4-p-chlorophenyl-5-phenyl-2-oxazolyl-mercapto)-butyric acid
2-(4-phenyl-5-p-bromophenyl-2-oxazolyl-mercapto)-butyric acid
2-(4-p-bromophenyl-5-phenyl-2-oxazolyl-mercapto)-butyric acid
2-(4,5-bis-p-bromophenyl-2-oxazolyl-mercapto)-butyric acid
2-(4-phenyl-5-p-trifluoromethylphenyl-2-oxazolyl-mercapto)-butyric acid
2-(4-p-trifluoromethylphenyl-5-phenyl-2-oxazolyl-mercapto)-butyric acid
2-(4,5-bis-p-trifluoromethylphenyl-2-oxazolyl-mercapto)-butyric acid
2-(4-phenyl-5-p-methoxyphenyl-2-oxazolyl-mercapto)-butyric acid
2-(4-p-methoxyphenyl-5-phenyl-2-oxazolyl-mercapto)-butyric acid
2-(4,5-bis-p-methoxyphenyl-2-oxazolyl-mercapto)-butyric acid
2-[4-phenyl-5-(3,4-methylenedioxyphenyl)-2-oxazolyl-mercapto]-butyric acid
2-[4-(3,4-methylenedioxyphenyl)-5-phenyl-2-oxazolyl-mercapto]-butyric acid
2-[4,5-bis-(3,4-methylenedioxyphenyl)-2-oxazolyl-mercapto]-butyric acid (m.p. 111°–114°).

EXAMPLE 7

10 g. of ethyl acrylate is added dropwise to a solution of 25.3 g. of 4,5-diphenyl-2-mercapto-oxazole and 0.5 g. of sodium methylate in 300 ml. of THF. Thereafter, the reaction mixture is warmed to 50° for 30 minutes and then allowed to stand at room temperature for 2 hours. The solvent is removed, the mixture is worked up as usual, and the ethyl ester of 3-(4,5-diphenyl-2-oxazolyl-mercapto)-propionic acid is obtained, m.p. 62°–64° (hexane/ethyl acetate).

Analogously, with the use of acrylonitrile, 3-(4,5-diphenyl-2-oxazolyl-mercapto)-propionitrile is obtained.

EXAMPLE 8

At 80°, 6 g. of the ethyl ester of diazoacetic acid is added dropwise to a solution of 16.1 g. of 2-mercapto-4,5-bis-p-chlorophenyl-oxazole in 150 ml. of absolute dioxane. After the evolution of nitrogen has ceased, the reaction solution is refluxed for 10 minutes. After the solvent has been removed, the mixture has been worked up as usual, and the crude product has been purified by column chromatography on silica gel, the ethyl ester of 4,5-bis-p-chlorophenyl-2-oxazolyl-mercaptoacetic acid is produced, m.p. 122°-124°.

EXAMPLE 9

16.4 g. of 2-mercapto-4,5-bis-p-chlorophenyl-thiazole, 8.4 g. of ethyl bromoacetate, and 25 g. of silver oxide are refluxed for 15 hours in 300 ml. of THF. After cooling, the silver oxide is separated, the filtrate is concentrated by evaporation, and the residue is purified by column chromatography on silica gel, thus obtaining the ethyl ester of 4,5-bis-p-chlorophenyl-2-thiazolyl-mercaptoacetic acid, m.p. 90°-91°.

EXAMPLE 10 a. 0.6 g. of NaH is suspended in 80 ml. of THF, and 8 g. of 2-mercapto-4,5-bis-p-chlorophenyl-oxazole is added thereto. The mixture is agitated for 1 hour at 25° and then 1.9 g. of chloroacetonitrile is added. The mixture is again stirred at 25° for 5 hours, until no starting material can be detected any more by chromatography. The reaction mixture is mixed with $H_2O$ and worked up as usual, thus obtaining 4,5-bis-p-chlorophenyl-2-oxazolyl-mercaptoacetonitrile, m.p. 105°-106° (diisopropyl ether).

In an analogous manner, from the corresponding 2-mercaptooxazoles or -thiazoles, respectively, with bromoacetonitrile, 2-bromobutyronitrile, 2-bromoisobutyronitrile, 2-bromopropionitrile, 3-bromopropionitrile, 4-bromobutyronitrile, 7-bromoheptanoic acid nitrile, or the corresponding chlorine compounds, the following products are obtained:
4,5-diphenyl-2-oxazolyl-mercaptoacetonitrile
2-(4,5-diphenyl-2-oxazolyl-mercapto)-butyronitrile
2-(4,5-diphenyl-2-oxazolyl-mercapto)-2-methylpropionitrile
2-(4,5-diphenyl-2-oxazolyl-mercapto)-propionitrile
3-(4,5-diphenyl-2-oxazolyl-mercapto)-propionitrile
4-(4,5-diphenyl-2-oxazolyl-mercapto)-butyronitrile
7-(4,5-diphenyl-2-oxazolyl-mercapto)-heptanoic acid nitrile
4,5-bis-p-tolyl-2-oxazolyl-mercaptoacetonitrile
2-(4,5-bis-p-chlorophenyl-2-oxazolyl-mercapto)-propionitrile
3-(4,5-bis-p-chlorophenyl-2-oxazolyl-mercapto)-propionitrile
2-(4,5-bis-p-chlorophenyl-2-oxazolyl-mercapto)-butyronitrile
4-p-methoxyphenyl-5-phenyl-2-oxazolyl-mercaptoacetonitrile
4,5-bis-p-methoxyphenyl-2-oxazolyl-mercaptoacetonitrile
4,5-bis-(3,4-dimethoxyphenyl)-2-oxazolyl-mercaptoacetonitrile
4-p-dimethylaminophenyl-5-o-chlorophenyl-2-oxazolyl-mercaptoacetonitrile
4-p-dimethylaminophenyl-5-p-chlorophenyl-2-oxazolyl-mercaptoacetonitrile
4,5-bis-(3,4-methylenedioxyphenyl)-2-oxazolyl-mercaptoacetonitrile
4,5-diphenyl-2-thiazolyl-mercaptoacetonitrile
2-(4,5-diphenyl-2-thiazolyl-mercapto)-2-methylpropionitrile
4-(4,5-diphenyl-2-thiazolyl-mercapto)-butyronitrile
7-(4,5-diphenyl-2-thiazolyl-mercapto)-heptanoic acid nitrile
4,5-bis-p-chlorophenyl-2-thiazolyl-mercaptoacetonitrile.

b. 14 g. of 4,5-bis-p-chlorophenyl-2-oxazolyl-mercaptoacetonitrile is refluxed in 200 ml. of ethanol and 20 ml. of water with 20 g. of KOH for 40 hours; then, the solvent is distilled off and the residue worked up as usual, thus producing 4,5-bis-p-chlorophenyl-2-oxazolyl-mercaptoacetic acid, m.p. 151°-153°.

Analogously, by alkaline hydrolysis of the remaining nitriles of Formula I ($R_1$ = CN), the corresponding carboxylic acids are obtained.

c. 14 g. of 4,5-bis-p-chlorophenyl-2-oxazolyl-mercaptoacetonitrile is refluxed under a nitrogen atmosphere with 60 ml. of acetic acid and 60 ml. of concentrated hydrochloric acid for 2 hours. The mixture is then evaporated, dissolved in dilute NaOH, washed with ethyl acetate, worked up as usual, and in this manner 4,5-bis-p-chlorophenyl-2-oxazolyl-mercaptoacetic acid is obtained, m.p. 151°-153°.

Analogously, by acid hydrolysis of the remaining nitriles of Formula I ($R_1$ = CN), the corresponding carboxylic acids are produced.

d. 5.6 g. of thionyl chloride and 15.2 g. of 4,5-bis-p-chlorophenyl-2-oxazolyl-mercaptoacetic acid in 100 ml. of benzene are allowed to stand for 24 hours at 25°. The excess thionyl chloride is removed under reduced pressure; 4,5-bis-p-chlorophenyl-2-oxazolyl-mercaptoacetyl chloride is produced as the residue.

Analogously, by treating the remaining acids of Formula I ($R_1$ = COOH) with $SOCl_2$, the corresponding acid chlorides of Formula I ($R_1$ = COCl) are obtained, for example:
4,5-diphenyl-2-oxazolyl-mercaptoacetyl chloride
2-(4,5-bis-p-chlorophenyl-2-oxazolyl-mercapto)-propionyl chloride
2-(4,5-bis-p-chlorophenyl-2-oxazolyl-mercapto)-butyryl chloride.

e. 10 g. of crude 4,5-bis-p-chlorophenyl-2-oxazolyl-mercaptoacetyl chloride is heated with 100 ml. of absolute n-propanol for 3 hours to 95°; then, the mixture is evaporated, worked up as usual, and the thus-obtained product is the n-propyl ester of 4,5-bis-p-chlorophenyl-2-oxazolyl-mercaptoacetic acid.

Analogously, from the acid chlorides corresponding to Formula I ($R_1$ = COCl), with the corresponding alcohols, the corresponding esters of Formula I ($R_1$ = esterified COOH group) are obtained, e.g.:
the n-propyl ester of 4,5-diphenyl-2-oxazolyl-mercaptoacetic acid
the n-propyl ester of 2-(4,5-bis-p-chlorophenyl-2-oxazolylmercapto)-propionic acid
the n-propyl ester of 2-(4,5-bis-p-chlorophenyl-2-oxazolylmercapto)-butyric acid.

f. 9 g. of 4,5-bis-p-chlorophenyl-2-oxazolyl-mercaptoacetyl chloride is dissolved in 100 ml. of absolute tetrahydrofuran and mixed with 3 g. of potassium tert.-butylate. The reaction mixture is agitated at room temperature for 30 minutes, suctionfiltered, evaporated, worked up as usual, and the tert.-butyl ester of 4,5-bis-p-chlorophenyl-2-oxazolyl-mercaptoacetic acid is obtained in this manner.

Analogously, from the remaining acid chlorides of Formula I ($R_1$ = COCl), with potassium tert.-butylate, the corresponding tert.-butyl esters of Formula I ($R_1$ = COO-tert.-$C_4H_9$) are produced.

g. 36.1 g. of 4,5-bis-p-chlorophenyl-2-oxazolyl-mercaptoacetonitrile and 4.6 g. of absolute ethanol are dissolved in 300 ml. of absolute ether and saturated with gaseous HCl at 0°. By allowing the reaction mixture to stand for 8 days at 0°, 4,5-bis-p-chlorophenyl-2-oxazolyl-mercaptoacetic acid iminoethyl ether hydrochloride is separated, which is filtered off.

h. 10 g. of 4,5-bis-p-chlorophenyl-2-oxazolyl-mercaptoacetic acid iminoethyl ether hydrochloride is refluxed with 250 ml. of water for 1 hour. After conducting the usual working-up operation, the ethyl ester of 4,5-bis-p-chlorophenyl-2-oxazolyl-mercaptoacetic acid is produced (m.p. 122°-124°).

i. A solution of 1 g. of 4,5-bis-p-chlorophenyl-2-oxazolyl-mercaptoacetyl chloride in 10 ml. of THF is added dropwise under cooling to 15 ml. of concentrated aqueous $NH_3$ solution. The reaction mixture is agitated for 2 hours, concentrated by evaporation, worked up as usual, and one obtains 4,5-bis-p-chlorophenyl-2-oxazolyl-mercaptoacetamide (m.p. 167°-168°).

EXAMPLE 11 a. Analogously to Example 2, 4,5-bis-p-chlorophenyl-2-oxazolyl-mercaptoacetamide (m.p. 167°-168°) is obtained from 2-mercapto-4,5-bis-p-chlorophenyl-oxazole and bromoacetamide or chloroacetamide.

In an analogous manner, from the corresponding 2-mercapto-oxazoles or -thiazoles, respectively, with the corresponding halo-fatty acid amides, e.g. with bromoacetamide, 2-bromopropionamide, 2-bromobutyramide, 2-bromoisobutyramide, 3-bromopropionamide, 4-bromobutyramide, 7-bromoheptanoic acid amide, or with the corresponding chlorine compounds, the remaining amides of Formula I ($R_1$ = $CONH_2$) are obtained, for example:
4,5-diphenyl-2-oxazolyl-mercaptoacetamide
2-(4,5-diphenyl-2-oxazolyl-mercapto)-propionamide
2-(4,5-diphenyl-2-oxazolyl-mercapto)-butyramide
2-(4,5-diphenyl-2-oxazolyl-mercapto)-2-methylpropionamide
3-(4,5-diphenyl-2-oxazolyl-mercapto)-propionamide
4-(4,5-diphenyl-2-oxazolyl-mercapto)-butyramide
7-(4,5-diphenyl-2-oxazolyl-mercapto)-heptanoic acid amide
4,5-bis-p-tolyl-2-oxazolyl-mercaptoacetamide
2-(4,5-bis-p-chlorophenyl-2-oxazolyl-mercapto)-propionamide
3-(4,5-bis-p-chlorophenyl-2-oxazolyl-mercapto)-propionamide
2-(4,5-bis-p-chlorophenyl-2-oxazolyl-mercapto)-butyramide
4-p-methoxyphenyl-5-phenyl-2-oxazolyl-mercaptoacetamide
4,5-bis-p-methoxyphenyl-2-oxazolyl-mercaptoacetamide
4,5-bis-(3,4-dimethoxyphenyl)-2-oxazolyl-mercaptoacetamide
4-p-dimethylaminophenyl-5-o-chlorophenyl-2-oxazolyl-mercaptoacetamide
4-p-dimethylaminophenyl-5-p-chlorophenyl-2-oxazolyl-mercaptoacetamide
4,5-bis-(3,4-methylenedioxyphenyl)-2-oxazolyl-mercaptoacetamide
4,5-diphenyl-2-thiazolyl-mercaptoacetamide
2-(4,5-diphenyl-2-thiazolyl-mercapto)-2-methylpropionamide
4-(4,5-diphenyl-2-thiazolyl-mercapto)-butyramide
7-(4,5-diphenyl-2-thiazolyl-mercapto)-heptanoic acid amide
4,5-bis-p-chlorophenyl-2-thiazolyl-mercaptoacetamide.

b. 3.8 g. of 4,5-bis-p-chlorophenyl-2-oxazolyl-mercaptoacetamide and 5 g. of KOH are refluxed in 100 ml. of ethanol for 3 hours under a nitrogen atmosphere. The mixture is then concentrated by evaporation and worked up as usual, thus obtaining 4,5-bis-p-chlorophenyl-2-oxazolyl-mercaptoacetic acid, m.p. 151°-153°.

Analogously, by alkaline hydrolysis of the remaining amides of Formula I ($R_1$ = $CONH_2$), the corresponding carboxylic acids of Formula I ($R_1$ = COOH) are produced.

c. 3.8 g. of 4,5-bis-p-chlorophenyl-2-oxazolyl-mercaptoacetamide and 3 g. of p-toluenesulfochloride are allowed to stand in 20 ml. of pyridine for 24 hours at 25°. The mixture is then evaporated and worked up as usual, thus producing 4,5-bis-p-chlorophenyl-2-oxazolyl-mercaptoacetonitrile, m.p. 105°-106°.

EXAMPLE 12

1.2 g. of NaH is added to 12.6 g. of 2-mercapto-4,5-diphenyloxazole in 150 ml. of absolute THF. The mixture is agitated until the formation of the sodium salt is terminated; at 5°, 8.4 g. of the ethyl ester of chlorocarbonyloxyacetic acid is added dropwise to the reaction solution, and the latter is stirred for 3 hours at 25°. After the introduction of gaseous HCl into the reaction mixture, which contains the ethyl ester of 4,5-diphenyl-2-oxazolylmercaptocarbonyloxyacetic acid, the mixture is refluxed until the evolution of $CO_2$ has ceased. After purifying the reaction product by chromatography on silica gel, the ethyl ester of 4,5-diphenyl-2-oxazolyl-mercaptoacetic acid is obtained, m.p. 54°-56° (hexane).

EXAMPLE 13

12 g. of thioglycolic acid ethyl ester is added to a suspension of 2.4 g. of NaH in 200 ml. of freshly distilled DMF, and the mixture is agitated until the evolution of hydrogen has ceased. Thereafter, 25.5 g. of 2-chloro-4,5-diphenyl-oxazole or 30 g. of 2-bromo-4,5-diphenyl-oxazole is added to the mixture. The latter is agitated for 5 hours at 80° and worked up as usual, thus obtaining the ethyl ester of 4,5-diphenyl-2-oxazolylmercaptoacetic acid, b.p. 207°-210°/0.1 mm.; m.p. 54°-56° (hexane).

Analogously, employing the following starting compounds, the corresponding oxazolyl- or thiazolyl-mercapto-alkanoic acid ethyl esters are obtained with the ethyl ester of thioglycolic acid, the ethyl ester of 2-mercaptopropionic acid, the ethyl ester of 2-mercaptobutyric acid, the ethyl ester of 2-mercaptoisobutyric acid, the ethyl ester of 3-mercaptopropionic acid, the ethyl ester of 4-mercaptobutyric acid and the ethyl ester of 7-mercaptoheptanoic acid:
2-chloro-4-phenyl-5-p-tolyl-oxazole
2-chloro-4-p-tolyl-5-phenyl-oxazole
2-chloro-4,5-bis-(p-tolyl)-oxazole
2-chloro-4,5-bis-(p-isopropylphenyl)-oxazole
2-chloro-4-phenyl-5-o-fluorophenyl-oxazole
2-chloro-4-phenyl-5-m-fluorophenyl-oxazole
2-chloro-4-phenyl-5-p-fluorophenyl-oxazole
2-chloro-4-o-fluorophenyl-5-phenyl-oxazole
2-chloro-4-m-fluorophenyl-5-phenyl-oxazole
2-chloro-4-p-fluorophenyl-5-phenyl-oxazole
2-chloro-4,5-bis-(o-fluorophenyl)-oxazole
2-chloro-4,5-bis-(m-fluorophenyl)-oxazole
2-chloro-4,5-bis-(p-fluorophenyl)-oxazole 2-chloro-4-p-tolyl-5-p-fluorophenyl-oxazole
2-chloro-4-p-fluorophenyl-5-p-tolyl-oxazole
2-chloro-4-phenyl-5-o-chlorophenyl-oxazole
2-chloro-4-phenyl-5-m-chlorophenyl-oxazole
2-chloro-4-phenyl-5-p-chlorophenyl-oxazole
2-chloro-4-o-chlorophenyl-5-phenyl-oxazole
2-chloro-4-m-chlorophenyl-5-phenyl-oxazole
2-chloro-4-p-chlorophenyl-5-phenyl-oxazole
2-chloro-4,5-bis-(o-chlorophenyl)-oxazole
2-chloro-4,5-bis-(m-chlorophenyl)-oxazole
2-chloro-4,5-bis-(p-chlorophenyl)-oxazole
2-chloro-4-p-tolyl-5-p-chlorophenyl-oxazole
2-chloro-4-p-chlorophenyl-5-p-tolyl-oxazole
2-chloro-4-p-fluorophenyl-5-p-chlorophenyl-oxazole
2-chloro-4-p-chlorophenyl-5-p-fluorophenyl-oxazole
2-chloro-4-phenyl-5-o-bromophenyl-oxazole
2-chloro-4-phenyl-5-m-bromophenyl-oxazole
2-chloro-4-phenyl-5-p-bromophenyl-oxazole
2-chloro-4-o-bromophenyl-5-phenyl-oxazole
2-chloro-4-m-bromophenyl-5-phenyl-oxazole
2-chloro-4-p-bromophenyl-5-phenyl-oxazole
2-chloro-4,5-bis-(o-bromophenyl)-5-phenyl-oxazole
2-chloro-4,5-bis-(m-bromophenyl)-5-phenyl-oxazole
2-chloro-4,5-bis-(p-bromophenyl)-5-phenyl-oxazole
2-chloro-4-p-tolyl-5-p-bromophenyl-oxazole
2-chloro-4-p-bromophenyl-5-p-tolyl-oxazole
2-chloro-4-p-chlorophenyl-5-p-bromophenyl-oxazole
2-chloro-4-p-bromophenyl-5-p-chlorophenyl-oxazole
2-chloro-4-phenyl-5-p-iodophenyl-oxazole
2-chloro-4-p-iodophenyl-5-phenyl-oxazole
2-chloro-4,5-bis-(p-iodophenyl)-oxazole
2-chloro-4-phenyl-5-p-trifluoromethylphenyl-oxazole
2-chloro-4-p-trifluoromethylphenyl-5-phenyl-oxazole
2-chloro-4,5-bis-(p-trifluoromethylphenyl)-oxazole
2-chloro-4-p-trifluoromethylphenyl-5-p-chlorophenyl-oxazole
2-chloro-4-p-chlorophenyl-5-p-trifluoromethylphenyl-oxazole
2-chloro-4-phenyl-5-p-hydroxyphenyl-oxazole
2-chloro-4-p-hydroxyphenyl-5-phenyl-oxazole
2-chloro-4,5-bis-(p-hydroxyphenyl)-oxazole
2-chloro-4-p-chlorophenyl-5-p-hydroxyphenyl-oxazole
2-chloro-4-p-hydroxyphenyl-5-p-chlorophenyl-oxazole
2-chloro-4-phenyl-5-o-methoxyphenyl-oxazole
2-chloro-4-phenyl-5-m-methoxyphenyl-oxazole
2-chloro-4-phenyl-5-p-methoxyphenyl-oxazole
2-chloro-4-o-methoxyphenyl-5-phenyl-oxazole
2-chloro-4-m-methoxyphenyl-5-phenyl-oxazole
2-chloro-4-p-methoxyphenyl-5-phenyl-oxazole
2-chloro-4,5-bis-(o-methoxyphenyl)-oxazole
2-chloro-4,5-bis-(m-methoxyphenyl)-oxazole
2-chloro-4,5-bis-(p-methoxyphenyl)-oxazole
2-chloro-4-p-chlorophenyl-5-p-methoxyphenyl-oxazole
2-chloro-4-p-methoxyphenyl-5-o-chlorophenyl-oxazole
2-chloro-4-p-methoxyphenyl-5-m-chlorophenyl-oxazole
2-chloro-4-p-methoxyphenyl-5-p-chlorophenyl-oxazole
2-chloro-4-phenyl-5-(3,4-dimethoxyphenyl)-oxazole
2-chloro-4-(3,4-dimethoxyphenyl)-5-phenyl-oxazole
2-chloro-4,5-bis-(3,4-dimethoxyphenyl)-oxazole
2-chloro-4-p-chlorophenyl-5-(3,4-dimethoxyphenyl)-oxazole
2-chloro-4-(3,4-dimethoxyphenyl)-5-p-chlorophenyl-oxazole
2-chloro-4-phenyl-5-(3,4-methylenedioxyphenyl)-oxazole
2-chloro-4-(3,4-methylenedioxyphenyl)-5-phenyl-oxazole
2-chloro-4,5-bis-(3,4-methylenedioxyphenyl)-oxazole
2-chloro-4-p-chlorophenyl-5-(3,4-methylenedioxyphenyl)-oxazole
2-chloro-4-(3,4-methylenedioxyphenyl)-5-o-chlorophenyl-oxazole
2-chloro-4-(3,4-methylenedioxyphenyl)-5-m-chlorophenyl-oxazole
2-chloro-4-(3,4-methylenedioxyphenyl)-5-p-chlorophenyl-oxazole
2-chloro-4-phenyl-5-p-methylmercaptophenyl-oxazole
2-chloro-4-p-methylmercaptophenyl-5-phenyl-oxazole
2-chloro-4,5-bis-p-methylmercaptophenyl-oxazole
2-chloro-4-p-chlorophenyl-5-p-methylmercaptophenyl-oxazole
2-chloro-4-p-methylmercaptophenyl-5-p-chlorophenyl-oxazole
2-chloro-4-phenyl-5-p-dimethylaminophenyl-oxazole
2-chloro-4-p-dimethylaminophenyl-5-phenyl-oxazole
2-chloro-4,5-bis-(p-dimethylaminophenyl)-oxazole
2-chloro-4-p-chlorophenyl-5-p-dimethylaminophenyl-oxazole
2-chloro-4-p-dimethylaminophenyl-5-o-chlorophenyl-oxazole
2-chloro-4-p-dimethylaminophenyl-5-m-chlorophenyl-oxazole
2-chloro-4-p-dimethylaminophenyl-5-p-chlorophenyl-oxazole
2-chloro-4-phenyl-5-p-nitrophenyl-oxazole
2-chloro-4-p-nitrophenyl-5-phenyl-oxazole
2-chloro-4,5-bis-p-nitrophenyl-oxazole
2-chloro-4-p-chlorophenyl-5-p-nitrophenyl-oxazole
2-chloro-4-p-nitrophenyl-5-p-chlorophenyl-oxazole
2-chloro-4-phenyl-5-p-aminophenyl-oxazole
2-chloro-4-p-aminophenyl-5-phenyl-oxazole
2-chloro-4,5-bis-p-aminophenyl-oxazole
2-chloro-4-p-chlorophenyl-5-p-aminophenyl-oxazole
2-chloro-4-p-aminophenyl-5-p-chlorophenyl-oxazole
2-chloro-4,5-diphenyl-thiazole
2-chloro-4-phenyl-5-p-tolyl-thiazole
2-chloro-4-p-tolyl-5-phenyl-thiazole
2-chloro-4,5-bis-p-tolyl-thiazole
2-chloro-4,5-bis-p-isopropylphenyl-thiazole
2-chloro-4-phenyl-5-o-fluorophenyl-thiazole
2-chloro-4-phenyl-5-m-fluorophenyl-thiazole
2-chloro-4-phenyl-5-p-fluorophenyl-thiazole
2-chloro-4-o-fluorophenyl-5-phenyl-thiazole
2-chloro-4-m-fluorophenyl-5-phenyl-thiazole
2-chloro-4-p-fluorophenyl-5-phenyl-thiazole
2-chloro-4,5-bis-o-fluorophenyl-thiazole
2-chloro-4,5-bis-m-fluorophenyl-thiazole
2-chloro-4,5-bis-p-fluorophenyl-thiazole
2-chloro-4-p-tolyl-5-p-fluorophenyl-thiazole
2-chloro-4-p-fluorophenyl-5-p-tolyl-thiazole
2-chloro-4-phenyl-5-o-chlorophenyl-thiazole
2-chloro-4-phenyl-5-m-chlorophenyl-thiazole
2-chloro-4-phenyl-5-p-chlorophenyl-thiazole
2-chloro-4-o-chlorophenyl-5-phenyl-thiazole
2-chloro-4-m-chlorophenyl-5-phenyl-thiazole
2-chloro-4-p-chlorophenyl-5-phenyl-thiazole
2-chloro-4,5-bis-o-chlorophenyl-thiazole
2-chloro-4,5-bis-m-chlorophenyl-thiazole
2-chloro-4,5-bis-p-chlorophenyl-thiazole
2-chloro-4-p-tolyl-5-p-chlorophenyl-thiazole
2-chloro-4-p-chlorophenyl-5-p-tolyl-thiazole
2-chloro-4-p-fluorophenyl-5-p-chlorophenyl-thiazole
2-chloro-4-p-chlorophenyl-5-p-fluorophenyl-thiazole
2-chloro-4-phenyl-5-o-bromophenyl-thiazole
2-chloro-4-phenyl-5-m-bromophenyl-thiazole 2-chloro-4-phenyl-5-p-bromophenyl-thiazole
2-chloro-4-o-bromophenyl-5-phenyl-thiazole
2-chloro-4-m-bromophenyl-5-phenyl-thiazole
2-chloro-4-p-bromophenyl-5-phenyl-thiazole
2-chloro-4,5-bis-o-bromophenyl-5-phenyl-thiazole
2-chloro-4,5-bis-m-bromophenyl-5-phenyl-thiazole
2-chloro-4,5-bis-p-bromophenyl-5-phenyl-thiazole
2-chloro-4-p-tolyl-5-p-bromophenyl-thiazole
2-chloro-4-p-bromophenyl-5-p-tolyl-thiazole
2-chloro-4-p-chlorophenyl-5-p-bromophenyl-thiazole
2-chloro-4-p-bromophenyl-5-p-chlorophenyl-thiazole
2-chloro-4-phenyl-5-p-iodophenyl-thiazole
2-chloro-4-p-iodophenyl-5-phenyl-thiazole
2-chloro-4,5-bis-p-iodophenyl-thiazole
2-chloro-4-phenyl-5-o-trifluoromethylphenyl-thiazole
2-chloro-4-phenyl-5-p-trifluoromethylphenyl-thiazole
2-chloro-4-p-trifluoromethylphenyl-5-phenyl-thiazole
2-chloro-4,5-bis-p-trifluoromethylphenyl-thiazole
2-chloro-4-p-trifluoromethylphenyl-5-p-chlorophenyl-thiazole
2-chloro-4-p-chlorophenyl-5-p-trifluoromethylphenyl-thiazole
2-chloro-4-phenyl-5-p-hydroxyphenyl-thiazole
2-chloro-4-p-hydroxyphenyl-5-phenyl-thiazole
2-chloro-4,5-bis-p-hydroxyphenyl-thiazole
2-chloro-4-p-chlorophenyl-5p-hydroxyphenyl-thiazole
2-chloro-4-p-hydroxyphenyl-5-p-chlorophenyl-thiazole
2-chloro-4-phenyl-5-o-methoxyphenyl-thiazole
2-chloro-4-phenyl-5-m-methoxyphenyl-thiazole
2-chloro-4-phenyl-5-p-methoxyphenyl-thiazole
2-chloro-4-o-methoxyphenyl-5-phenyl-thiazole
2-chloro-4-m-methoxyphenyl-5-phenyl-thiazole
2-chloro-4-p-methoxyphenyl-5-phenyl-thiazole
2-chloro-4,5-bis-o-methoxyphenyl-thiazole
2-chloro-4,5-bis-m-methoxyphenyl-thiazole
2-chloro-4,5-bis-p-methoxyphenyl-thiazole
2-chloro-4-p-chlorophenyl-5-p-methoxyphenyl-thiazole
2-chloro-4-p-methoxyphenyl-5-o-chlorophenyl-thiazole
2-chloro-4-p-methoxyphenyl-5-m-chlorophenyl-thiazole
2-chloro-4-p-methoxyphenyl-5-p-chlorophenyl-thiazole
2-chloro-4-phenyl-5-(3,4-dimethoxyphenyl)-thiazole
2-chloro-4-(3,4-dimethoxyphenyl)-5-phenyl-thiazole
2-chloro-4,5-bis-(3,4-dimethoxyphenyl)-thiazole
2-chloro-4-p-chlorophenyl-5-(3,4-dimethoxyphenyl)-thiazole
2-chloro-4-(3,4-dimethoxyphenyl)-5-p-chlorophenyl-thiazole
2-chloro-4-phenyl-5-(3,4-methylenedioxyphenyl)-thiazole
2-chloro-4-(3,4-methylenedioxyphenyl)-5-phenyl-thiazole
2-chloro-4,5-bis-(3,4-methylenedioxyphenyl)-thiazole
2-chloro-4-p-chlorophenyl-5-(3,4-methylenedioxyphenyl)-thiazole
2-chloro-4-(3,4-methylenedioxyphenyl)-5-o-chlorophenyl-thiazole
2-chloro-4-(3,4-methylenedioxyphenyl)-5-m-chlorophenyl-thiazole
2-chloro-4-(3,4-methylenedioxyphenyl)-5-p-chlorophenyl-thiazole
2-chloro-4-phenyl-5-p-methylmercaptophenyl-thiazole
2-chloro-4-p-methylmercaptophenyl-5-phenyl-thiazole
2-chloro-4,5-bis-p-methylmercaptophenyl-thiazole
2-chloro-4-p-chlorophenyl-5-p-methylmercaptophenyl-thiazole
2-chloro-4-p-methylmercaptophenyl-5-p-chlorophenyl-thiazole
2-chloro-4-phenyl-5-p-dimethylaminophenyl-thiazole
2-chloro-4-p-dimethylaminophenyl-5-phenyl-thiazole
2-chloro-4,5-bis-p-dimethylaminophenyl-thiazole
2-chloro-4-p-chlorophenyl-5-p-dimethylaminophenyl-thiazole
2-chloro-4-p-dimethylaminophenyl-5-o-chlorophenyl-thiazole
2-chloro-4-p-dimethylaminophenyl-5-m-chlorophenyl-thiazole
2-chloro-4-p-dimethylaminophenyl-5-p-chlorophenyl-thiazole
2-chloro-4-phenyl-5-p-nitrophenyl-thiazole
2-chloro-4-p-nitrophenyl-5-phenyl-thiazole
2-chloro-4,5-bis-p-nitrophenyl-thiazole
2-chloro-4-p-chlorophenyl-5-p-nitrophenyl-thiazole
2-chloro-4-p-nitrophenyl-5-p-chlorophenyl-thiazole
2-chloro-4-phenyl-5-p-aminophenyl-thiazole
2-chloro-4-p-aminophenyl-5-phenyl-thiazole
2-chloro-4,5-bis-p-aminophenyl-thiazole
2-chloro-4-p-chlorophenyl-5-p-aminophenyl-thiazole
2-chloro-4-p-aminophenyl-5-p-chlorophenyl-thiazole,
or by using the corresponding bromine compounds as the starting materials, for example:
2-bromo-4,5-bis-p-chlorophenyl-oxazole
2-bromo-4,5-bis-p-chlorophenyl-thiazole.

EXAMPLE 14

3.24 g. of 2-chloro-4,5-bis-p-chlorophenyl-oxazole (or 3.69 g. of 2-bromo-4,5-bis-p-chlorophenyl-oxazole) and 1.36 g. of the disodium salt of thioglycolic acid are refluxed in 20 ml. of n-butanol for 4 hours. The reaction mixture is evaporated, mixed with water and ether, separated, the aqueous phase acidified, and worked up as usual, thus obtaining 4,5-bis-p-chlorophenyl-2-oxazolyl-mercaptoacetic acid, m.p. 151°–153°.

Analogously, the corresponding carboxylic acids of Formula I ($R_1$ = COOH) are obtained from the remaining 2-chloro- and 2-bromo-oxazoles or -thiazoles, respectively, of Formula II ($X_1$ = Cl or Br) with the sodium salts of the corresponding sodium mercaptofatty acids, e.g. the disodium salts of:
thioglycolic acid (mercaptoacetic acid)
2-mercaptopropionic acid
3-mercaptopropionic acid
2-mercaptobutyric acid
3-mercaptobutyric acid
4-mercaptobutyric acid
2-mercaptoisobutyric acid
2-mercaptovaleric acid
5-mercaptovaleric acid
2-mercaptoisovaleric acid
2-mercaptocaproic acid
6-mercaptocaproic acid
2-mercaptoheptanoic acid
7-mercaptoheptanoic acid
2-mercaptooctanoic acid
8-mercaptooctanoic acid
2-mercaptononanoic acid
9-mercaptononanoic acid
2-mercaptodecanoic acid
10-mercaptodecanoic acid
2-mercaptoundecanoic acid
11-mercaptoundecanoic acid.

EXAMPLE 15

1.2 g. of NaH is added to a solution of 6 g. of the ethyl ester of thioglycolic acid in 100 ml. of absolute THF. The reaction mixture is stirred for 30 minutes at room temperature; then, 19.2 g. of 2-bromo-4,5-bis-p-chlorophenyl-thiazole (obtainable by reacting 2-hydroxy-4,5-bis-p-chlorophenyl-thiazole with POBr$_3$), dissolved in 40 ml. of THF, is added dropwise. The reaction mixture is refluxed under agitation for 12 hours. After cooling, the thus-precipitated NaBr is separated and the filtrate is concentrated by evaporation. After the usual working-up procedure, the ethyl ester of 4,5-bis-p-chlorophenyl-2-thiazolyl-mercaptoacetic acid is produced (m.p. 90°–91°).

EXAMPLE 16

8.15 g. of the cyclohexyl ester of thioglycolic acid is dissolved in 80 ml. of absolute THF, and 2.6 g. of sodium methylate is added thereto. The reaction mixture is agitated for 15 minutes. Then, 12 g. of 2-chloro-4,5-diphenyl-oxazole (b.p. 170°/0.05 mm.; producible by reacting 4,5-diphenyl-2-oxazolone with POCl$_3$) in 20 ml. of THF is added dropwise. The reaction mixture is refluxed under agitation for 9 hours. The thus-precipitated NaCl is filtered off and the filtrate concentrated by evaporation, thus obtaining the cyclohexyl ester of 4,5-diphenyl-2-oxazolyl mercaptoacetic acid as an oily residue. The latter (16 g.) is refluxed in 150 ml. of ethanol with 8 g. of pulverized K$_2$CO$_3$ for 2 hours. After conducting the usual working-up operation, 4,5-diphenyl-2-oxazolyl-mercaptoacetic acid is obtained, m.p. 137°–138°.

EXAMPLE 17

15 g. of 4,5-diphenyl-2-oxazolyl-mercaptoacetaldehyde (obtainable by the reaction of 2-mercapto-4,5-diphenyl-oxazole with bromoacetaldehyde-diethylacetal and subsequent acid hydrolysis) is added under agitation to a solution of 25 g. of silver nitrate in 200 ml. of water and 140 ml. of ethanol. Under agitation, 360 ml of 0.5N NaOH is added dropwise within 2 hours to the reaction mixture; then, the mixture is stirred for 6 hours at room temperature under a nitrogen atmosphere, filtered off, the filtrate is worked up as usual, and 4,5-diphenyl-2-oxazolyl-mercaptoacetic acid is thus obtained, m.p. 137°–138°.

Analogously, the corresponding carboxylic acids are obtained from the remaining aldehydes of Formula II (X$_1$ = S—A—CHO), for example from those set out hereinbelow, by oxidation with silver oxide:
2-(4,5-diphenyl-2-oxazolyl-mercapto)-butanal
2-(4,5-diphenyl-2-oxazolyl-mercapto)-2-methylpropanal
3(4,5-diphenyl-2-oxazolyl-mercapto)-propanol
4-(4,5-diphenyl-2-oxazolyl-mercapto-butanal
7-(4,5-diphenyl-2-oxazolyl-mercapto)-heptanal
4,5-bis-p-tolyl-2-oxazolyl-mercaptoacetaldehyde
4,5-bis-p-chlorophenyl-2-oxazolyl-mercaptoacetaldehyde
2-(4,5-bis-p-chlorophenyl-2-oxazolyl-mercapto)-propanal
3-(4,5-bis-p-chlorophenyl-2-oxazolyl-mercapto)-propanal
2-(4,5-bis-p-chlorophenyl-2-oxazolyl-mercapto)-butanal
4-p-methoxyphenyl-5-phenyl-2-oxazolyl-mercaptoacetaldehyde
4,5-bis-p-methoxyphenyl-2-oxazolyl-mercaptoacetaldehyde
4,5-bis-(3,4-dimethoxyphenyl)-2-oxazolyl-mercaptoacetaldehyde
4-p-dimethylaminophenyl-5-o-chlorophenyl-2-oxazolyl-mercaptoacetaldehyde
4-p-dimethylaminophenyl-5-p-chlorophenyl-2-oxazolyl-mercaptoacetaldehyde
4,5-bis-(3,4-methylenedioxyphenyl)-2-oxazolyl-mercaptoacetaldehyde
4,5-diphenyl-2-thiazolyl-mercaptoacetaldehyde
2-(4,5-diphenyl-2-thiazolyl-mercapto)-2-methylpropanal
4-(4,5-diphenyl-2-thiazolyl-mercapto)-butanal
7-(4,5-diphenyl-2-thiazolyl-mercapto)-heptanal
4,5-bis-p-chlorophenyl-2-thiazolyl-mercaptoacetaldehyde.

EXAMPLE 18

8.7 g. of 2-(4,5-bis-p-chlorophenyl-2-oxazolyl-mercapto)ethanol (obtainable by reacting 2-mercapto-4,5-bis-p-chlorophenyloxazole with 2-bromoethanol) is dissolved in 40 ml. of 10% H$_2$SO$_4$. To this mixture is added 2.5 g. of Na$_2$Cr$_2$O$_7$ . 2H$_2$O, and the mixture is agitated for two hours at 60°, cooled, worked up as usual, and, after purification by chromatography on silica gel, 4,5-bis-p-chlorophenyl-2-oxazolyl-mercaptoacetic acid is obtained, m.p. 151°–153°.

Analogously, the corresponding carboxylic acids are produced by oxidation from other alcohols of Formula II (X$_1$ = —S—A—CH$_2$OH), for example, from:
2-(4,5-diphenyl-2-oxazolyl-mercapto)-ethanol
2-(4,5-diphenyl-2-oxazolyl-mercapto)-butanol
2-(4,5-diphenyl-2-oxazolyl-mercapto)-2-methylpropanol
3-(4,5-diphenyl-2-oxazolyl-mercapto)-propanol
4-(4,5-diphenyl-2-oxazolyl-mercapto)-butanol
7-(4,5-diphenyl-2-oxazolyl-mercapto)-heptanol
2-(4,5-bis-p-tolyl-2-oxazolyl-mercapto)-ethanol
2-(4,5-bis-p-chlorophenyl-2-oxazolyl-mercapto)-propanol
3-(4,5-bis-p-chlorophenyl-2-oxazolyl-mercapto)-propanol
2-(4,5-bis-p-chlorophenyl-2-oxazolyl-mercapto)-butanol
2-(4,5-methoxyphenyl-5-phenyl-2-oxazolyl-mercapto)-ethanol
2-(4,5-bis-p-methoxyphenyl-2-oxazolyl-mercapto)-ethanol
2-[4,5-bis-(3,4-dimethoxyphenyl)-2-oxazolyl-mercapto]-ethanol
2-(4-p-dimethylaminophenyl-5-o-chlorophenyl-2-oxazolyl-mercapto)-ethanol
2-(4-dimethylaminophenyl-5-p-chlorophenyl-2-oxazolyl)-mercapto)-ethanol
2-[4,5-bis-(3,4-methylenedioxyphenyl)-2-oxazolyl-mercapto]-ethanol
2-(4,5-diphenyl-2-thiazolyl-mercapto)-ethanol
2-(4,5-diphenyl-2-thiazolyl-mercapto)-2-methylpropanol
4-(4,5-diphenyl-2-thiazolyl-mercapto)-butanol
7-(4,5-diphenyl-2-thiazolyl-mercapto)-heptanol
2-(4,5-bis-p-chlorophenyl-2-thiazolyl-mercapto)-ethanol.

EXAMPLE 19 a. A solution of crude 4,5-bis-p-chlorophenyl-2-oxazolyl-mercaptomalonic acid (obtainable by reacting 2-mercapto4,5-bis-p-chlorophenyl-oxazole with the diethyl ester of bromomalonic acid and saponifying 20 g. of the thus-obtained diethyl ester of 4,5-bis-p-chlorphenyl-2-oxazolyl-mercaptomalonic acid with ethanolic KOH under N$_2$) in 200 ml. of acetic acid and 200 ml. of 15% HCl is refluxed under nitrogen until the evolution of CO₂ has ceased. After cooling the mixture and working it up in the usual manner, 4,5-bis-p-chlorophenyl-2-oxazolyl-mercaptoacetic acid is produced, m.p. 151°–153°.

b. 7.5 g. of 4,5-bis-p-chlorophenyl-2-oxazolyl-mercaptoacetic acid and 15 g. of vinyll acetate are shaken with 0.15 g. of mercury acetate for 40 minutes. Then, the mixture is heated to the boiling point, one drop of H₂SO₄ is added thereto, the mixture refluxed for 3 hours, 200 mg. of sodium acetate is added, the mixture concentrated by evaporation, and worked up as usual, thus obtaining the vinyl ester of 4,5-bis-p-chlorophenyl-2-oxazolyl-mercaptoacetic acid.

c. To a solution of 7.5 g. of 4,5-bis-p-chlorophenyl-2-oxazolyl-mercaptoacetic acid in 120 ml. of absolute THF, 1.5 g. of NaH is added, and the mixture is then stirred at 25° for 30 minutes, cooled, and, at 5°, a solution of 3.6 g. of allyl bromide in 25 ml. of absolute THF is added dropwise thereto. The mixture is then again stirred at 25° for 24 hours. After the reaction mixture has been evaporated and worked up as usual, the allyl ester of 4,5-bis-p-chlorophenyl-2-oxazolyl-mercaptoacetic acid is obtained.

EXAMPLE 20

19.5 g. of the monoethyl ester of 4,5-bis-p-chlorophenyl-2-oxazolyl-mercaptomalonic acid (obtainable by partial saponification of the diethyl ester with 1 mol of KOH in ethanol and acidification) is heated gradually to 100°–130° at 18 torr (mm. Hg.) until the evolution of CO₂ has ceased. In this manner, the ethyl ester of 4,5-bis-p-chlorophenyl-2-oxazolyl-mercaptoacetic acid is obtained, m.p. 122°–124°.

EXAMPLE 21 a. 17.5 g. of the ethyl ester of 2-(4,5-bis-p-chlorophenyl-2-oxazolyl-mercapto)-butan-3-one acid (obtainable by reacting 2-mercapto-4,5-bis-p-chlorophenyl-oxazole with the ethyl ester of 2-bromoacetoacetic acid) is agitated under N₂ with 250 ml. of 50% KOH for 45 minutes at 90°. Then, the reaction mixture is cooled, water and HCl are added to a pH of 10, the mixture is washed with ether, and worked up as usual, thus obtaining 4,5-bis-p-chlorophenyl-2-oxazolyl-mercaptoacetic acid, m.p. 151°–153°.

b. 3 g. of 4,5-bis-p-chlorophenyl-2-oxazolyl-mercaptoacetic acid is dissolved in 50 ml. of ethanol and mixed with the stoichiometric amount of ethanolic NaOH. After the addition of 50 ml. of diethyl ether and filtration, the sodium salt of 4,5-bis-p-chlorophenyl-2-oxazolyl-mercaptoacetic acid is obtained, m.p. about 295°.

EXAMPLE 22

23 g. of 1,2-diphenyl-2-chloroethanone is heated together with 18 g. of the ethyl ester of carbamoylmercaptoacetic acid in 150 ml. of absolute DMF for 3 hours to 70°. Then, the DMF is removed, and the residue, containing the ethyl ester of N-(1,2-diphenyl-2-oxoethyl)-carbamoylmercaptoacetic acid, is refluxed for 5 hours with a mixture of 100 g. of POCl₃ and 200 ml. of benzene. The mixture is then evaporated under reduced pressure and the residue is purified by chromatography on silica gel, thus obtaining the ethyl ester of 4,5-diphenyl-2-oxazolyl-mercaptoacetic acid, m.p. 54°–56°.

Analogously, the corresponding oxazole derivatives of Formula I (Z = O, R₁ = esterified COOH group) are produced from the corresponding 1,2-diaryl-2-chloroethanones, examples of which are set forth below, be reaction with carbamoylmercaptoacetic acid esters (e.g. the methyl or ethyl ester of carbamoylmercaptoacetic acid) and subsequent cyclization with POCl₃:

1,2-diphenyl-2-chloroethanone
1-phenyl-2-p-tolyl-2-chloroethanone
1-p-tolyl-2-phenyl-2-chloroethanone
1,2-bis-p-tolyl-2-chloroethanone
1,2-bis-p-isopropylphenyl-2-chloroethanone
1-phenyl-2-o-fluorophenyl-2-chloroethanone
1-phenyl-2-m-fluorophenyl-2-chloroethanone
1-phenyl-2-p-fluorophenyl-2-chloroethanone
1-o-fluorophenyl-2-phenyl-2-chloroethanone
1-m-fluorophenyl-2-phenyl-2-chloroethanone
1-p-fluorophenyl-2-phenyl-2-chloroethanone
1,2-bis-o-fluorophenyl-2-chloroethanone
1,2-bis-m-fluorophenyl-2-chloroethanone
1,2-bis-p-fluorophenyl-2-chloroethanone
1-p-tolyl-2-p-fluorophenyl-2-chloroethanone
1-p-fluorophenyl-2-p-tolyl-2-chloroethanone
1-phenyl-2-o-chlorophenyl-2-chloroethanone
1-phenyl-2-m-chlorophenyl-2-chloroethanone
1-phenyl-2-p-chlorophenyl-2-chloroethanone
1,2-bis-o-chlorophenyl-2-chloroethanone
1,2-bis-m-chlorophenyl-2-chloroethanone
1,2-bis-p-chlorophenyl-2-chloroethanone
1-p-tolyl-2-p-chlorophenyl-2-chloroethanone
1-p-chlorophenyl-2-p-tolyl-2-chloroethanone
1-p-fluorophenyl-2-p-chlorophenyl-2-chloroethanone
1-p-chlorophenyl-2-p-fluorophenyl-2-chloroethanone
1-phenyl-2-o-bromophenyl-2-chloroethanone
1-phenyl-2-m-bromophenyl-2-chloroethanone
1-phenyl-2-p-bromophenyl-2-chloroethanone
1-o-bromophenyl-2-phenyl-2-chloroethanone
1-m-bromophenyl-2-phenyl-2-chloroethanone
1-p-bromophenyl-2-phenyl-2-chloroethanone
1,2-bis-o-bromophenyl-2-chloroethanone
1,2-bis-m-bromophenyl-2-chloroethanone
1,2-bis-p-bromophenyl-2-chloroethanone
1-p-tolyl-2-p-bromophenyl-2-chloroethanone
1-p-bromophenyl-2-p-tolyl-2-chloroethanone
1-p-chlorophenyl-2-p-bromophenyl-2-chloroethanone
1-p-bromophenyl-2-p-chlorophenyl-2-chloroethanone
1-phenyl-2-p-iodophenyl-2-chloroethanone
1p-iodophenyl-2-phenyl-2-chloroethanone
1,2-bis-p-iodophenyl-2-chloroethanone
1-phenyl-2-p-trifluoromethylphenyl-2-chloroethanone
1-p-trifluoromethylphenyl-2-phenyl-2-chloroethanone
1,2-bis-p-trifluoromethylphenyl-2-chloroethanone
1-p-trifluoromethylphenyl-2-p-chlorophenyl-2-chloroethanone
1-p-chlorophenyl-2-p-trifluoromethylphenyl-2-chloroethanone
1-phenyl-2-p-hydroxyphenyl-2-chloroethanone
1-p-hydroxyphenyl-2-phenyl-2-chloroethanone
1,2-bis-p-hydroxyphenyl-2-chloroethane
1-p-chlorophenyl-2-p-hydroxyphenyl-2-chloroethanone
1-p-hydroxyphenyl-2-p-chlorophenyl-2-chloroethanone
1-phenyl-2-o-methoxyphenyl-2-chloroethanone
1-phenyl-2-m-methoxyphenyl-2-chloroethanone
1-phenyl-2-p-methoxyphenyl-2-chloroethanone
1-o-methoxyphenyl-2-phenyl-2-chloroethanone
1-m-methoxyphenyl-2-phenyl-2-chloroethanone
1-p-methoxyphenyl-2-phenyl-2-chloroethanone
1,2-bis-o-methoxyphenyl-2-chloroethanone
1,2-bis-m-methoxyphenyl-2-chloroethanone
1,2-bis-p-methoxyphenyl-2-chloroethanone 1-p-chlorophenyl-2-p-methoxyphenyl-2-chloroethanone
1-p-methoxyphenyl-2-o-chlorophenyl-2-chloroethanone
1-p-methoxyphenyl-2-m-chlorophenyl-2-chloroethanone
1-p-methoxyphenyl-2-p-chlorophenyl-2-chloroethanone
1-phenyl-2-(3,4-dimethoxyphenyl)-2-chloroethanone
1-(3,4-dimethoxyphenyl)-2-phenyl-2-chloroethanone
1,2-bis-(3,4-dimethoxyphenyl0-2-chloroethanone
1-p-chlorophenyl-2-(3,4-dimethoxyphenyl)-2-chloroethanone
1-(3,4-dimethoxyphenyl)-2-p-chlorophenyl-2-chloroethanone
1-phenyl-2-(3,4-methylenedioxyphenyl)-2-chloroethanone
1-(3,4-methylenedioxyphenyl)-2-phenyl-2-chloroethanone
1,2-bis-(3,4-methylenedioxyphenyl)-2-chloroethanone
1-p-chlorophenyl-2-(3,4-methylenedioxyphenyl)-2-chloroethanone
1-(3,4-methylenedioxyphenyl)-2-o-chlorophenyl-2-chloroethanone
1-(3,4-methyleneidoxyphenyl)-2-m-chlorophenyl-2-chloroethanone
1-(3,4-methylenedioxyphenyl)-2-p-chlorophenyl-2-chloroethanone
1-phenyl-2-p-methylmercaptophenyl-2-chloroethanone
1-p-methylmercaptophenyl-2-phenyl-2-chloroethanone
1,2-bis-p-methylmercaptophenyl-2-chloroethanone
1-p-chlorophenyl-2-p-methylmercaptophenyl-2-chloroethanone
1-p-methylmercaptophenyl-2-p-chlorophenyl-2-chloroethanone
1-phenyl-2-p-dimethylaminophenyl-2-chloroethanone
1-p-dimethylaminophenyl-2-phenyl-2-chloroethanone
1,2-bis-(p-dimethylaminophenyl)-2-chloroethanone
1-p-chlorophenyl-2-p-dimethylaminophenyl-2-chloroethanone
1-p-dimethylaminophenyl-2-o-chlorophenyl-2-chloroethanone
1-p-dimethylaminophenyl-2-m-chlorophenyl-2-chloroethanone
1-p-dimethylaminophenyl-2-p-chlorophenyl-2-chloroethanone
1-phenyl-2-p-nitrophenyl-2-chloroethanone
1-p-nitrophenyl-2-phenyl-2-chloroethanone
1,2-bis-p-nitrophenyl-2-chloroethanone
1-p-chlorophenyl-2-p-nitrophenyl-2-chloroethanone
1-p-nitrophenyl-2-p-chlorophenyl-2-chloroethanone
1 -phenyl-2-p-aminophenyl-2-chloroethanone
1-p-aminophenyl-2-phenyl-2-chloroethanone
1,2-bis-p-aminophenyl-2-chloroethanone
1-p-chlorophenyl-2-p-aminophenyl-2-chloroethanone
1-p-aminophenyl-2-p-chlorophenyl-2-chloroethanone,
or from the corresponding 1,2-diaryl-2-bromoethanones, respectively.

EXAMPLE 23

A solution of 11 g. of ammonium dithiocarbamate in 300 ml. of absolute ethanol is heated, after the addition of 16.7 g. of ethyl bromacetate, for 1 ½ hours to 60°. The ethyl ester of aminothiocarbonylmercaptoacetic acid is formed in the solution. Then, 12 g. of 1,2-bis-p-chlorophenyl-2-chloroethanone is added thereto, and the reaction mixture is refluxed for 12 hours. A mixture is thus obtained intermediarily which contains the ethyl ester of S-(1,2-bis-p-chlorophenyl-2-oxoethyl)-mercaptocarbonimidoyl-nercaptoacetic acid. The solvent is removed by evaporation. The mixture is worked up as usual, thus obtaining, after purification by chromatography on silica gel, the ethyl ester of 4,5-bis-p-chlorophenyl-2-thiazolyl-mercaptoacetic acid, m.p. 90°-91°.

In an analogous manner, the corresponding thiazole derivatives of Formula I (Z = S, $R_1$ = esterified COOH group) are produced from the corresponding 1,2-diaryl-2-chloro- or -2-bromoethanones, respectively, by reaction with aminothiocarbonylmercaptoacetic acid esters (e.g. the methyl or ethyl ester of aminothiocarbonylmercaptoacetic acid).

EXAMPLE 24

2 g. of 4,5-diphenyl-oxazolyl-2-mercaptoacetic acid is introduced, at 0° to +5°, batchwise into 10 ml. of fuming $HNO_3$. The reaction mixture is agitated for 15 minutes at 0° to +5°, then poured into ice water, and filtered. The residue is washed with water, dried, purified by chromatography on silica gel (benzene : methanol 8:2), thus producing 4,5-bis-p-nitrophenyl-2-oxazolyl-mercaptoacetic acid.

Analogously, by nitrating the corresponding, unsubstituted compounds, the corresponding nitro compounds of Formula I are obtained, for example:
4-p-nitrophenyl-5-p-chlorophenyl-2-oxazolyl-mercapto-acetic acid
4-p-chlorophenyl-5-p-nitrophenyl-2oxazolyl-mercapto-acetic acid
2-(4,5-bis-p-nitrophenyl-2-oxazolyl-mercapto)-propionic acid
3-(4,5-bis-p-nitrophenyl-2-oxazolyl-mercapto)-propionic acid (m.p. 203°-207°)
2-(4,5-bis-p-nitrophenyl-2-oxazolyl-mercapto)-butyric acid.

EXAMPLE 25

90 g. of $SnCl_2.2H_2O$ are dissolved in 225 ml. of concentrated hydrochloric acid and 15 g. of 4,5-bis-p-nitrophenyl-2-oxazolyl-mercapto-acetic acid are added to the mixture which is stirred for a short time and then kept for 24 hours at room temperature. After filtration, the precipitate is added to 300 ml. of water. The suspension is neutralized with aqueous ammonia solution, stirred for 2 hours at room temperature and filtered. The precipitate is washed with water, dried and extracted in an extraction apparatus with ethyl acetate. From the extract there is obtained 4,5-bis-p-aminophenyl-2-oxazolyl-mercapto-acetic acid.

Analogously, by reduction of the corresponding nitro compounds, the corresponding amino compounds of Formula I are obtained, for example:
4-p-aminophenyl-5-p-chlorophenyl-2-oxazolyl-mercapto-acetic acid
4-p-chlorophenyl-5-p-aminophenyl-2-oxazolyl-mercapto-acetic acid
2-(4,5-bis-p-aminophenyl-2-oxazolyl-mercapto)-propionic acid
3-(4,5-bis-p-aminophenyl-2-oxazolyl-mercapto)-propionic acid
2-(4,5-bis-p-aminophenyl-2-oxazolyl-mercapto)-butyric acid.

EXAMPLE 26

A soltuion of 3.5 g. of $NaNO_2$ in 10 ml. of water is added dropwise at 0° to a solution of 8.5 g. of 4,5-bis-p-aminophenyl-2-oxazolyl-mercaptoacetic acid in 125 ml.

of 15% hydrochloric acid. Thereafter, 12 ml. of a 40% HBF₄ solution is added dropwise thereto, the mixture is buffered to a pH of 5-6, the thus-precipitated diazonium tetrafluoroborate is filtered, washed with water, dried, and introduced in incremental portions into 100 ml. of boiling xylene. After termination of the decomposition reaction, the mixture is concentrated by evaporation, worked up as usual (with the addition of carbon), and after purification by chromatography on silica gel, 4,5-bis-p-fluorophenyl-2-oxazolylmercaptoacetic acid is obtained.

Analogously, the corresponding fluorine compounds of Formula I are produced from the corresponding amino compounds by diazotization and reaction with HBF₄, for example:
4-p-fluorophenyl-5-p-chlorophenyl-2-oxazolyl-mercaptoacetic acid
4-p-chlorophenyl-5-p-fluorophenyl-2-oxazolyl-mercaptoacetic acid
2-(4,5-bis-p-fluorophenyl-2-oxazolyl-mercapto)-propionic acid
3-(4,5-bis-p-fluorophenyl-2-oxazolyl-mercapto)-propionic acid
2-(4,5-bis-p-fluorophenyl-2-oxazolyl-mercapto)-butyric acid.

EXAMPLE 27

13 g. of 4,5-bis-p-aminophenyl-2-oxazolyl-mercaptoacetic acid is dissolved in 150 ml. of water and 50 ml. of concentrated HCl, mixed at 0°-5° with 5.3 g. of NaNO₂ in 12 ml. of water, gradually added dropwise to a hot Cu₂Cl₂ solution (obtained by the reduction of 16 g. of CuSO₄ with SO₂ in 100 ml. of water in the presence of 20 g. of NaCl), heated for another 30 minutes to 90°-95°, cooled, saturated with H₂S, and filtered. The filtrate is worked up as usual, thus obtaining 4,5-bis-p-chlorophenyl-2-oxazolyl-mercaptoacetic acid, m.p. 151°-153°.

Analogously, the corresponding chlorine compounds of Formula I are produced from the corresponding amino compounds by diazotization and reaction with Cu₂Cl₂, for example:
2-(4,5-bis-p-chlorophenyl-2-oxazolyl-mercapto)-propionic acid
3-(4,5-bis-p-chlorophenyl-2-oxazolyl-mercapto)-propionic acid
2-(4,5-bis-p-chlorophenyl-2-oxazolyl-mercapto)-butyric acid.

EXAMPLE 28

8.5 g. of 4,5-bis-p-aminophenyl-2-oxazolyl-mercaptoacetic aciid is dissolved in 60 ml. of water and 6 ml. of concentrated H₂SO₄, mixed dropwise at 0°-5° with a solution of 3.5 g. of NaNO₂ in 10 ml. of water, and this solution is added dropwise to a boiling solution of 3.3 g. of CuSO₄ . 5H₂O, 7.7 g. of NaBr, and 1 g. of powdered copper (previously refluxed for 4 hours and then mixed with 0.13 g. of Na₂SO₃). This reaction mixture is heated for 30 minutes to 95°, cooled, saturated with H₂S, filtered, and the filtrate worked up as usual, thus producing 4,5-bis-p-bromophenyl-2-oxazolyl-mercaptoacetic acid.

Analogously, the corresponding bromine compounds of Formula I are obtained from the corresponding amino compounds by diazotization and reaction with NaBr in the presence of copper sulfate.

EXAMPLE 29

8.5 g. of 4,5-bis-p-aminophenyl-2-oxazolyl-mercaptoacetic acid is dissolved in 60 ml. of 18% sulfuric acid and diazotized at 0°-5° with 3.7 g. of NaNO₂ in 6 ml. of water. This solution is introduced under agitation into a mixture of 12.5 g. of KI in 25 ml. of 1N H₂SO₄. The mixture is stirred overnight, heated for 30 minutes on a water bath, decolorized with carbon, worked up as usual, and 4,5-bis-p-iodophenyl-2-oxazolyl-mercaptoacetic acid is thus produced.

In an analogous manner, the corresponding iodine compounds of Formula I are obtained from the corresponding amino compounds by diazotization and reaction with HI.

EXAMPLE 30

8.5 g. of 4,5-bis-p-aminophenyl-2-oxazolyl-mercaptoacetic acid is dissolved in 100 ml. of 10% hydrochloric acid. The mixture is cooled to 5°, and a solution of 3.5 g. of NaNO₂ in 10 ml. of water is added dropwise. This diazonium salt solution is added gradually and dropwise, under agitation at 70°, beneath the surface of a solution of 2.7 g. of methyl mercaptan in 40 ml. of 20% sodium hydroxide solution. Then, the mixture is headed for 30 minutes, cooled, acidified, filtered, and 4,5-bis-p-methylmercapto-phenyl-2-oxazolyl-mercaptoacetic acid is thus produced.

Analogously, the corresponding methylmercapto compounds of Formula I are obtained from the corresponding amino compounds by diazotization and reaction with methyl mercaptan.

EXAMPLE 31 a. 8.5 g. of 4,5-bis-p-aminophenyl-2-oxazolyl-mercaptoacetic acid is dissolved in 100 ml. of 10% hydrochloric acid. The mixture is then cooled to 5°, and a solution of 3.5 g. of NaNO₂ in 10 ml. of water is added dropwise. The thus-obtained diazonium salt solution is added dropwise under agitation to a solution of 8 g. of potassium ethyl xanthate in 50 ml. of water, warmed to 40°-50°. After the evolution of nitrogen has ceased, the reaction mixture is cooled, and the pH is adjusted to 4-6. The thus-separated 4,5-bis-p-ethylxanthophenyl-2-oxazolyl-mercaptoacetic acid is filtered and dissolved in 75 ml. of 4N sodium hydroxide solution. Under a nitrogen stream, the mixture is refluxed for one hour, then cooled and adjusted to a pH of 4-6 with hydrochloric acid. The thus-precipitated 4,5-bis-p-mercaptophenyl-2-oxazolylmercaptoacetic acid is filtered off.

b. The crude acid obtained according to (a) is dissolved in 125 ml. of 1N sodium hydroxide solution and mixed, under nitrogen, batchwise with 13 g. of dimethyl sulfate. The mixture is stirred for 30 minutes at room temperature, mixed with 50 ml. of 2N NaOH, refluxed for one-half hour under agitation, cooled to 0°, and acidified with hydrochloric acid, thus obtaining 4,5-bis-p-methylmercaptophenyl-2-oxazolyl-mercaptoacetic acid.

Analogously, the corresponding mercapto compounds and alkyl-mercapto compounds, respectively, of Formula I are produced from the corresponding amino compounds, after diazotization and successive reactions with potassium ethyl xanthate, sodium hydroxide solution, and dimethyl sulfate, diethyl sulfate, propyl bromide, or diisopropyl sulfate; for example:
4,5-bis-p-ethylmercaptophenyl-2-oxazolyl-mercaptoacetic acid 4,5-bis-p-n-propylmercaptophenyl-2-oxazolyl-mercaptoacetic acid
4,5-bis-p-isopropylmercaptophenyl-2-oxazolyl-mercaptoacetic acid.

EXAMPLE 32 a. 8.5 g. of 4,5-bis-p-aminophenyl-2-oxazolyl-mercaptoacetic acid is dissolved in 50 ml. of 10% sulfuric acid and diazotized at 0°–5° by the addition of 3.5 g. of NaNO$_2$ in 8 ml. of water. The diazonium salt solution is introduced under stirring into 250 ml. of boiling water. Subsequently, the reaction mixture is refluxed for 30 minutes, cooled, acidified, and 4,5-bis-p-hydroxyphenyl-2-oxazolyl-mercaptoacetic acid is obtained.

Analogously, the corresponding hydroxy compounds of Formula I are produced from the corresponding amino compounds by diazotization and refluxing.

b. The crude 4,5-bis-p-hydroxyphenyl-2-oxazolylmercaptoacetic acid obtained in accordance with (a) is dissolved, under a nitrogen atmosphere, in 125 ml. of 1N sodium hydroxide solution and mixed batchwise under stirring with 13 g. of dimethyl sulfate. The thus-formed methyl ester of 4,5-bis-p-methoxyphenyl-2-oxazolylmercaptoacetic acid separates gradually as an oil. After one-half hour of agitation, 50 ml. of 2N sodium hydroxide solution is added; the mixture is refluxed under stirring for one-half hour, cooled to 0°, acidified, and 4,5-bis-p-methoxyphenyl-2-oxazolyl-mercaptoacetic acid is thus produced, m.p. 140–141°.

Analogously, the corresponding alkoxy compounds of Formula I are obtained from the corresponding hydroxy compounds by reaction with dimethyl sulfate or isopropyl bromide; for example:
4,5-bis-p-ethoxyphenyl-2-oxazolyl-mercaptoacetic acid
4,5-bis-p-n-propyloxyphenyl-2-oxazolyl-mercaptoacetic acid
4,5-bis-p-isopropyloxyphenyl-2-oxazolyl-mercaptoacetic acid.

EXAMPLE 33

14 g. of 4,5-diphenyl-2-oxazolyl-mercaptoacetic acid is dissolved in a mixture of 45 ml. of dioxane, 2.8 g. of KOH, and 20 ml. of water and mixed, under agitation at 5°–7°, dropwise with a solution of 15 g. of bromine in 160 ml. of dioxane (duration about 2 hours). The mixture is concentrated by evaporation, the residue dissolved in 50 ml. of water, and worked up as usual, thus producing 4,5-bis-p-bromophenyl-2-oxazolyl-mercaptoacetic acid.

Analogously, the corresponding bromine compounds of Formula I are obtained by bromination from the corresponding unsubstituted compounds.

EXAMPLE 34

A solution of 3.07 g. of the ethyl ester of 4,5-diphenyl-2-oxazolyl-mercaptoacetic acid in the minimum amount of ether is treated with dry chlorine; the progress of the chlorination reaction is observed by means of thin-layer chromatography. After the termination of the reaction, the mixture is filtered, the filtrate is evaporated, and the residue is chromatographed on silica gel, thus obtaining the ethyl ester of 4,5-bis-p-chlorophenyl-2-oxazolyl-mercaptoacetic acid (m.p. 122°–124°).

In an analogous manner, the chlorine compounds of Formula I are obtained by chlorination of the corresponding unsubstituted compounds.

EXAMPLE 35

14 g. of 4,5-diphenyl-2-oxazolyl-mercaptoacetic acid is dissolved in 70 ml. of acetic acid and mixed, under agitation, with 1 g. of mercury oxide and 20 g. of finely pulverized iodine. The mixture is stirred for 48 hours at room temperature, poured onto water, filtered, the thus-obtained product taken up in ethanol, and treated with sodium thiosulfate solution. The ethanol is removed by evaporation, and the aqueous solution is worked up as usual, thus obtaining 4,5-bis-p-iodophenyl-2-oxazolyl-mercaptoacetic acid.

Analogously, by iodation, the remaining iodine compounds of Formula I are obtained from the corresponding unsubstituted compounds.

EXAMPLE 36

30 g. of the diethyl ester of α-(4,5-diphenyl-2-oxazolyl-mercapto)-α-methylmalonic acid (obtainable by reacting the sodium compound of 2-mercapto-4,5-diphenyl-oxazole with the diethyl ester of bromomethylmalonic acid) is saponified for 3 hours with 500 ml. of 10% ethanolic KOH solution. The ethanol is distilled off, the residue is introduced into 1 l. of water, and acidified to a pH of 4–6 -with hydrochloric acid. The thus-precipitated α-(4,5-diphenyl-2-oxazolyl-mercapto)-α-methylmalonic acid is filtered off, dried, dissolved in acetone, and the solution is filtered and evaporated. The residue is heated to 100°–120°/20 mm. until the evolution of CO$_2$ has ceased, thus producing 2-(4,5-diphenyl-2-oxazolyl-mercapto)-propionic acid (m.p. 89°–91°).

Analogously, from the corresponding diethyl esters of oxazolyl-mercapto- or thiazolyl-mercapto-α-alkylmalonic acid, respectively, for example from:
the diethyl ester of α-(4,5-diphenyl-2oxazolyl-mercapto)-α-ethylmalonic acid
the diethyl ester of α-(4,5-bis-p-chlorophenyl-2-oxazolyl-mercapto)-α-methylmalonic acid
the diethyl ester of α-(4,5-bis-p-chlorophenyl-2-oxazolyl-mercapto)-α-ethylmalonic acid,
by saponification and decarboxylation, the corresponding 4,5-diaryl-2-oxazolyl-mercapto-fatty acids of Formula I are obtained.

EXAMPLE 37

4.14 g of 4,5-bis-p-aminophenyl-2oxazolyl-mercaptoacetic acid dihydrochloride is dissolved in 100 ml. of 1N sodium hydroxide solution and mixed, under vigorous agitation and cooling, dropwise with 3 g. of acetic anhydride. The mixture is allowed to stand overnight at 25°, then hydrochloric acid is added to a pH of 3–6, and the mixture separated from the precipitated substance, thus obtaining 4,5-bis-p-acetamidophenyl-2-oxazolyl-mercaptoacetic acid.

Analogously, by acylation of the corresponding amino compounds with acetic anhydride or propionic anhydride, butyric anhydride, or isobutyric anhydride, the corresponding acylamino compounds of Formula I are produced, for example:
4-phenyl-5-p-acetamidophenyl-2oxazolyl-mercaptoacetic acid
4-p-acetamidophenyl-5phenyl-2-oxazolyl-mercaptoacetic acid
4-p-chlorophenyl-5-p-acetamidophenyl-2-oxazolyl-mercaptoacetic acid
4-p-acetamidophenyl-5-p-chlorophenyl-2-oxazolyl-mercaptoacetic acid 4,5-bis-propionamidophenyl-2-oxazolyl-mercaptoacetic acid 4,5-bis-butyramidophenyl-2-oxazolyl-mercaptoacetic acid 4,5bis-isobutyramidophenyl-2-oxazolyl-mercaptoacetic acid.

EXAMPLE 38

4 g. of 4,5-bis-p-aminophenyl-2-oxazolyl-mercaptoacetic acid dihydrochloride is mixed, in 50 ml. of pyridine, under agitation and ice cooling with 3.5 g. of acetyl chloride. After 2 hours, 50 ml. of water is added and the mixture is allowed to stand overnight, mixed with another 200 ml. of water, and acidified with hydrochloric acid, thus obtaining 4,5-bis-p-acetamido-phenyl-2-oxazolyl-mercaptoacetic acid.

Analogously, by acylation of the corresponding amino compounds with acetyl, propionyl, butyryl, isobutyryl, or valeryl chloride, respectively, the corresponding acylamido compounds of Formula I are produced.

EXAMPLE 39

3.9 g. of the ethyl ester of 4-p-aminophenyl-5-p-chlorophenyl-2-oxazolyl-mercaptoacetic acid is heated with 3 g. of 90% strength formic acid and 2 g. of 39% strength formaldehyde solution for 20 hours to 60°. The mixture is diluted with water, made alkaline with sodium hydroxide solution, and immediately worked up as usual, thus obtaining the ethyl ester of 4-p-dimethylaminophenyl-5-p-chlorophenyl-2-oxazolyl-mercaptoacetic acid (m.p. 106°-107°).

Analogously, the remaining dimethylamino compounds of Formula I are produced from the corresponding amino compounds by methylation with formaldehyde/formic acid.

EXAMPLE 40

3.4 g. of 4-p-aminophenyl-5-p-chlorophenyl-2-oxazolyl-mercaptoacetic acid is boiled in 20 ml. of n-butanol, together with 4 g. of methyl iodide and 3 g. of pulverized potassium carbonate for 2 hours. The mixture is then mixed with 10 ml. of water and 0.5 g. of KOH, refluxed for 2 hours, cooled, acidified with hydrochloric acid, and the butanol phase is separated, dried over sodium sulfate, filtered, evaporated, and 4-p-dimethylamino-phenyl-5-p-chlorophenyl-2-oxazolyl-mercaptoacetic acid (m.p. 130°-132° is thus obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and without departing from the spirit and scope thereof, can make various changes and modifications of the invention to adapt it to various usages and conditions.

What is claimed is:

1. A pharmaceutical composition comprising, in admixture with a solid, liquid or semiliquid pharmaceutically acceptable carrier, an antinflammatorily effective amount per unit dosage of a compound of the formula

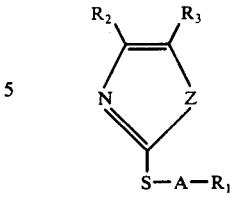

wherein $R_1$ is carboxyl, a physiologically acceptable $C_{1-12}$ alkyl ester thereof, —$CONH_2$ or —CN; $R_2$ and $R_3$ each are phenyl or phenyl mono- or di-substituted by at least one member selected from the group consisting of alkyl, alkoxy alkylmercapto, monoalkylamino, dialkylamino or alkanoylamino wherein the alkyl, alkoxy and alkanoyl are each of up to 4 carbon atoms, F, Cl, Br, I, $CF_3$, OH, methylenedioxy, $NH_2$ and $NO_2$; A is $C_nH_{2n}$ wherein n is an integer from 1 to 10 inclusive; and Z is O or S, or a physiologically acceptable salt thereof.

2. A composition of claim 1, wherein $R_1$ is —COOH, —$COOCH_3$ or —$COOC_2H_5$.

3. A composition of claim 1, wherein A is —$CH_2$—, —$CH(CH_3)$ or —$CH(C_2H_5)$—.

4. A composition of claim 1, wherein $R_2$ and $R_3$ are phenyl or phenyl monosubstituted by methyl, methoxy, methylmercapto, F, Cl, Br or $CF_3$.

5. A composition of claim 4, wherein $R_1$ is —COOH, —$COOCH_3$ or —$COOC_2H_5$ and A is —$CH_2$—, —$CH(CH_3)$— or —$CH(C_2H_5)$—.

6. A composition of claim 4, wherein $R_2$ and $R_3$ are phenyl or p-chlorophenyl.

7. A composition of claim 6, wherein $R_1$ is —COOH, —$COOCH_3$ or —$COOCH_2H_5$ and A is —$CH_2$—, —$CH(CH_3)$— or —$CH(C_2H_5)$—.

8. A composition of claim 1, where the compound is 4,5-diphenyl-2-oxazolyl-mercaptoacetic acid.

9. A composition of claim 1, where the compound is 4,5-diphenyl-2-oxazolyl-mercaptoacetic acid ethyl ester.

10. A composition of claim 1, where the compound is 4,5-bis-p-chlorophenyl-2-oxazolyl-mercaptoacetic acid.

11. A composition of claim 1 wherein the compound is selected from the group consisting of 4,5-bis-p-chlorophenyl-2-oxazolyl-mercaptoacetic acid methyl ester, 4,5bis-p-chlorophenyl-2-oxazolyl-mercaptoacetic acid ethyl ester, the corresponding -mercaptoacetamide and the corresponding -mercaptoacetonitrile.

12. A composition of claim 1 where the compound is 2-(4,5-bis-p-chlorophenyl-2-oxazolyl-mercapto)-propionic acid.

13. A composition of claim 1 where the compound is 2-(4,5-bis-p-chlorophenyl-2-oxazolyl-mercapto)-propionic acid. ethyl ester.

14. A composition of claim 1 where the compound is 2-(4,5-bis-p-chlorophenyl-2-oxazolyl-mercapto)-butyric acid.

15. A composition of claim 1 where the compound is 2-(4,5-bis-p-chlorophenyl-2-oxazolyl-mercapto)-butyric acid ethyl ester.

16. A composition of claim 1 wherein the compound is selected from the group consisting of 2-(4,5-diphenyl-2-oxazolyl-mercapto)-propionic acid, 2-(4,5-diphenyl-2-oxazolyl-mercapto)-butyric acid, 2-(4,5-diphenyl-2-oxazolyl-mercapto)-2-methylpropionic acid, 3-(4,5-diphenyl-2-oxazolyl-mercapto)-propionic acid, 4-(4,5-diphenyl-2-oxazolyl-mercapto)-butyric acid, 7-(4,5-diphenyl-2-oxazolyl-mercapto)-heptanoic acid, 4,5-bisp-tolyl-2-oxazolyl-mercaptoacetic acid, 2-(4,5-bis-p-tolyl-2-oxazolyl-mercapto)-propionic acid, 2-(4,5-bis-p-tolyl-2-oxazolyl-mercapto)-butyric acid, 4,5-bis-p-isopropylphenyl-2-oxazolyl-mercaptoacetic acid, 2-(4,5-bis-p-isopropylphenyl-2-oxazolyl-mercapto)-propionic acid, 4,5-bis-o-chlorophenyl-2-oxazolyl-mercaptoacetic acid, 3-(4,5-bis-p-chlorophenyl-2-oxazolyl-mercapto)-propionic acid, 4-p-methoxyphenyl-5-phenyl-2-oxazolyl-mercaptoacetic acid, 4,5-bis-m-methoxyphenyl-2-oxazolyl-mercaptoacetic acid, 4,5-bis-p-methoxyphenyl-2-oxazolyl-mercaptoacetic acid, 2(4,5-bis-p-methoxyphenyl-2oxazolyl-mercapto)-propionic acid, 2-(4,5-bis-p-methoxyphenyl-2-oxazolyl-mercapto)-butyric acid, 4-p-methoxyphenyl-5-o-chlorophenyl-2-oxazolyl-mercaptoacetic acid, 4,5-bis-(3,4-dimethoxyphenyl)-2-oxazolyl-mercaptoacetic acid, 4,5-bis-(3,4-methylenedioxyphenyl)-2-oxazolyl-mercaptoacetic acid, 2-[4,5-bis-p-methylenedioxyphenyl)-2-oxazolyl-mercapto]-propionic acid, 4-(3,4-methylenedioxyphenyl)-5-p-chlorophenyl-2-oxazolyl-mercaptoacetic acid, 4-p-dimethylaminophenyl-5-phenyl-2-oxazolyl-mercaptoacetic acid, 4-p-dimethylaminophenyl-5-o-chlorophenyl-2-oxazolyl-mercaptoacetic acid, 4-p-dimethylaminophenyl-5-p-chlorophenyl-2-oxazolyl-mercaptoacetic acid, 4,5-diphenyl-2-thiazolyl-mercaptoacetic acid, 2-(4,5-diphenyl-2-thiazolyl-mercapto)-2-methylpropionic acid, 4-(4,5-diphenyl-2-thiazolyl-mercapto)-butyric acid, 7-(4,5-diphenyl-2-thiazolyl-mercapto)-heptanoic acid, 4-p-tolyl-5phenyl-2-thiazolyl-mercaptoacetic acid, 4-fluorophenyl-5-phenyl-2-thiazolyl-mercaptoacetic acid, 4,5-bis-p-chlorophenyl-2-thiazolyl-mercaptoacetic acid, and the ethyl ester of each.

17. A composition of claim 1 adapted for oral ingestion.

18. A method of treating inflammations which comprise administering to the affected patient an antiinflammatorily effective amount of a composition of claim 1.

19. A method of claim 18 wherein the composition is administered orally.

* * * * *

UNITED STATES PATENT AND TRADEMARK OFFICE
CERTIFICATE OF CORRECTION

PATENT NO. : 4,051,250
DATED : September 27, 1977
INVENTOR(S) : JOHANN DAHM ET AL.

It is certified that error appears in the above-identified patent and that said Letters Patent are hereby corrected as shown below:

Claim 7, col. 60, line 33: Change "-COOCH$_2$H$_5$" to -- -COOC$_2$H$_5$ --

Claim 16, col. 61, line 12: Change "2oxazolyl" to -- 2-oxazolyl --

Claim 16, col. 61, line 18: Change "p-methylenedioxyphenyl" to -- (3,4-methylenediozyphenyl --.

Claim 16, col. 62, line 9 : Change "-5phenyl" to -- -5-phenyl --.

Signed and Sealed this

Seventh Day of March 1978

[SEAL]

Attest:

RUTH C. MASON
Attesting Officer

LUTRELLE F. PARKER
Acting Commissioner of Patents and Trademarks